US007202035B2

(12) United States Patent
Squires et al.

(10) Patent No.: US 7,202,035 B2
(45) Date of Patent: Apr. 10, 2007

(54) GENETIC MARKERS FOR SKATOLE METABOLISM

(75) Inventors: E. James Squires, Guelph (CA); Gonzalo J. Diaz, Bogota, DC (US)

(73) Assignee: University of Guelph (CA)

( * ) Notice: Subject to any disclaimer, the term of this patent is extended or adjusted under 35 U.S.C. 154(b) by 538 days.

(21) Appl. No.: 10/434,966

(22) Filed: May 9, 2003

(65) Prior Publication Data

US 2003/0228614 A1    Dec. 11, 2003

Related U.S. Application Data

(60) Continuation-in-part of application No. 10/206,118, filed on Jul. 29, 2002, which is a division of application No. 09/672,039, filed on Sep. 29, 2000, now Pat. No. 6,448,028.

(60) Provisional application No. 60/156,935, filed on Sep. 30, 1999.

(30) Foreign Application Priority Data

| Mar. 4, 2000 | (CA) | .................................... 2383887 |
| Sep. 29, 2000 | (CA) | .................... PCT/CA00/01129 |
| Sep. 29, 2000 | (EP) | ............................... 00963835.4 |

(51) Int. Cl.
  *C12Q 1/70*   (2006.01)
  *C12N 9/00*   (2006.01)
  *C12N 9/02*   (2006.01)
  *C07H 21/04*  (2006.01)

(52) U.S. Cl. ................. 435/6; 435/4; 435/25; 435/183; 435/189; 536/23.2

(58) Field of Classification Search .................... 435/4, 435/6, 69.1, 183, 189; 536/23.2, 23.5, 24.31, 536/24.32
See application file for complete search history.

(56) References Cited

U.S. PATENT DOCUMENTS 4,906,563 A    3/1990  Singh et al.

FOREIGN PATENT DOCUMENTS

| CA | 2 234349 A | 10/1999 |
| CA | 2234349 | 10/1999 |
| DK | 171085 | 6/1994 |
| WO | WO 08 02597 A | 11/1980 |
| WO | WO 89 06361 A | 7/1989 |
| WO | WO/02/24945 A2 | 3/2002 |

OTHER PUBLICATIONS

Diaz, Gonzalo J et al., Identification of phase I metabolites of 3-methylindole produced by pig liver microsomes. *Drug Metabolism and Disposition*, vol. 27, No. 10, Oct. 1999, pp. 1150-1156.
Diaz, Gonzalo J et al., Metabolism of 3-methylindole by porcine liver microsomes: Responsible cytochrome P450 enzymes, *Toxicological Sciences*, vol. 55, No. 2, Jun. 2000, pp. 284-292.
Diaz, Gonzalo J et al., Role of aldehyde oxidase in the hepatic in vitro metabolism of 3-methylindole in pigs, *Journal of Agricultural and Food Chemistry*, vol. 48, No. 3, Mar. 2000, pp. 833-837.
Database WPI AN 1996 107098 Fremgangsmade til at undersoge grise for at bestemme om de er egnet til avl eller formering samt anvendelse af dyr eller saed (Slagteriernes Forskningsinstitut), May 28, 1996.
Thornton-Manning, Janice et al., Metabolism of 3-methylindole by vaccinia-expressed p450 enzymes: Correlation of 3-methyleneindolenine formation and protein-binding, *Journal of Pharmacology and Experimental Therapeutics*, vol. 276, No. 1, 1996, pp. 21-29.
Skordos, Konstantine, W. et al. Evidence supporting the formation of 2,3-epoxy-3-methylindoline: A reactive intermediate of the pneumotoxin 3-methylindole, *Chemical Research in Toxicoloy*, vol. 11, No. 7, Jul. 1998 pp. 741-749.
Potchoiba, M.J. et al., Metabolism and Pneumo Toxicity of 3 Methyl Oxindole Indole 3 Carbinol and 3 methyl indole in goats, *American Journal of Veterinary Research*, vol. 43, No. 8, 1982, pp. 1418-1423.
Babol, J. et al., (1998) Hepatic metabolism of skatole in pigs by cytochrome P4502E1.J.Anim.Sci.76: 822-828.
Babol, J. et al., (1998) Relationship between oxidation and conjugation metabolism of skatole in pig liver and concentrations of skatole in fat. J.Anim Sci. 76:829-838.
Baek, C.E. et al. (1995) Identification and quantification of selected metabolites of skatole-possibilities for metabolic profiling of pigs, Proc.EAAP Working Group Production and Utilisation of Meat from Entire Male Pigs, Milton Keynes, INRA and MLC.
Baek, E. et al. (1997) Identification of selected metabolites of skatole in plasma and urine form pigs. J. Agric Food Chem 45:2332-2340.
Beedham, C. et al. (1995) role of aldehyde oxidase in biogenic amine metabolism. Prog. Brain Res., 106, 345-353.

(Continued)

*Primary Examiner*—Manjunath N. Rao
(74) *Attorney, Agent, or Firm*—McKee, Voorhees & Sease, P.L.C.

(57) ABSTRACT

Novel metabolites and enzymes involved in skatole metabolism are disclosed. The novel metabolites are 3-OH-3-methylindolenine (HMI); 3-methyloxindole (3MOI); indole-3-carbinol (I-3C); and 2-aminoacetophenone (2-AM). Measuring levels of these metabolites in a pig may be useful in identifying the pig's ability to metabolize skatole and its susceptibility to boar taint. The novel enzymes involved in skatole metabolism are aldehyde oxidase and CYP2A6. Enhancing the activity of these enzymes may be useful in enhancing skatole metabolism and reducing boar taint. The identification of the enzyme also allows the development of screening assays for substances that interact with these enzymes and skatole metabolism or for genetic screening to identify pigs on the basis of their skatole metabolism. Pigs having high levels of these enzymes may be selected and bred to produce pigs that have a lower incidence of boar taint.

7 Claims, 15 Drawing Sheets

OTHER PUBLICATIONS

Claus, R. et al. (1994) Physiological aspects of androstenone and skatole formation in the boar-a review with experimental data. Meat Sci. 38:289-305.

Diaz, G.J. et al. (1999) Identification of Phase 1 metabolites of 3-methylindole produced by pig liver microsomes. Drug Metab. Dispos. 27:1150-1156.

Friis, C. (1993) Distribution, metabolic fate and elimination of skatole in the pig. In: M. Bonneau (Ed.) Measurement and prevention of boar taint in intact male pigs. p. 113-115. INRA Edition, Paris.

Lundstom, K. et al. (1994) Skatole levels in pigs selected for high lean tissue growth rate on different protien levels, Livest. Prod. Sci. 38:125-132.

Squires, E.J. et al. (1997) Relationship between cytochrome P450IIE1 in liver and levels of skatole and its metabolites in intact male pigs. J. Anim. Sci. 75:2506-2511.

Andersson, K. et al., "Relations between boar taint and puberty in entire pig males", EEAP Pub. No. 92, pp. 7-73, Oct. 1-3, 1997.

Babol J. et al., "Factors regulating the concentrations of 16-androstene steroids in submaxillary salivary glands of pigs", Journal of Animal Science, Vo. 74, pp. 413-419, 1996.

Babol, J. et al., "Relationship between metabolism of androstenone and skatole", EEAP Pub. No. 92, pp. 62-65, Oct. 1-3, 1997.

Babol, J. et al., "Hepatic Metabolism of Skatole in Pigs by Cytochrome P4502E1", J Anim Sci, vol. 76, No. 3 pp. 822-828, 1998.

Babol, J., et al., "Involvement of cytochrome P450IIE1 in hepatic metabolism and clearance of skatole", EEAP Pub. No. 92, pp. 49-53, Oct. 1-3, 1997.

Babol, J. et al., Relationships between oxidation and conjugation metabolism of skatole in pig liver and levels of skatole in fat, EEAP Pub. No. 92, pp. 54-57, Oct. 1-3, 1997.

Baek, C. et al., "Identification of Selected Metabolites of Skatole in Plasma and Urine from Pigs", J Agric Food Chem, vol. 45, pp. 2332-2340, 1997.

Claus, R. et al., "Oestrogens, compared to other steroids of testicular origin, in bloodplasma of boars", Acta Endocrino, vol. 94, pp. 404-411, 1980.

Database WPI, Derwent Publications Ltd., London, GB; AN 1996-107098; Jens Hansen-Moller: Fremgangsmade til at undersoge grise for at bestemme om de er egnet til avl eller formering samt anvendelse af dyr eller saed & DK 171 085 B (Slagteriernes Forskningsinstitut) May 28, 1996.

Diaz, Gonzalo J et al., "Identification of phase I metabolites of 3-methylindole produced by pig liver microsomes", Drug Metabolism and Disposition, vol. 27, No. 10, pp. 1150-1156, Oct. 1999.

Diaz, Gonzalo J. et al., "Metabolism of 3-methylindole by porcine liver microsomes: Responsible cytochrome P450 enzymes", Toxicological Sciences, vol. 55, No. 2, pp. 284-292, Jun. 2000.

Diaz, Gonzalo J. et al., "Role of aldehyde oxidase in the hepatic in vitro metabolism of 3-methylindole in pigs", J of Agric and Food Chemistry, vol. 48, No. 3, pp. 833-837, Mar. 2000.

Edwards, S.M. et al., "Involvement of cytochrome b5 in androstenone biosynthesis", EREAP Pub. No. 92, pp. 66-69, Oct. 1-3, 1997.

Friis, C., "Is boar-taint related to sex differences or polymorphism of skatole metabolism", Proc of Meeting of EAAP Working Group, Meat & Lovestock Comm., Sep. 27-29, 1995.

Griffin, M. J., et al. "p-Nitrophenol UDP Glucuronyltransferase and Epoxide Hydrase in Microsomes from Liver of Rates Fed 2-Acetylaminofluorene and Barbitol" Proc. Okla. Acad. Sci. 59:12-15 (1979).

Jensen, M.T. et al., "Microbial production of skatole in the hind gut of pigs fed different diets and its relation to skatole deposition in backfat", Proc of Meeting of EAAP Working Group, Meat & Livestock Comm., UK, Sep. 27-29, 1995.

Laue, A. et al., "Effect of tryptophan infusion on the production of indole derivatives in the hind gut and absorption to the portal vein", EEAP Pub. No. 92, pp. 58-61., Oct. 1-3, 1997.

Lundstrom, K., et al., "Skatole levels in pigs selected for high lean tissue growth rate on different dietary protein levels", Livestock Prod Sci, vol. 38, pp. 125-132, 1884.

Marini, S., et al. "Xenobiotic-metabolizing enzymes in pig nasal and hepatic tissues" XENOBIOTICA, 1998, vol. 28, No. 10, 923-935.

Meadus W.J. et al., "Cytochrome P450c17 from porcine and bovine adrenal catalyses the formation of 5,16-androstadien-3beta-ol from pregnenolone in the presence of cytochrome b5", The Journal of Steriod Biochemistry and Molecular Biology, vol. 46, No. 5, pp. 565-572, 1993.

Ozols, Juris, "Structure of cytochrome $b_5$ and its topology in the microsomal membrane" Biochimica et Biophysica Acta, 997 (1989) 121-130.

Potchoiba M J et al., "Metabolism and Pneumo Toxicity of 3 Methyl Oxindole Indole 3 Carbinol and 3 Methyl Indole in Goats", American Journal of Veterinary Research, vol. 43, No. 8, pp. 1418-1423, 1982.

Shibata, Noriaki et al. "Male-specific suppression of hepatic microsomal UDP-glucuronosyl transferase activities toward sex hormones in the adult male rate administered bisphenol A" Biochem. J. (2002) 368, 783-788.

Skordos Konstantine W et al., "Evidence supporting the formation of 2,3-epoxy-3-methylindoline: A reactive intermediate of the pneumotoxin 3-methylindole", Chemical Research in Toxicology, vol. 11, No. 7, pp. 741-740 1998.

Squires, E.J. and Steggles, A., "Analysis of porcine cytochrome b5 and its relation to boar taint", The BASEB Journal, vol. 11, No. 9, p. a1216, 1997.

Squires, E.J. et al., "Relationship Between Cytochrome P450IIE1 in Liver and Levels of Skatole and Its Metabolites in Intact Male Pigs", J Anim Sci, vol. 75, pp. 2506-2511, 1997.

Squires, E.J. et al., "Comparison of androst-16-ene steroid levels determined by a colorimetric assay with boar taint estimated by a trained sensory panel", Journal of Animal Science, Vo. 69, pp. 1092-1100, 1991.

Swantek, P.M. et al., "Testicular cytochrome b5, 3βHSD, and P450c17 levels of young boars and the influence of pST administration", Journal of Animal Science, vol. 73, No. Suppl. 1, 1995, p. 153.

Thornton-Manning Manice et al., "Metabolism of 3-methylindole by vaccinia-expressed P450 enzymes: Correlation of 3-methyleneindolenine formation and protein-binding", J of Pharmacology and Experimental Therapeutics, vol. 276, No. 1, pp. 21-29, 1996.

Vandermark P.K. and Steggles, A.W., "The isolation of characterization of the soluble and membrane-bound porcine cytochrome b5 cDNAs", Biochemical and Biophysical Research Communications, vol. 240, pp. 8-83, 1997.

FIGURE 1
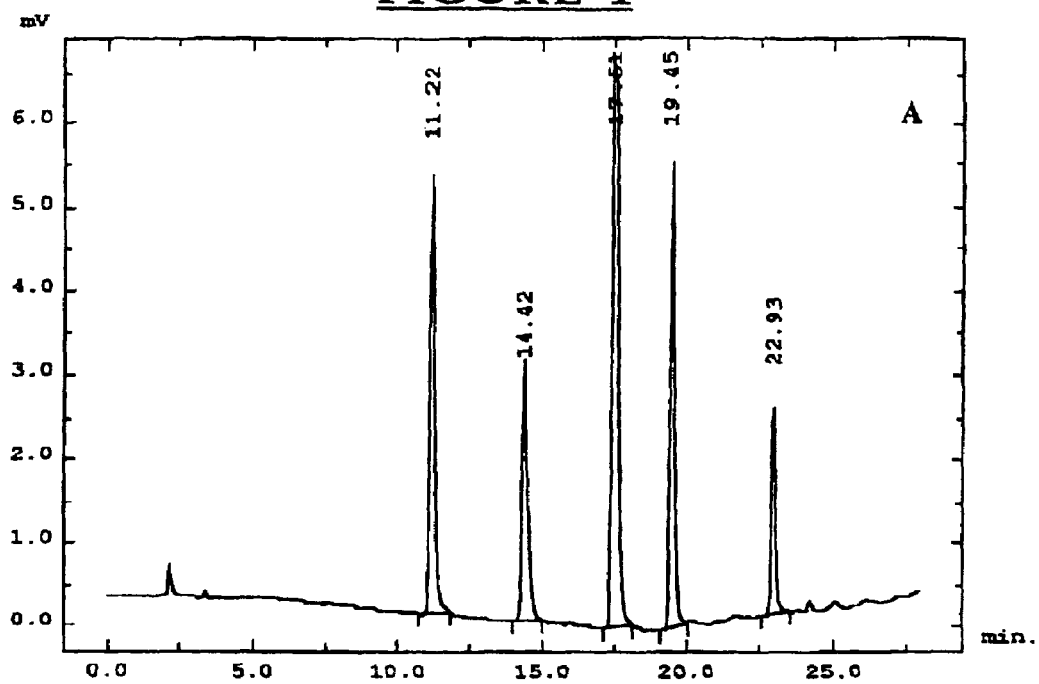
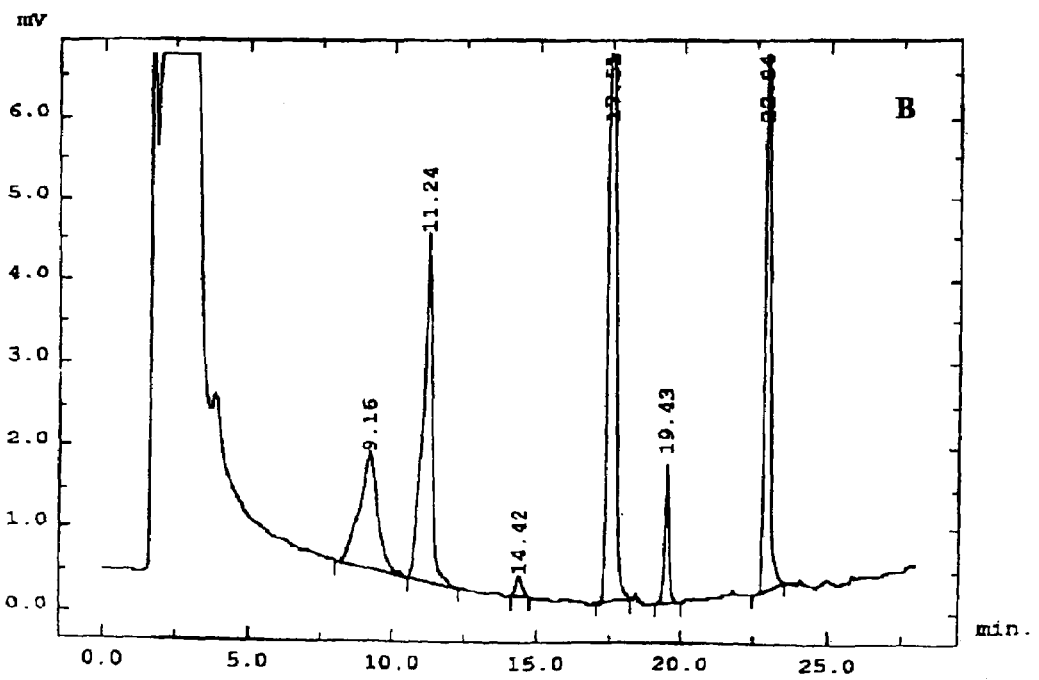

FIGURE 3
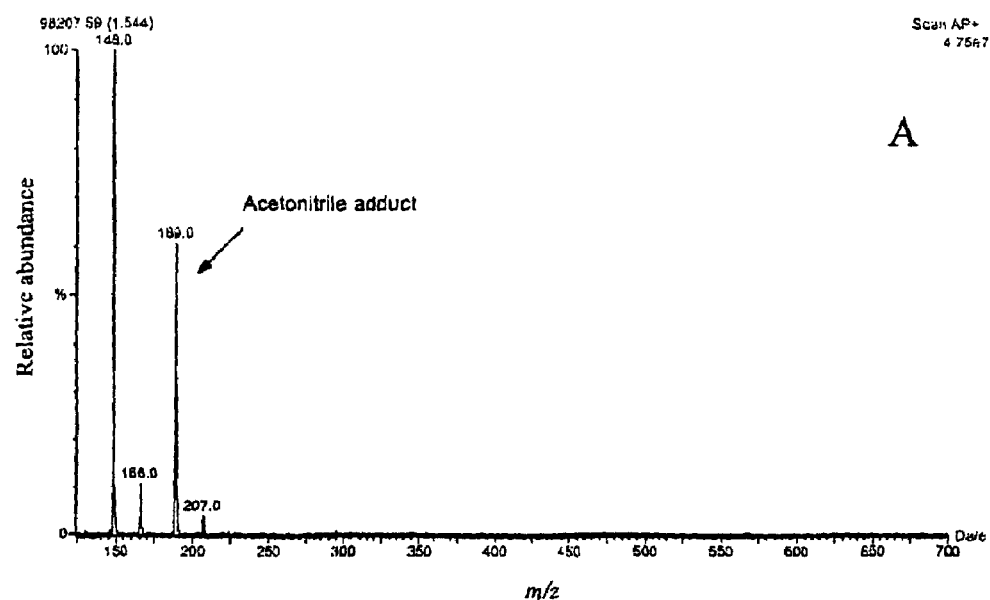
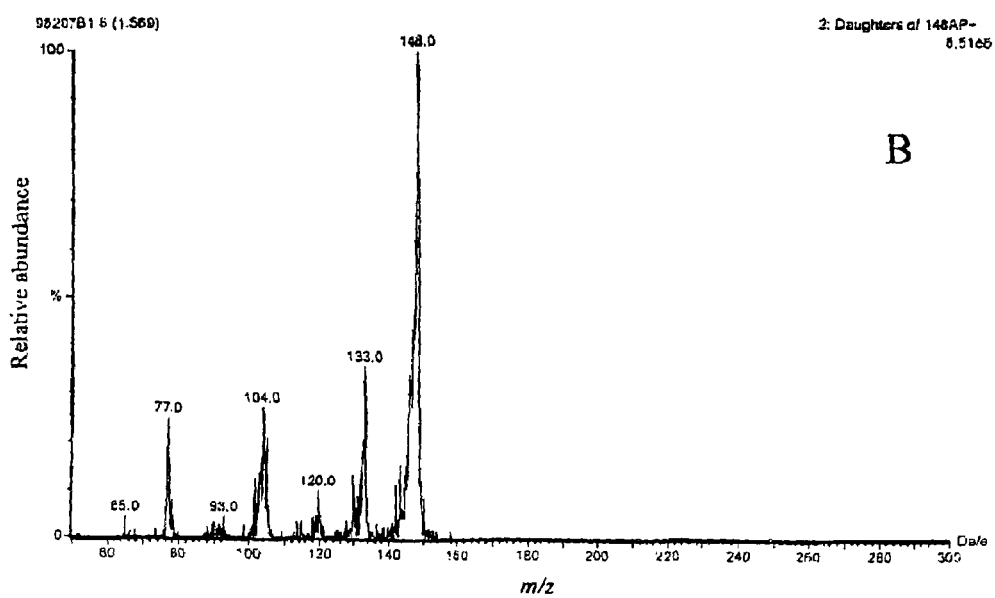

```
2A6   ATG CTG GCC TCA GGC TTG CTT CTC GTG GCT CTG CTG ACC TGC CTG ACC
poly  --- --- --- --- --- --- --- --- --- --- --- --- --- --- --- ---
      Met Leu Ala Ser Gly Leu Leu Leu Val Ala Leu Leu Thr Cys Leu Thr 2A6   ATA ATG GTC TTG ATG TCC GTC TGG CGC CAG AGG AAG CTC CAG GGG AAA
poly  --- --- --- --- --- --- --- --- --- --- --- --- --- --- --- ---
      Ile Met Val Leu Met Ser Val Trp Arg Gln Arg Lys Leu Gln Gly Lys Phe
2A6   CTG CCC CCC GGA CCC ACC CCG CTG CCC TTC ATC GGG AAC TAC CTG CAG
poly  --- --- --- --- --- --- --- --- --- C-- --- --- --- --- --- ---
      Leu Pro Pro Gly Pro Thr Pro Leu Pro Leu Ile Gly Asn Tyr Leu Gln
                                          (124)

2A6   CTG AAC ACG GAG CAG ATG TAC AAC TCC CTC ATG AAG ATC AGC CAG CGC
poly  --- --- --- --- --- --- --- --- --- --- --- --- --- --- --- ---
      Leu Asn Thr Glu Gln Met Tyr Asn Ser Leu Met Lys Ile Ser Gln Arg 2A6   TAT GGC CCT GTG TTC ACC GTC CAC CTG GGG CCC CGG CGG ATA GTG GTG
poly  --- --- --- --- --- --- --- --- --- --- --- --- --- --- --- ---
      Tyr Gly Pro Val Phe Thr Val His Leu Gly Pro Arg Arg Ile Val Val 2A6   CTG TGT GGA TAC GAC GCG GTG AAG GAG GCC CTG GTG GAC CAG GCT GAG
poly  --- --- --- --- --- --- --- --- --- --- --- --- --- --- --- ---
      Leu Cys Gly Tyr Asp Ala Val Lys Glu Ala Leu Val Asp Gln Ala Glu 2A6   GAA TTC AGC GGG CGA GGC GAG CAG GCC ACT TTC GAC TGG CTC TTC AAA
poly  --- --- --- --- --- --- --- --- --- --- --- --- --- --- --- ---
      Glu Phe Ser Gly Arg Gly Glu Gln Ala Thr Phe Asp Trp Leu Phe Lys 2A6   GGC TAT GGC GTG GCC TTC AGC AAC GGC GAG CGT GCC AAG CAG CTC CGG
poly  --- --- --- --- --- --- --- --- --- --- --- --- --- --- --- ---
      Gly Tyr Gly Val Ala Phe Ser Asn Gly Glu Arg Ala Lys Gln Leu Arg Gly Lys Arg Gly
2A6   CGC TTC TCC ATC ACC ACG CTG CGG GAC TTC GGC GTG GGC AAG CGG GGT
poly  --- --- --- --- --- --- --- --- --- --- --- --- GCA AGC GGG GTA
      Arg Phe Ser Ile Thr Thr Leu Arg Asp Phe Gly Val Ala Ser Gly Val
                                                          (422)

Ile Glu Glu Arg Ile Gln Glu Glu Ala Gly His Leu Ile Glu Ala Phe
2A6   ATC GAG GAG CGC ATC CAG GAG GAG GCG GGC CAC CTC ATC GAG GCC TTC
poly  TCG AGG AGC GCA TCC AGG AGG AGG CGG GCT ACC TCA TCG AGG GGT TCC
      Ser Arg Ser Ala Ser Arg Arg Arg Arg Ala Thr Ser Ser Arg Pro Ser Arg Gly Thr Arg Gly Ala Phe Ile Asp Pro Thr Tyr Phe Leu Ser Arg
2A6   CGG GGC ACG CGC GGC GCG TTC ATC GAC CCC ACC TAC TTC CTC AGC CGA
poly  GGG GCA CGC GCG GCG CGT TCA TCG ACC CCA CCT ACT TCC TCA GCC GAA
      Gly Ala Arg Ala Ala Arg Ser Ser Thr Pro Pro Thr Ser Ser Ala Glu Thr Val Ser Asn Val Ile Ser Ser Ile Val Phe Gly Asp Arg Phe Asp
2A6   ACG GTT TCC AAT GTC ATC AGC TCC ATT GTC TTC GGA GAC CGC TTT GAC
poly  CGG TTT CCA ATG TCG TCA GCT CCA TTG TCT TCG GAG ACC GCT TTG ACT
      Arg Phe Pro Met Ser Ser Ala Pro Leu Ser Ser Glu Thr Ala Leu Thr Tyr Glu Asp Lys Glu Phe Leu Ala Leu Leu Arg Met Met Leu Gly Ser
2A6   TAT GAG GAC AAA GAG TTC CTC GCA CTG CTG CGG ATG ATG CTG GGA AGC
poly  ATG AGG ACA AAG AGT TCC TCG CAC TGC TGC GGA TGA (SEQ. ID NO:1)
      Met Arg Thr Lys Ser Ser Ser His Cys Cys Gly STP (SEQ. ID NO:2)
```

*Fig. 11A*

|     |     |     |     |     |     |     |     |     |     |     |     |     |     |
|-----|-----|-----|-----|-----|-----|-----|-----|-----|-----|-----|-----|-----|-----|
|     | Phe | Gln | Phe | Thr | Ala | Thr | Ser | Thr | Gly | Gln | Leu | Tyr | Glu | Met | Phe | Tyr |
| 2A6 | TTT | CAG | TTC | ACA | GCT | ACC | TCT | ACC | GGA | CAG | CTC | TAT | GAG | ATG | TTC | TAC |

|     | Ser | Val | Met | Lys | His | Leu | Pro | Gly | Pro | Gln | Gln | Gln | Ala | Phe | Lys | Asp |
|-----|-----|-----|-----|-----|-----|-----|-----|-----|-----|-----|-----|-----|-----|-----|-----|-----|
| 2A6 | TCG | GTG | ATG | AAA | CAC | CTG | CCA | GGG | CCG | CAG | CAA | CAG | GCA | TTT | AAG | GAC |

|     | Leu | Gln | Gly | Leu | Glu | Asp | Phe | Ile | Ala | Arg | Lys | Val | Glu | His | Asn | Gln |
|-----|-----|-----|-----|-----|-----|-----|-----|-----|-----|-----|-----|-----|-----|-----|-----|-----|
| 2A6 | CTG | CAG | GGG | CTG | GAG | GAC | TTC | ATA | GCC | AGG | AAG | GTG | GAA | CAC | AAC | CAG |

|     | Arg | Thr | Leu | Asp | Pro | Asn | Ser | Pro | Arg | Asp | Phe | Ile | Asp | Ser | Phe | Leu |
|-----|-----|-----|-----|-----|-----|-----|-----|-----|-----|-----|-----|-----|-----|-----|-----|-----|
| 2A6 | CGC | ACG | CTG | GAT | CCC | AAC | TCC | CCG | CGA | GAC | TTC | ATC | GAC | TCC | TTC | CTC |

|     | Ile | Arg | Met | Gln | Glu | Glu | Lys | Lys | Asn | Pro | Asp | Thr | Glu | Phe | Tyr | Trp |
|-----|-----|-----|-----|-----|-----|-----|-----|-----|-----|-----|-----|-----|-----|-----|-----|-----|
| 2A6 | ATC | CGC | ATG | CAG | GAG | GAG | AAG | AAG | AAT | CCT | GAC | ACC | GAG | TTC | TAT | TGG |

|     | Lys | Asn | Leu | Val | Leu | Thr | Thr | Leu | Asn | Leu | Phe | phe | Ala | Gly | Thr | Glu |
|-----|-----|-----|-----|-----|-----|-----|-----|-----|-----|-----|-----|-----|-----|-----|-----|-----|
| 2A6 | AAG | AAC | CTG | GTT | CTG | ACC | ACA | CTG | AAC | CTC | TTC | TTC | GCG | GGC | ACC | GAG |

|     | Thr | Val | Ser | Thr | Thr | Met | Arg | Tyr | Gly | Phe | Leu | Leu | Leu | Met | Lys | His |
|-----|-----|-----|-----|-----|-----|-----|-----|-----|-----|-----|-----|-----|-----|-----|-----|-----|
| 2A6 | ACG | GTC | AGC | ACA | ACG | ATG | CGC | TAC | GGC | TTC | CTG | CTG | CTC | ATG | AAG | CAC |

|     | Pro | Asp | Val | Glu | Ala | Lys | Val | His | Glu | Glu | Ile | Asp | Arg | Val | Ile | Gly |
|-----|-----|-----|-----|-----|-----|-----|-----|-----|-----|-----|-----|-----|-----|-----|-----|-----|
| 2A6 | CCG | GAT | GTG | GAG | GCC | AAA | GTC | CAC | GAG | GAG | ATT | GAC | CGC | GTG | ATC | GGC |

|     | Arg | Asn | Arg | Gln | Ala | Lys | Phe | Glu | Asp | Arg | Ala | Lys | Met | Pro | Tyr | Thr |
|-----|-----|-----|-----|-----|-----|-----|-----|-----|-----|-----|-----|-----|-----|-----|-----|-----|
| 2A6 | AGG | AAC | CGC | CAG | GCC | AAG | TTC | GAG | GAC | CGG | GCC | AAG | ATG | CCC | TAC | ACG |

|     | Glu | Ala | Val | Ile | His | Glu | Ile | Gln | Arg | Phe | Gly | Asp | Met | Ile | Pro | Met |
|-----|-----|-----|-----|-----|-----|-----|-----|-----|-----|-----|-----|-----|-----|-----|-----|-----|
| 2A6 | GAG | GCC | GTG | ATC | CAC | GAG | ATC | CAG | AGA | TTC | GGA | GAC | ATG | ATC | CCC | ATG |

|     | Gly | Leu | Ala | Arg | Arg | Val | Thr | Lys | Asp | Thr | Lys | Phe | Arg | Asp | Phe | Leu |
|-----|-----|-----|-----|-----|-----|-----|-----|-----|-----|-----|-----|-----|-----|-----|-----|-----|
| 2A6 | GGC | CTG | GCC | CGA | AGA | GTC | ACC | AAG | GAT | ACC | AAG | TTT | CGG | GAC | TTC | CTC |

|     | Leu | Pro | Lys | Gly | Thr | Glu | Val | Phe | Pro | Met | Leu | Gly | Ser | Val | Leu | Arg |
|-----|-----|-----|-----|-----|-----|-----|-----|-----|-----|-----|-----|-----|-----|-----|-----|-----|
| 2A6 | CTC | CCC | AAG | GGC | ACT | GAG | GTG | TTC | CCT | ATG | CTG | GGC | TCT | GTG | CTG | AGA |

|     | Asp | Pro | Lys | Phe | Phe | Ser | Asn | Pro | Arg | Gly | Phe | Asn | Pro | Gln | His | Phe |
|-----|-----|-----|-----|-----|-----|-----|-----|-----|-----|-----|-----|-----|-----|-----|-----|-----|
| 2A6 | GAC | CCC | AAG | TTC | TTC | TCC | AAC | CCC | CGA | GGC | TTC | AAC | CCC | CAG | CAC | TTC |

|     | Leu | Asp | Glu | Asn | Gly | Gln | Phe | Lys | Lys | Asn | Asp | Ala | Phe | Val | Pro | Phe |
|-----|-----|-----|-----|-----|-----|-----|-----|-----|-----|-----|-----|-----|-----|-----|-----|-----|
| 2A6 | CTG | GAT | GAG | AAC | GGG | CAG | TTT | AAG | AAG | AAT | GAT | GCT | TTT | GTG | CCC | TTC |

|     | Ser | Ile | Gly | Lys | Arg | Tyr | Cys | Phe | Gly | Glu | Gly | Leu | Ala | Arg | Met | Glu |
|-----|-----|-----|-----|-----|-----|-----|-----|-----|-----|-----|-----|-----|-----|-----|-----|-----|
| 2A6 | TCC | ATC | GGA | AAG | CGG | TAC | TGT | TTC | GGA | GAA | GGT | CTG | GCT | AGA | ATG | GAG |

|     | Leu | Phe | Leu | Phe | Leu | Thr | Asn | Ile | Leu | Gln | Asn | Phe | His | Leu | Lys | Ser |
|-----|-----|-----|-----|-----|-----|-----|-----|-----|-----|-----|-----|-----|-----|-----|-----|-----|
| 2A6 | CTC | TTC | CTC | TTC | CTC | ACC | AAC | ATC | CTG | CAG | AAC | TTC | CAC | CTC | AAG | TCT |

|     | Pro | Gln | Leu | Pro | Gln | Asp | Ile | Asp | Val | Ser | Pro | Lys | His | Val | Gly | Phe |
|-----|-----|-----|-----|-----|-----|-----|-----|-----|-----|-----|-----|-----|-----|-----|-----|-----|
| 2A6 | CCG | CAG | CTG | CCC | CAG | GAC | ATC | GAC | GTG | TCC | CCC | AAA | CAC | GTG | GGC | TTC |

|     | Ala | Thr | Ile | Pro | Pro | Thr | Tyr | Thr | Met | Ser | Phe | Leu | Pro | Arg | STP |
|-----|-----|-----|-----|-----|-----|-----|-----|-----|-----|-----|-----|-----|-----|-----|-----|
|     |     |     |     |     |     |     |     |     |     |     |     |     |     |     | (SEQ. ID NO:4) |
| 2A6 | GCC | ACC | ATC | CCC | CCG | ACC | TAC | ACC | ATG | AGC | TTC | CTG | CCC | CGC | TGA |
|     |     |     |     |     |     |     |     |     |     |     |     |     |     |     | (SEQ. ID NO:3) |

*Fig. 11B*

```
                                    ACGCGGGGAACTGACCGTCCCTCGCAGTGCCACC   34
ATGCTGGCCTCAGGCTTGCTTCTCGTGGCTCTGCTGACCTGCCTGACCATAATGGTCTTGATGTCCGTCTGGCGCCAGAGG  115
 M  L  A  S  G  L  L  L  V  A  L  L  T  C  L  T  I  M  V  L  M  S  V  W  R  Q  R   27
AAGCTCCAGGGGAAACTGCCCCCCGGACCCACCCCGCTGCCCTTCATCGGGAACTACCTGCAGCTGAACACGGAGCAGATG  196
 K  L  Q  G  K  L  P  P  G  P  T  P  L  P  F  I  G  N  Y  L  Q  L  N  T  E  Q  M   54
TACAACTCCCTCATGAAGATCAGCCAGCGCTATGGCCCTGTGTTCACCGTCCACCTGGGGCCCCGGCGGATAGTGGTGCTG  277
 Y  N  S  L  M  K  I  S  Q  R  Y  G  P  V  F  T  V  H  L  G  P  R  R  I  V  V  L   81
TGTGGATACGACGCGGTGAAGGAGGCCCTGGTGGACCAGGCTGAGGAATTCAGCGGGCGAGGCGAGCAGGCCACTTTCGAC  358
 C  G  Y  D  A  V  K  E  A  L  V  D  Q  A  E  E  F  S  G  R  G  E  Q  A  T  F  D   108
TGGCTCTTCAAAGGCTATGGCGTGGCCTTCAGCAACGGCGAGCGTGCCAAGCAGCTCCGGCGCTTCTCCATCACCACGCTG  439
 W  L  F  K  G  Y  G  V  A  F  S  N  G  E  R  A  K  Q  L  R  R  F  S  I  T  T  L   135
CGGGACTTCGGCGTGGGCAAGCGGGGTATCGAGGAGCGCATCCAGGAGGAGGCGGGCCACCTCATCGAGGCCTTCCGGGGC  520
 R  D  F  G  V  G  K  R  G  I  E  E  R  I  Q  E  E  A  G  H  L  I  E  A  F  R  G   162
ACGCGCGGCGCGTTCATCGACCCCACCTACTTCCTCAGCCGAACGGTTTCCAATGTCATCAGCTCCATTGTCTTCGGAGAC  601
 T  R  G  A  F  I  D  P  T  Y  F  L  S  R  T  V  S  N  V  I  S  S  I  V  F  G  D   189
CGCTTTGACTATGAGGACAAAGAGTTCCTCGCACTGCTGCGGATGATGCTGGGAAGCTTTCAGTTCACAGCTACCTCTACC  682
 R  F  D  Y  E  D  K  E  F  L  A  L  L  R  M  M  L  G  S  F  Q  F  T  A  T  S  T   216
GGACAGCTCTATGAGATGTTCTACTCGGTGATGAAACACCTGCCAGGGCCGCAGCAACAGGCATTTAAGGACCTGCAGGGG  763
 G  Q  L  Y  E  M  F  Y  S  V  M  K  H  L  P  G  P  Q  Q  Q  A  F  K  D  L  Q  G   243
CTGGAGGACTTCATAGCCAGGAAGGTGGAACACAACCAGCGCACGCTGGATCCCAACTCCCCGCGAGACTTCATCGACTCC  844
 L  E  D  F  I  A  R  K  V  E  H  N  Q  R  T  L  D  P  N  S  P  R  D  F  I  D  S   270
TTCCTCATCCGCATGCAGGAGGAGAAGAAGAATCCTGACACCGAGTTCTATTGGAAGAACCTGGTTCTGACCACACTGAAC  925
 F  L  I  R  M  Q  E  E  K  K  N  P  D  T  E  F  Y  W  K  N  L  V  L  T  T  L  N   297
CTCTTCTTCGCGGGCACCGAGACGGTCAGCACAACGATGCGCTACGGCTTCCTGCTGCTGATGAAGCACCCGGATGTGGAG  1006
 L  F  F  A  G  T  E  T  V  S  T  T  M  R  Y  G  F  L  L  L  M  K  H  P  D  V  E   324
GCCAAAGTCCACGAGGAGATTGACCGCGTGATCGGCAGGAACCGCCAGGCCAAGTTCGAGGACCGGGCCAAGATGCCCTAC  1087
 A  K  V  H  E  E  I  D  R  V  I  G  R  N  R  Q  A  K  F  E  D  R  A  K  M  P  Y   351
ACGGAGGCCGTGATCCACGAGATCCAGAGATTCGGAGACATGATCCCCATGGGCCTGGCCCGAAGAGTCACCAAGGATACC  1168
 T  E  A  V  I  H  E  I  Q  R  F  G  D  M  I  P  M  G  L  A  R  R  V  T  K  D  T   378
AAGTTTCGGGACTTCCTCCTCCCCAAGGGCACTGAGGTGTTCCCTATGCTGGGCTCTGTGCTGAGAGACCCCAAGTTCTTC  1249
 K  F  R  D  F  L  L  P  K  G  T  E  V  F  P  M  L  G  S  V  L  R  D  P  K  F  F   405
TCCAACCCCCGAGGCTTCAACCCCCAGCACTTCCTGGATGAGAACGGGCAGTTTAAGAAGAATGATGCTTTTGTGCCCTTC  1330
 S  N  P  R  G  F  N  P  Q  H  F  L  D  E  N  G  Q  F  K  K  N  D  A  F  V  P  F   432
TCCATCGGAAAGCGGTACTGTTTCGGAGAAGGTCTGGCTAGAATGGAGCTCTTCCTCTTCCTCACCAACATCCTGCAGAAC  1411
 S  I  G  K  R  Y  C  F  G  E  G  L  A  R  M  E  L  F  L  F  L  T  N  I  L  Q  N   459
TTCCACCTCAAGTCTCCGCAGCTGCCCCAGGACATCGACGTGTCCCCCAAACACGTGGGCTTCGCCACCATCCCCCCGACC  1492
 F  H  L  K  S  P  Q  L  P  Q  D  I  D  V  S  P  K  H  V  G  F  A  T  I  P  P  T   489
TACACCATGAGCTTCCTGCCCCGCTGA        (SEQ ID NO:18)
1519
 Y  T  M  S  F  L  P  R STP         (SEQ ID NO:19)
```

Fig. 12

```
human2A6  101   RGEQATFDWV FKGYGVVFSN GERAKQLRRF SIATLRDFGV GKRGIEERIQ EEAGFLIDAL RGTGGANIDP
human2A3  101   RGEQATFDWV FKGYGVVFSN GERAKQLRRF SIATLRDFGV GKRGIEERIQ EEAGFLIDAL RGTGGANIDP
pig2A6    101   RGEQATFDWL FKGYGVAFSN GERAKQLRRF SITTLRDFGV GKRGIEERIQ EEAGHLIEAF RGTRGAFIDP
                          * human2a6  171   TFFLSRTVSN VISSIVFGDR FDYKDKEFLS LLRMMLGIFQ FTSTSTGQLY EMFSSVMKHL PGPQQQAFQL
human2a3  171   TFFLSRTVSN VISSIVFGDR FDYKDKEFLS LLRMMLGIFQ FTSTSTGQLY EMFSSVMKHL PGPQQQAFQL
pig2a6    171   TYFLSRTVSN VISSIVFGDR FDYEDKEFLA LLRMMLGSFQ FTATSTGQLY EMFYSVMKHL PGPQQQAFKD
                                                            * human2a6  241   LQGLEDFIAK KVEHNQRTLD PNSPRDFIDS FLIRMQEEEK NPNTEFYLKN LVMTTLNLFI GGTETVSTTL
human2a3  241   LQGLEDFIAK KVEHNQRTLD PNSPRDFIDS FLIRMQEEEK NPNTEFYLKN LVMTTLNLFI GGTETVSTTL
pig2a6    241   LQGLEDFIAR KVEHNQRTLD PNSPRDFIDS FLIRMQEEKK NPDTEFYWKN LVLTTLNLFF AGTETVSTTM human2a6  311   RYGFLLLMKH PEVEAKVHEE IDRVIGKNRQ PKFEDRAKMP YMEAVIHEIQ RFGDVIPMSL ARRVKKDTKF
human2a3  311   RYGFLLLMKH PEVEAKVHEE IDRVIGKNRQ PKFEDRAKMP YMEAVIHEIQ RFGDVIPMSL ARRVKKDTKF
pig2a6    311   RYGFLLLMKH PDVEAKVHEE IDRVIGRNRQ AKFEDRAKMP YTEAVIHEIQ RFGDMIPMGL ARRVTKDTKF human2a6  381   RDFFLPKGTE VFPMLGSVLR DPSFFSNPQD FNPQHFLNEK GQFKKSDAFV PFSIGKRNCF GEGLARMELF
human2a3  381   RDFFLPKGTE VYPMLGSVLR DPSFFSNPQD FNPQHFLNEK GQFKKSDAFV PFSIGKRNCF GEGLARMELF
pig2a6    381   RDFLLPKGTE VFPMLGSVLR DPKFFSNPRG FNPQHFLDEN GQFKKNDAFV PFSIGKRYCF GEGLARMELF human2a6  451   LFFTTVMQNF RLKSSQSPKD IDVSPKHVGF IDVSPKHVGF  (SEQ ID NO:20)
human2a3  451   LFFTTVMQNF RLKSSQSPKD IDVSPKHVGF IDVSPKHVGF  (SEQ ID NO:21)
pig2a6    451   LFLTNILQNF HLKSPQLPQD IDVSPKHVGF IDVSPKHVGF  (SEQ ID NO:22)
                    *
```

Fig. 13

GENETIC MARKERS FOR SKATOLE METABOLISM

CROSS-REFERENCE TO RELATED APPLICATIONS

This application claims benefit from U.S. application Ser. No. 10/206,118 filed Jul. 29 2002, which is a divisional of U.S. application Ser. No. 09/672,039, filed Sep. 29, 2000 now U.S. Pat. No. 6,448,028 which is a continuation of U.S. provisional application No. 60/156,935, filed Sep. 30, 1999 all of which are incorporated herein by reference.

FIELD OF THE INVENTION

The present invention relates to novel metabolites of skatole and the identification of novel enzymes involved in the metabolism of skatole. The invention has utility in developing methods to identify and reduce boar taint.

BACKGROUND OF THE INVENTION

Male pigs that are raised for meat production are usually castrated shortly after birth to prevent the development of off-odors and off flavors (boar taint) in the carcass. Boar taint is primarily due to high levels of either the 16-androstene steroids (especially 5α(-androst-16-en-3-one)) or skatole in the fat. Recent results of the EU research program AIR 3-PL94-2482 suggest that skatole contributes more to boar taint than androstenone (Bonneau, M., 1997).

Skatole is produced by bacteria in the hindgut which degrade tryptophan that is available from undigested feed or from the turnover of cells lining the gut of the pig (Jensen and Jensen, 1995). Skatole is absorbed from the gut and metabolized primarily in the liver (Jensen and Jensen, 1995). High levels of skatole can accumulate in the fat, particularly in male pig, and the presence of a recessive gene Ska.sup.1, which results in decreased metabolism and clearance of skatole has been proposed (Lundström et al., 1994; Friis, 1995). Skatole metabolism has been studied extensively in ruminants (Smith, et al., 1993), where it can be produced in large amounts by ruminal bacteria and results in toxic effects on the lungs (reviewed in Yost, 1989). The metabolic pathways involving skatole have not been well described in pigs. In particular, the reasons why only some intact male pigs have high concentrations of skatole in the fat are not clear. Environmental and dietary factors are important (Kjeldsen, 1993; Hansen et al., 1995) but do not sufficiently explain the reasons for the variation in fat skatole concentrations in pigs. Claus et al. (1994) proposed high fat skatole concentrations are a result of an increased intestinal skatole production due to the action of androgens and glucocorticoids. Lundström et al. (1994) reported a genetic influence on the concentrations of skatole in the fat, which may be due to the genetic control of the enzymatic clearance of skatole. The liver is the primary site of metabolism of skatole and liver enzymatic activities could be the controlling factor of skatole deposition in the fat. B.ae butted.k et al. (1995) described several liver metabolites of skatole found in blood and urine with the major being MII and MIII. MII, which is a sulfate conjugate of 6-hydroxyskatole (pro-MII), was only found in high concentrations in plasma of pigs which were able to rapidly clear skatole from the body, whereas high MIII concentrations were related to slow clearance of skatole. Thus the capability of synthesis of MII could be a major step in a rapid metabolic clearance of skatole resulting in low concentrations of skatole in fat and consequently low levels of boar taint.

In view of the foregoing, further work is needed to fully understand the metabolism of skatole in pig liver and to identify the key enzymes involved. Understanding the biochemical events involved in skatole metabolism can lead to novel strategies for treating, reducing or preventing boar taint. In addition, polymorphisms in these candidate genes may be useful as possible markers for low boar taint pigs.

SUMMARY OF THE INVENTION

The present inventors have identified novel metabolites resulting from the phase I metabolism of skatole (3-methylindole, 3MI) by porcine liver microsomes. The metabolites identified are: 3-OH-3-methylindolenine (HMI); 3-methyloxindole (3MOI); indole-3-carbinol (I-3C); and 2-aminoacetophenone (2-AM). Measuring levels of these metabolites in a pig may be useful in identifying the pig's ability to metabolize skatole and hence its susceptibility to boar taint.

The present inventors have also determined that one of the metabolites of skatole, HMI is metabolized to 3-hydroxy-3-methyloxindole (HMOI) by aldehyde oxidase. As a result, enhancing the activity of the aldehyde oxidase may be useful in enhancing skatole metabolism and reducing boar taint. Accordingly, the present invention provides a method for enhancing the metabolism of 3-methylindole and thereby reducing boar taint comprising enhancing the activity of aldehyde oxidase in a pig. The activity of aldehyde oxidase can be enhanced by using substances which (a) increase the activity of aldehyde oxidase; or (b) induce or increase the expression of the aldehyde oxidase gene.

The present inventors have further determined that the cytochrome P450 enzyme, CYP2A6, is also involved in the metabolism of skatole by porcine liver microsomes. As a result, enhancing the activity of the CYP2A6 may be useful in enhancing skatole metabolism and reducing boar taint. Accordingly, the present invention provides a method for enhancing the metabolism of 3-methylindole and thereby reducing boar taint comprising enhancing the activity of CYP2A6 in a pig. The activity of CYP2A6 can be enhanced by using substances which (a) increase the activity of CYP2A6; or (b) induce or increase the expression of the CYP2A6 gene.

The identification of enzymes involved in the metabolism of skatole allows the development of screening assays for substances that interact with these enzymes in skatole metabolism. The screening assays can be used to identify substances that can be used to reduce or treat boar taint.

The present invention also includes a method for producing pigs that have a lower incidence of boar taint by selecting pigs that have high levels of aldehyde oxidase and/or CYP2A6 and breeding the selected pigs.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 1 is a chromatographic profile of the main five metabolites produced by pig liver microsomes as detected by UV absorption at 250 nm. Retention times correspond as follows: 9.16 min, UV-1; 11.24 min, 3-hydroxy-3-methyloxindole; 14.42 min, indole-3-carbinol; 17.51 min, 3-methyloxindole; 19.43 min, 2-aminoacetophenone; 22.84 min, parent compound (3-methylindole). (A) Standard mixture containing 2 µg/ml of each metabolite. (B) Incubation mixture.

FIG. 3A is an LC-MS spectrum of metabolite UV-1.

FIG. 3B is an MS/MS spectrum of daughter ion of m/z 148.

FIG. 11 shows the sequence alignment of the CYP2A6 gene (SEQ ID NO:3) and the mutation (SEQ ID NO:1), at nt position 1220, indicated in bold.

FIG. 12 shows the nucleotides sequence and deduced amino acid sequences for the pig cytochrome P450 2A6 cDNA from the liver. CYP2A6 was isolated from a pig cDNA library. (SEQ ID NOS: 18 and 19) The nucleotide sequence has been registered in the GenBank (accession number, AY091516). The deduced amino acid sequence is indicated below the corresponding nucleotide sequence. Three active sites for CYP2A6 are underlined. The numbers of nucleotides and amino acids are indicated in the right.

FIG. 13 shows the alignment of amino acid sequence of human CYP2A6 (SEQ ID NO: 20), CYP2A3 (SEQ ID NO: 21) and pig 2A6 (SEQ ID NO: 22). Gln104, Phe209 and His477 are reported to be active site for human CYP2A6 coumarin 7-hydroxylase activity, oxidative metabolism of nicotine and cotinine. The numbers of amino acids are indicated in the right. Asterisk indicated identical for these active site between human and pig.

DETAILED DESCRIPTION OF THE INVENTION

I. Skatole Metabolites

Figure 2:
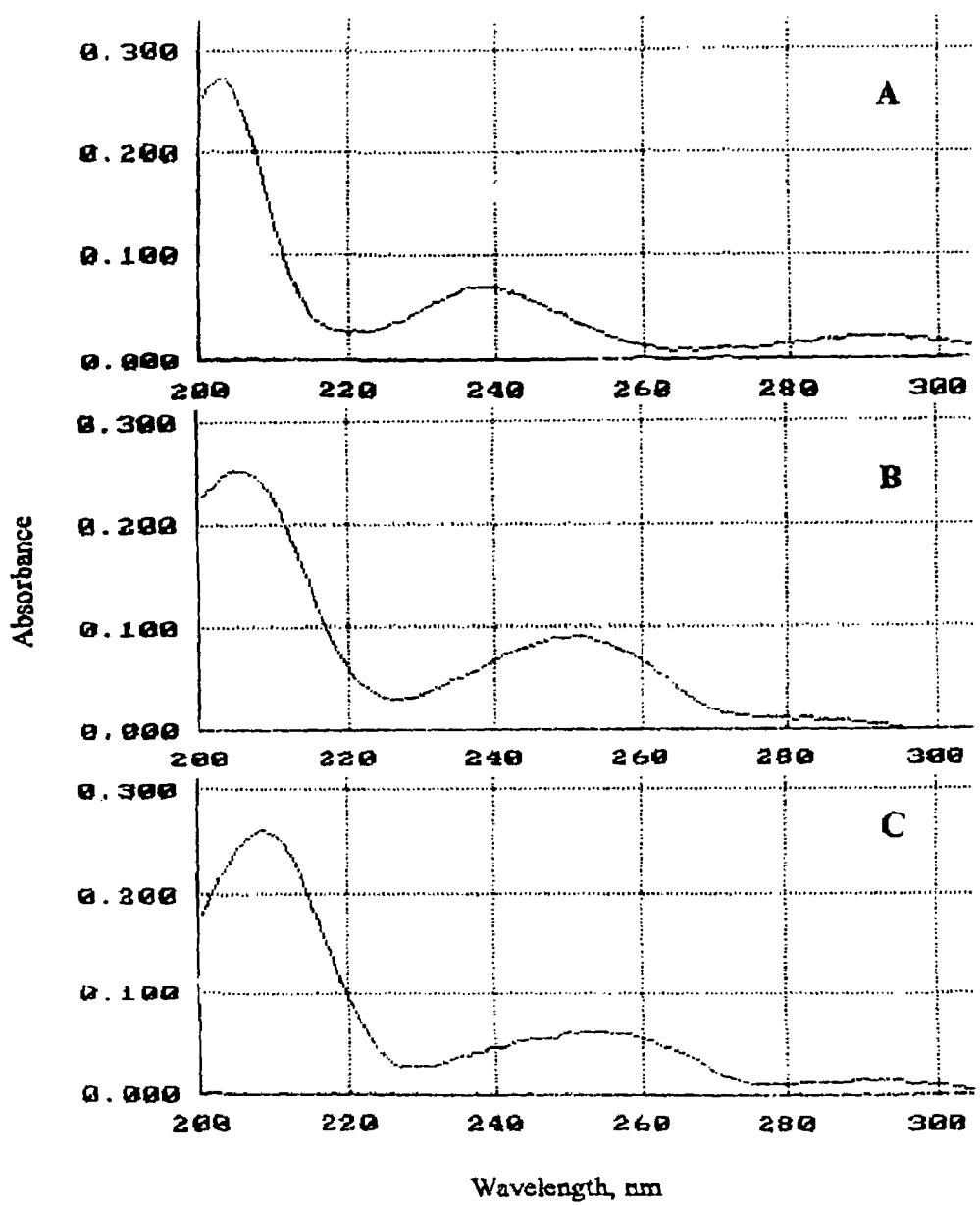
FIG. 2 is a UV spectra of (A) UV-1 metabolite [$\lambda_{max}$ (nm): 204, 238]; (B) 3-methyloxindole[$\lambda_{max}$ (nm): 205, 252]; and (C) 3-hydroxy-3-methyloxindole[HMOI: [$\lambda_{max}$ (nm): 208, 253].

The present inventors have identified novel metabolites resulting from the phase I metabolism of skatole (3-methyl indole, 3MI) by porcine liver microsomes. The metabolites identified are: 3-OH-3-methylindolenine (HMI); 3-methyloxindole (3MOI); indole-3-carbinol (I-3C); and 2-aminoacetophenone (2-AM).

Measuring levels of these metabolites in a pig may be useful in identifying the pig's ability to metabolize skatole and its susceptibility to boar taint. Accordingly, the present invention provides a method of assessing a pig's ability to metabolize 3-methyl indole comprising testing a sample from the pig for one or more metabolites selected from the group consisting of 3-OH-3-methylindolenine (HMI); 3-methyloxindole (3MOI); indole-3-carbinol (I-3C); and 2-aminoacetophenone.

Since skatole metabolites also undergo Phase II sulfation and glucuronidation reactions, the assay may include measuring the sulfation or glucuronidation products of the metabolites. The sample can be any biological sample from the pig, preferably liver, plasma or fat. Measuring levels of particular metabolites can be used to classify pigs as either good or poor skatole metabolizers. Poor skatole metabolism may be causative of boar taint and therefore the assay may be useful in identifying pigs with boar taint or at risk for developing poor taint. Pigs that have a reduced risk for boar taint (i.e., good metabolizers) may be further selected and bred to produce low boar taint pigs.

II. Enzymes a) Aldehyde Oxidase

The present inventors have determined that one of the metabolites of skatole, HMI is metabolized to 3-hydroxy-3-methyloxindole (HMOI) by aldehyde oxidase, a cytosolic metalloflavoprotein. The inventors have also determined that aldehyde oxidase plays an important role in the metabolism of skatole (or 3MI) and that its catalytic activity is related to adequate 3MI clearance. As a result, enhancing the activity of the aldehyde oxidase may be useful in enhancing skatole metabolism and reducing boar taint. Accordingly, the present invention provides a method for enhancing the metabolism of 3-methylindole comprising enhancing the activity of aldehyde oxidase in a pig. The activity of aldehyde oxidase can be enhanced by using substances which (a) increase the activity of aldehyde oxidase; or (b) induce or increase the expression of the aldehyde oxidase gene. The activity of aldehyde oxidase may also be enhanced using gene therapy whereby a nucleic acid sequence encoding an dehyde oxidase enzyme in introduced into a pig either ex-vivo or in-vivo. A nucleic acid sequence encoding aldehyde oxidase may be obtained by cloning the pig gene using the information available from the human, bovine and rabbit genes.

As mentioned above, aldehyde oxidase activity is related to 3MI clearance. As a result, testing the enzymatic activity of aldehyde oxidase in a pig can be used to determine a pig's susceptibility to boar taint. Pigs with high aldehyde oxidase activity would be at a lower risk for boar taint than pigs with a low aldehyde oxidase activity. Pigs with high aldehyde oxidase activity may be selected and bred to produce low boar taint pigs. Accordingly, the present invention provides a method of determining a pig's susceptibility to boar taint comprising determining the activity of aldehyde oxidase in a sample from a pig. Methods for determining aldehyde oxidase activity are detailed in Example 2.

b) CYP2A6

The present inventors have further determined that the cytochrome P450 enzyme, CYP2A6, is also involved in the metabolism of skatole by porcine liver microsomes. As a result, enhancing the activity of CYP2A6 may be useful in enhancing skatole metabolism and reducing boar taint. Accordingly, the present invention provides a method for enhancing the metabolism of 3-methylindole comprising enhancing the activity of CYP2A6 in a pig. The activity of CYP2A6 can be enhanced by using substances which (a) increase the activity of CYP2A6; or (b) induce or increase the expression of the CYP2A6 gene. The activity of CYP2A6 may also be enhanced using gene therapy whereby a nucleic acid sequence encoding a CYP2A6 enzyme in introduced into a pig either ex-vivo or in-vivo. A nucleic acid sequence encoding CYP2A6 may be obtained by cloning the pig gene using the information available from the human gene.

Testing the enzymatic activity of CYP2A6 in a pig can be used to determine a pig's susceptibility to boar taint. Pigs with high CYP2A6 activity would be at a lower risk for boar taint than pigs with a low CYP2A6 activity. Pigs with high CYP2A6 activity may be selected and bred to produce low boar taint pigs. Accordingly, the present invention provides a method of determining a pig's susceptibility to boar taint comprising determining the activity of CYP2A6 in a sample from a pig.

c) Screening Assays

The identification of enzymes involved in the metabolism of skatole allows the development of screening assays for substances that interact with these enzymes and thereby modulate skatole metabolism.

In one aspect, the present invention provides a method of screening for a substance that enhances the activity of aldehyde oxidase or CYP2A6.

In one embodiment of the invention, a method is provided for screening for a substance that enhances skatole metabolism in a pig by enhancing aldehyde oxidase activity comprising the steps of:

(a) reacting a substrate of aldehyde oxidase and aldehyde oxidase, in the presence of a test substance, under conditions such that aldehyde oxidase is capable of converting the substrate into a reaction product;

(b) assaying for reaction product, unreacted substrate or unreacted aldehyde oxidase;

(c) comparing to controls to determine if the test substance selectively enhances aldehyde oxidase activity and thereby is capable of enhancing skatole metabolism in a pig. Substrates of aldehyde oxidase which may be used in the method of the invention include HMI which is metabolized to HMOI.

The induction of aldehyde oxidase activity can be measured using a variety of techniques including measuring the levels of the aldehyde oxidase protein or mRNA or by testing for aldehyde oxidase activity. Aldehyde oxidase activity can be measured using various assays including the assay described in Example 2 and those described by Rajagopalan et al., 1966.

In another embodiment of the invention, a method is provided for screening for a substance that enhances skatole metabolism in a pig by enhancing CYP2A6 activity comprising the steps of:

(a) reacting a substrate of CYP2A6 and CYP2A6, in the presence of a test substance, under conditions such that CYP2A6 is capable of converting the substrate into a reaction product;

(b) assaying for reaction product, unreacted substrate or unreacted CYP2A6;

(c) comparing to controls to determine if the test substance selectively enhances CYP2A6 activity and thereby is capable of enhancing skatole metabolism in a pig.

Substrates of CYP2A6 which may be used in the method of the invention for example include skatole and coumarin.

The induction of CYP2A6 activity can be measured using a variety of techniques including measuring the levels of the CYP2A6 protein or mRNA or by testing for CYP2A6 activity as described in Aitio, 1978.

The aldehyde oxidase and CYP2A6 enzymes used in the method of the invention may be obtained from natural, recombinant, or commercial sources. Cells or liver microsomes expressing the enzymes may also be used in the method.

Conditions which permit the formation of a reaction product may be selected having regard to factors such as the nature and amounts of the test substance and the substrate.

The reaction product, unreacted substrate, or unreacted enzyme; may be isolated by conventional isolation techniques, for example, salting out, chromatography, electrophoresis, gel filtration, fractionation, absorption, polyacrylamide gel electrophoresis, agglutination, or combinations thereof.

To facilitate the assay of the reaction product, unreacted substrate, or unreacted enzyme; antibody against the reaction product or the substance, or a labeled enzyme or substrate, or a labeled substance may be utilized. Antibodies, enzyme, substrate, or the substance may be labeled with a detectable marker such as a radioactive label, antigens that are recognized by a specific labeled antibody, fluorescent compounds, enzymes, antibodies specific for a labeled antigen, and chemiluminescent compounds.

The substrate used in the method of the invention may be insolubilized. For example, it may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc. The insolubilized enzyme, substrate, or substance may be prepared by reacting the material with a suitable insoluble carrier using known chemical or physical methods, for example, cyanogen bromide coupling.

In another aspect, the present invention includes a method for screening for a substance that enhances skatole metabolism by modulating the transcription or translation of an enzyme involved in skatole metabolism.

In one embodiment of the invention, a method is provided for screening for a substance that enhances skatole metabolism by enhancing transcription and/or translation of the gene encoding aldehyde oxidase comprising the steps of:

(a) culturing a host cell comprising a nucleic acid molecule containing a nucleic acid sequence encoding aldehyde oxidase and the necessary elements for the transcription or translation of the nucleic acid sequence, and optionally a reporter gene, in the presence of a test substance; and (b) comparing the level of expression of aldehyde oxidase, or the expression of the protein encoded by the reporter gene with a control cell transfected with a nucleic acid molecule in the absence of the test substance.

In another embodiment of the invention, a method is provided for screening for a substance that enhances skatole metabolism by enhancing transcription and/or translation of the gene encoding CYP2A6 comprising the steps of:

(a) culturing a host cell comprising a nucleic acid molecule containing a nucleic acid sequence encoding CYP2A6 and the necessary elements for the transcription or translation of the nucleic acid sequence, and optionally a reporter gene, in the presence of a test substance; and (b) comparing the level of expression of CYP2A6, or the expression of the protein encoded by the reporter gene with a control cell transfected with a nucleic acid molecule in the absence of the test substance.

A host cell for use in the method of the invention may be prepared by transfecting a suitable host with a nucleic acid molecule comprising a nucleic acid sequence encoding the appropriate enzyme. Suitable transcription and translation elements may be derived from a variety of sources, including bacterial, fungal, viral, mammalian, or insect genes. Selection of appropriate transcription and translation elements is dependent on the host cell chosen, and may be readily accomplished by one of ordinary skill in the art. Examples of such elements include: a transcriptional promoter and enhancer or RNA polymerase binding sequence, a ribosomal binding sequence, including a translation initiation signal. Additionally, depending on the host cell chosen and the vector employed, other genetic elements, such as an origin of replication, additional DNA restriction sites, enhancers, and sequences conferring inducibility of transcription may be incorporated into the expression vector. It will also be appreciated that the necessary transcription and translation elements may be supplied by the native gene of the enzyme and/or its flanking sequences.

Examples of reporter genes are genes encoding a protein such as green fluorescence protein, β-galactosidase, chloramphenicol acetyltransferase, firefly luciferase, or an immunoglobulin or portion thereof such as the Fc portion of an immunoglobulin, preferably IgG. Transcription of the reporter gene is monitored by changes in the concentration of the reporter protein such as β-galactosidase, chloramphenicol acetyltransferase, or firefly luciferase. This makes it possible to visualize and assay for expression of the enzyme and in particular to determine the effect of a substance on expression of enzyme.

Suitable host cells include a wide variety of prokaryotic and eukaryotic host cells, including bacterial, mammalian, yeast or other fungi, viral, plant, or insect cells. Protocols for the transfection of host cells are well known in the art (see, Sambrook et al. Molecular Cloning A Laboratory Manual, 2nd edition, Cold Spring Harbor Laboratory Press, 1989, which is incorporated herein by reference). Host cells which are commercially available may also be used in the method of the invention. For example, the h2A3 and h2B6 cell lines available from Gentest Corporation are suitable for the screening methods of the invention.

Substances which enhance skatole metabolism by enhancing aldehyde oxidase or CYP2A6 activity (including the substances isolated by the above screening methods) may be used to reduce or treat boar taint or to prepare medicaments to reduce or treat boar taint.

d) Compositions

Substances which enhance skatole metabolism (including substances identified using the methods of the invention which selectively enhance aldehyde oxidase or CYP2A6 activity) may be incorporated into pharmaceutical compositions. Therefore, the invention provides a pharmaceutical composition for use in reducing boar taint comprising an effective amount of one or more substances which enhance skatole metabolism and a pharmaceutically acceptable carrier, diluent, or excipient. The term "effective amount" as used herein means an amount effective, at dosages and for periods of time necessary to achieve the desired result.

In one embodiment, the present invention provides a pharmaceutical composition comprising an effective amount of a substance which is selected from the group consisting of (a) a substance that increases the activity of an aldehyde oxidase enzyme;

(b) a substance that induces or increases the expression of an aldehyde oxidase gene;

(c) a substance that increases the activity of an CYP2A6 enzyme; and (d) a substance that induces or increases the expression of an CYP2A6 gene.

The substances for the present invention can be administered for oral, topical, rectal, parenteral, local, inhalant or intracerebral use. Preferably, the active substances are administered orally (in the food or drink) or as an injectable formulation.

In the methods of the present invention, the substances described in detail herein and identified using the method of the invention form the active ingredient, and are typically administered in admixture with suitable pharmaceutical diluents, excipients, or carriers suitably selected with respect to the intended form of administration, that is, oral tablets, capsules, elixirs, syrups and the like, consistent with conventional veterinary practices.

For example, for oral administration the active ingredients may be prepared in the form of a tablet or capsule for inclusion in the food or drink. In such a case, the active substances can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral active substances can be combined with any oral, non-toxic, pharmaceutically acceptable inert carrier such as ethanol, glycerol, water, and the like. Suitable binders, lubricants, disintegrating agents, and coloring agents can also be incorporated into the dosage form if desired or necessary. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Suitable lubricants used in these dosage forms include sodium oleate, sodium stearate, magnesium stearate, sodium benzoate, sodium acetate, sodium chloride, and the like. Examples of disintegrators include starch, methyl cellulose, agar, bentonite, xanthan gum, and the like.

Gelatin capsules may contain the active substance and powdered carriers, such as lactose, starch, cellulose derivatives, magnesium stearate, stearic acid, and the like. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract. Liquid dosage forms for oral administration may contain coloring and flavoring agents to increase acceptance.

Water, a suitable oil, saline, aqueous dextrose, and related sugar solutions and glycols such as propylene glycol or polyethylene glycols, may be used as carriers for parenteral solutions. Such solutions also preferably contain a water soluble salt of the active ingredient, suitable stabilizing agents, and if necessary, buffer substances. Suitable stabilizing agents include antioxidizing agents such as sodium bisulfate, sodium sulfite, or ascorbic acid, either alone or combined, citric acid and its salts and sodium EDTA. Parenteral solutions may also contain preservatives, such as benzalkonium chloride, methyl- or propyl-paraben, and chlorobutanol.

The substances described in detail herein and identified using the methods of the invention can also be administered in the form of liposome delivery systems, such as small unilamellar vesicles, large unilamellar vesicles, and multi-lamellar vesicles. Liposomes can be formed from a variety of phospholipids, such as cholesterol, stearylamine, or phosphatidylcholines.

Substances described in detail herein and identified using the methods of the invention may also be coupled with soluble polymers which are targetable drug carriers. Examples of such polymers include polyvinylpyrrolidone, pyran copolymer, polyhydroxypropyl-methacrylamidephenol, polyhydroxyethyl-aspartamidephenol, or polyethyleneoxide-polylysine substituted with palmitoyl residues. The substances may also be coupled to biodegradable polymers useful in achieving controlled release of a drug. Suitable polymers include polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates, and crosslinked or amphipathic block copolymers of hydrogels.

Suitable pharmaceutical carriers and methods of preparing pharmaceutical dosage forms are described in *Remington's Pharmaceutical Sciences*, Mack Publishing Company, a standard reference text in this field.

More than one substance described in detail herein or identified using the methods of the invention may be used to enhance metabolism of skatole. In such cases the substances can be administered by any conventional means available for the use in conjunction with pharmaceuticals, either as individual separate dosage units administered simultaneously or concurrently, or in a physical combination of each component therapeutic agent in a single or combined dosage unit. The active agents can be administered alone, but are generally administered with a pharmaceutical carrier selected on the basis of the chosen route of administration and standard pharmaceutical practice as described herein.

e) Genetic Screening

The present invention further includes the identification of polymorphisms in genes encoding the enzymes responsible for skatole metabolism in a pig including aldehyde oxidase and CYP2A6 as described in detail hereinabove. The identification of genes that encode these enzymes from pigs that are high skatole metabolizers (and hence have a low incidence of low boar taint) can be used to develop lines of pigs that have a low incidence of boar taint. In addition, the identification of these genes can be used as markers for identifying pigs that are predisposed to having a low incidence of boar taint.

Accordingly, the present invention provides a method for producing pigs which have a lower incidence of boar taint comprising selecting pigs that express high levels of aldehyde oxidase and/or CYP2A6; and breeding the selected pigs.

Transgenic pigs may also be prepared which produce high levels of aldehyde oxidase and/or CYP2A6. The transgenic pigs may be prepared using conventional techniques. For example, a recombinant molecule may be used to introduce (a) a gene encoding aldehyde oxidase or (b) a gene encoding a CYP2A6. Such recombinant constructs may be introduced into cells such as embryonic stem cells, by a technique such as transfection, electroporation, injection, etc. Cells which show high levels of aldehyde oxidase and/or CYP2A6 may be identified for example by Southern Blotting, Northern Blotting, or by other methods known in the art. Such cells may then be fused to embryonic stem cells to generate transgenic animals. Germline transmission of the mutation may be achieved by, for example, aggregating the embryonic stem cells with early stage embryos, such as eight cell embryos, transferring the resulting blastocysts into recipient females in vitro, and generating germline transmission of the resulting aggregation chimeras. Such a transgenic pig may be mated with pigs having a similar phenotype i.e. producing high levels of aldehyde oxidase and/or CYP2A6 to produce animals having a low incidence of boar taint.

The following non-limiting examples are illustrative of the present invention:

EXAMPLES

Example 1

Identification of Skatole Metabolites

Materials and Methods

Chemicals. 3-Methylindole (3MI), indole-3-carbinol (I3C), indole-3-aldehyde, indole-3-carboxylic acid, 2-aminoacetophenone and sulfatase type H-2 from *Helix pomatia* were purchased from Sigma-Aldrich Canada Ltd. (Oakville, ON, Canada). The oxindoles, 3-methyloxindole (3MOI) and 3-hydroxy-3-methyloxindole (HMOI) were synthesized by the methods of Kende and Hodges (1982) and Skiles et al. (1989), respectively. Authentic 5-OH-3-methylindole and 6-OH-3-methylindole (in the form of 6-sulfatoxyskatole) were donated by Jens Hansen-Møller (Danish Meat Research Institute, Roskilde, Denmark). In order to obtain 6-OH-3-methylindole from 6-sulfatoxyskatole, the compound was hydrolyzed in a total volume of 0.5 ml acetate buffer pH 5.0 containing 90 units/ml of type H-2 sulfatase. Hydrolysis was conducted for 4 hours in a shaking water bath at 40° C. and then 0.5 ml of ice-cold acetonitrile were added both to stop the reaction and precipitate the protein. After centrifugation at 7,500 rpm for 15 min, 50 μl of clear supernatant were injected into the chromatograph, using the conditions described below under "Analytical chromatography".

Preparation of microsomes. Liver samples were taken from 30 intact male pigs obtained by back-crossing F3 European Wild Pig.times.Swedish Yorkshire boars with Swedish Yorkshire sows (Squires and Lundström, 1997). Liver samples were frozen in liquid nitrogen and stored at −80° C. For the preparation of microsomes, partially thawed liver samples were finely minced and homogenized with 4 volumes of 0.05 M Tris-HCl buffer pH 7.4 (containing 0.15 M KCl, 1 mM EDTA, and 0.25 M sucrose) using a Ultra-Turax homogenizer (Janke and Kunkel, GDR). The homogenate was centrifuged at 10,000 g for 20 min and the resulting supernatant was centrifuged again at 100,000 g for 60 min order to obtain the microsomal pellet. The pellets were suspended in a 0.05 M Tris-HCl buffer, pH 7.4, containing 20% glycerol, 1 mM EDTA, and 0.25 M sucrose to a final concentration of 20 mg protein/ml and stored at −80° C. before analysis. Protein concentrations were determined by the method of Smith et al. (1985) using bicinchoninic acid protein assay reagents purchased from Pierce Chemical Co. (Rockford, Ill., USA) and bovine serum albumin as standard.

Microsomal incubations. Two mg microsomal protein was incubated with 0.4 mM 3MI and 4 mM NADPH in 0.05M sodium phosphate buffer (pH 7.4) containing 5 mM $MgCl_2$ and 1 mM EDTA for 30 min at 37.degree. C. (production of metabolites was determined to be linear over a range of 10 to 40 min). Incubation volumes were 0.5 ml. Reactions were started by the addition of NADPH after 3-minute preincubation periods at 37° C., and stopped with 0.5 ml of ice-cold acetonitrile. Incubations of all 30 samples were run in duplicate and for control incubations NADPH was omitted. After the addition of acetonitrile the mixture was vortexed and centrifuged at 5000 rpm for 20 min. A 50 μl aliquot of the clear supernatant was analyzed by high-performance liquid chromatography (HPLC).

Analytical chromatography. Analytical HPLC was done using a Spectra-Physics system (Spectra-Physics, San Jose, Calif., USA) consisting of a SP8800 gradient pump, a SP8880 autosampler with a 50 μl injection loop, a SP Spectra 100 UV detector, and a Spectra System FL-2000 fluorescent detector. The HPLC method is a modification of a previously reported binary gradient system method (Baek et al., 1995). 3MI and its metabolites were separated using a reverse-phase Prodigy ODS, 5 μm, 250×4.6 mm column (Phenomenex, Torrance, Calif., USA). The mobile phase consisted of two solvents, A (0.01M potassium dihydrogen phosphate buffer pH 3.9) and B (acetonitrile), with the following gradients: 0 min—90% A, 6 min—80% A; 12 min—70% A; 18 min—30% A; 25 min 10% A; 26 min 90% A; 35 min—90% A. All gradients were linear and the flow rate was set at 1.2 ml/min. Absorbance was monitored at 250 nm; fluorescence was monitored at excitation and emission wavelengths of 286 and 350 nm, respectively. HPLC analysis for 3MI metabolites was conducted immediately after the incubations. Metabolites were identified by comparison of retention times, and co-injection of standards (spiking the metabolite mixture with authentic standards).

Isolation and purification of metabolites by preparative HPLC. In order to obtain a sufficient amount of metabolites to conduct UV spectral analysis, a large scale incubation (final volume of 4 ml) was performed, using the same concentrations of reactants as described above. Preparative HPLC was done using a Spectra-Physics SP8800 gradient pump (Spectra-Physics, San Jose, Calif., USA), a manual Rheodyne 7125 injector fitted with a 500 μl injection loop (Rheodyne, Cotati, Calif., USA), and a SP Spectra 100 UV detector. The 3MI metabolites were separated using a reverse-phase Waters preparative HPLC C 18, 10 μm, 300.times.7.6 mm column (Waters Associates, Division of Millipore Corp., Milford, Mass., USA). The mobile phase was the same as above except that the flow rate was set at 3.0 ml/min. The peaks corresponding to the metabolites identified on the basis of their retention times as HMOI, I3C, 3MOI and 2-aminoacetophenone were collected in enough amounts to determine their UV spectra. Purity of the collected fractions was verified by HPLC using the procedure described before under "Analytical chromatography". One of the metabolites produced by pig liver microsomes could not be identified on the basis of comparison of retention times; this metabolite was named UV-1 due to its absorption in the far UV spectrum and the fact that it was the first metabolite that eluted from the column (Babol et al., 1998a). The peak corresponding to this metabolite, which eluted between 9.1 and 10.1 min, was collected after several 500 μl injections and subjected to HPLC-MS, $^1$H-NMR and UV spectra analysis.

Ultraviolet Spectroscopy. UV spectra (200–300 nm) were recorded for the HPLC metabolites UV-1, HMOI, I3C, 3MOI and 2-aminoacetophenone. UV spectra of available authentic standards were also recorded and compared with those of the isolated metabolites. Spectra were recorded on a model 4054 LKB Biochrom UV-Visible spectrophotometer (Pharmacia LKB Biochrom Ltd. Cambridge, UK). Due to their low levels of production, it was not possible to isolate the hydroxyskatoles in enough quantities to determine their UV spectra.

LC/MS of metabolite UV-1. Metabolite UV-1 was analyzed by LC-MS using the following conditions: the HPLC was performed using a Prodigy 5 ODS-2, 5 μm, 150.times.3.2 mm colunm (Phenomenex, Torrance, Calif., USA) and water:acetonitrile (50:50) as mobile phase. The mobile phase was delivered by binary LC pumps (Hewlett Packard 1090 Series II/L, Palo Alto, Calif., USA). The eluent passed through a sample injection valve Rheodyne 7010 (Rheodyne, Cotati, Calif., USA), to an atmospheric pressure chemical ionization (APCI) source configured with a corona discharge pin, at a flow rate of 0.7 ml/min. A sample volume of 20 μl was injected by an autosampler (Hewlett Packard 1090 Series II/L, Palo Alto, Calif., USA). Mass spectrometry (MS) detection was achieved using a VG Quattro II triple quadrupole mass spectrometer (Fisons UK Ltd., Altrincham, UK). Instrument control, data acquisition and data processing were carried out using the MassLynx software package. Liquid nitrogen was used as a drying and sheath gas, at flow rates of 200 and 50 liter/hr, respectively. The instrument was operated in the positive ion mode with an ion source temperature of 150° C., a corona discharge pin potential of +3.75 kV, and a cone voltage of 15V. The total ion chromatogram of LC/MS was obtained by scanning the first quadrupole from m/z 125–700 at a rate of 400 amu/sec in full scan mode with inter-scan delay of 0.10 sec. Data was acquired in continuum mode. The production scan was performed by tandem mass spectrometry (MS/MS) by transmitting the protonated molecular ion ($[M+H]^+$) through the first quadrupole into the second quadrupole containing ultrapure argon. The production chromatogram was recorded by scanning the third quadrupole from m/z 50 to 450 in 1.0 sec. The collision energy was varied between −20 to −50 eV to optimize fragmentation of the selected protonated molecular ion.

NMR spectroscopy of metabolite UV-1. UV-1 metabolite was isolated for NMR analysis using incubation conditions essentially as described above. However, these incubations contained 1 nmol cytochrome P450 content rather than 2 mg of total protein. UV-1 was separated from other microsomal 3MI metabolites by the HPLC conditions described above using a system consisting of an LDC Analytical Constametric 4100 solvent delivery module (ThermoQuest, Riviera Beach, Fla., USA), a Hewlett Packard 1040A diode array detector and a Hewlett Packard 9000 series HPLC workstation (Hewlett Packard Company, Willington, Del., USA). UV-1 was purified by HPLC and pooled from two identical incubations followed by concentration in a Savant Speed-Vac (Savant Instruments, Farmingdale, N.Y., USA). Concentration to dryness was not possible, due to polymerization and degradation of unstable UV-1. Therefore, the sample was evaporated to a volume of 200 L and re-injected on the HPLC for additional purification. In this case however, the aqueous mobile phase consisted of 0.01 M dibasic potassium phosphate buffer, pH 9.0, in 99.9 atom % deuterium oxide. Due to the instability of UV-1 when it was evaporated to dryness, it was necessary to perform the final purification step in the NMR solvent, deuterium oxide. UV-1 was again collected and evaporated to a final volume of 250 L and directly added to the Shigemi NMR tube. The $^1$H-NMR spectrum was obtained in deuterium oxide using a Varian Unity Inova 600 MHz NMR (Varian Associates Inc., Palo Alto, Calif., USA).

Results

HPLC. None of the metabolites produced by pig liver microsomes co-eluted with indole-3-carboxaldehyde or indole-3-carboxylic acid. However, metabolites that coeluted with HMOI, 3MOI, I3C, 2-aminoacetophenone, and the two hydroxyskatoles (5- and 6-OH-3-methylindole) were measured by UV and/or fluorescence detection. The oxindole metabolites (HMOI and 3MOI) and the pyrrole ring opened metabolite (2-aminoacetophenone) were detected and quantitated by UV absorption because they do not fluoresce; I3C and the hydroxyskatoles were detected and quantitated by fluorescence detection. When microsomal incubations were spiked, all metabolites identified on the basis of their retention times, co-chromatographed with their corresponding authentic standards. The chromatographic profile of a microsomal incubation and a standard mixture monitored by UV absorption at 250 nm is shown in FIG. 1.

UV Spectroscopy. The UV spectrum of the metabolites identified on the basis of their retention times on HPLC (HMOI, 3MOI, I3C, and 2-aminoacetophenone) were identical to those of authentic standards. Spectra of metabolites were recorded using water as solvent, and the wavelengths of maximal absorption were as follows: HMOI: $\lambda_{max}$ (nm): 208, 253; 3MOI: $\lambda_{max}$ (nm): 205, 252; I3C: $\lambda_{max}$ (nm): 221, 278; 2-aminoacetophenone: $\lambda_{max}$ (nm): 228, 257. The UV spectrum of 3-methylindole was: $\lambda_{max}$ (nm): 224, 281. The UV spectrum of UV-1 metabolite was: $\lambda_{max}$ (nm): 204, 238. The UV spectra of UV-1 was similar to the spectra of the oxindole metabolites 3MOI and HMOI as shown in FIG. 2. Changing the pH from 3 to 11 did not change the spectrum of UV-1; this lack of a bathochromic shift indicated that the unknown metabolite had no free phenolic group. Isolated UV-1 was kept in acetonitrile:water solution at room temperature and the solution was analyzed by HPLC at 7-day intervals for 6 weeks. After 6 weeks only about 25% of the original compound remained and it was observed that UV-1 was converted into 3MOI. The slopes of the linear regressions of 3MOI and UV-1 over time indicated that the molar response factor for UV-1 on HPLC-UV analysis was 2.95 times that of 3MOI.

Figure 4:
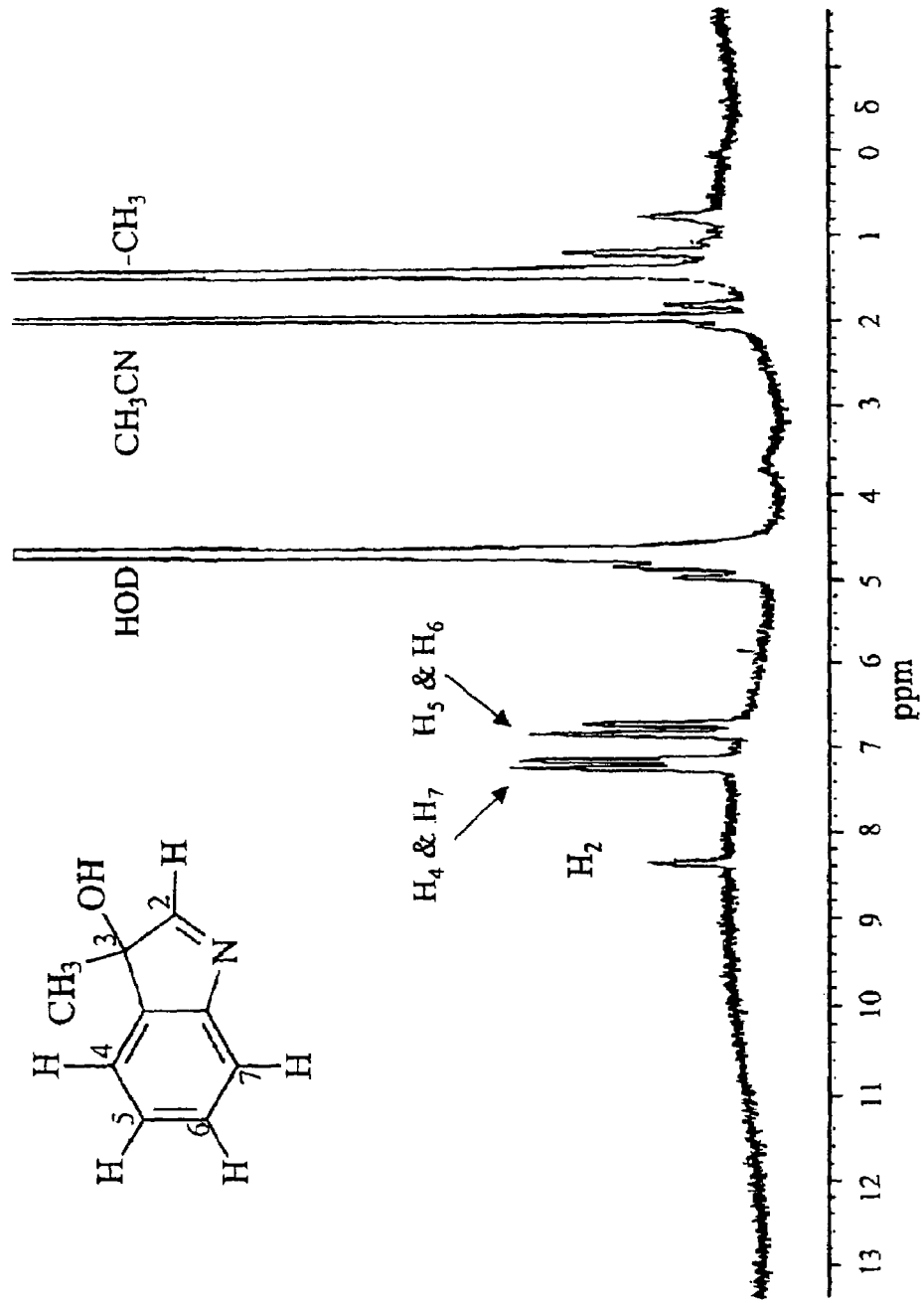
FIG. 4 is an $^1$H-NMR spectrum of metabolite UV-1.

Metabolite UV-1 structural data. The mass spectrometry of isolated UV-1 produced a molecular ion at m/z 148 [M+H].sup.+ with major fragments at m/z 133 [M—$CH_3$]$^+$, 104 [M—$H_3$ C—C—OH]$^+$, and 77 (protonated phenyl ring) (FIG. 3). The $^1$H-NMR spectrum of metabolite UV-1 is shown in FIG. 4. Assignments of the proton signals are provided, listed as chemical shift (multiplicity, integration and assignment): 1.4 (s, 3H, —$CH_3$); 6.8 (d, 2H, H-5 and H-6); 7.2 (d, 2H, H-4 and H-7); 8.4 (s, 1H, H-2). The singlet at 8.4 has been assigned to the proton at C-2 of 3-hydroxy-3-methylindolenine. This proton is attached to the sp.sup.2 hybridized C-2 which is also a deshielded by the adjacent nitrogen. Therefore, this proton is highly deshielded and appears downfield from all other protons in the proposed structure. At 2.0 is a singlet corresponding to the methyl protons of contaminating acetonitrile. Due to the way in which the sample was purified, it was extremely difficult to remove all of the acetonitrile present in the HPLC organic phase.

Figure 5:
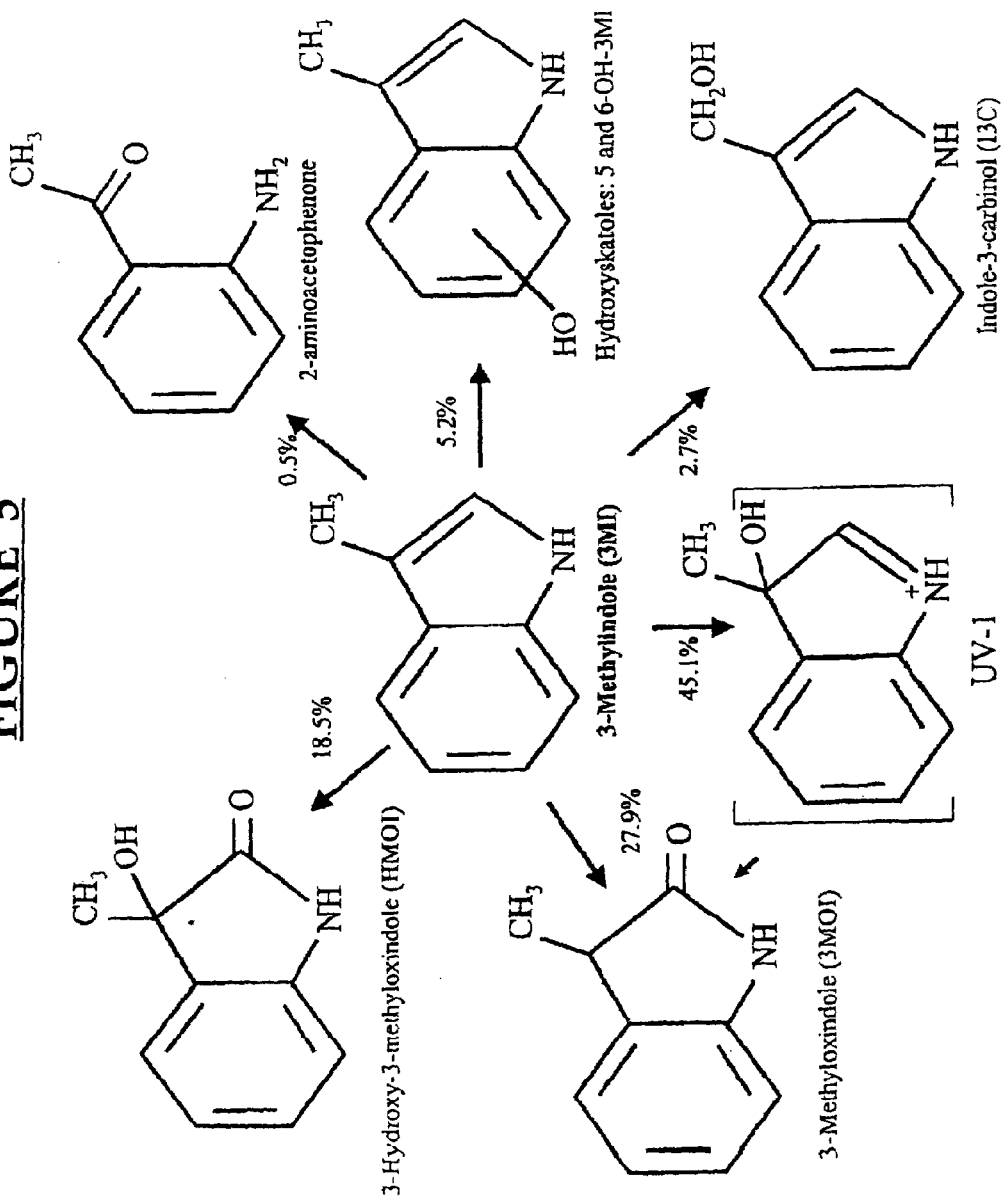
FIG. 5 shows chemical structures and percentages of 3MI metabolites produced by pig liver microsomes.

In summary, seven metabolites of 3MI were found to be produced by pig liver microsomes: 3MOI, HMOI, 6-OH-3-methylindole (6-OH-3MI), I3C, 2-aminoacetophenone, 5-OH-3-methylindole (5-OH-3MI), and the metabolite that was named UV-1. When UV-1 was quantitated assuming a molar absorptivity 2.95 times greater than that of 3MOI, the total amount of nanomoles produced accounted for an average of 96.0% (range of 86.5–105.0%) of the 3MI molecules metabolized during the microsomal incubations. The rates of production of the seven metabolites identified in pig liver microsomal incubations are shown in Table 1. UV-1 metabolite was produced at the highest rate (750.7 pmol/mg protein/min), while 5-OH-3MI was produced at the lowest rate (5.1 pmol/mg protein/min). Large inter-individual differences were noted for the production rates of the same metabolite. For instance, UV-1 metabolite was produced at a rate of 1556.3 pmol/mg protein/min by the microsomes of one pig, while other microsomes produced this compound at a rate of 180.5 pmol/mg/protein/min (Table 1). The metabolite that was produced in larger amounts was UV-1 which, on average, accounted for 45.1% of all metabolites produced. The combined oxindoles accounted for 46.4% of the total metabolites: an average of 27.9% of the metabolites produced corresponded to 3MOI whereas 18.5% corresponded to HMOI. The other metabolites were produced in much lesser amounts. 6-OH-3MI accounted for 4.9% of the metabolites, I3C accounted for 2.7% and 2-aminoacetophenone and 5-OH-3MI accounted for only 0.5% and 0.3% of the metabolites, respectively. The chemical structures and percentages of production of these metabolites are shown in FIG. 5.

Discussion

Only three Phase I metabolites of 3MI had been identified previously in pigs: HMOI, and the hydroxyskatoles, 5-OH-3MI and 6-OH-3MI. HMOI had been found in pig plasma and urine (Baek et al., 1997), and pig liver microsomal incubations (Babol et al., 1998a); 6-OH-3MI had been detected both in pig serum (Baek et al., 1997) and pig liver microsomal incubations (Babol et al., 1998a), while 5-OH-3MI had only been reported to be present in pig serum (Baek et al., 1997). In the present study, all three metabolites were detected in the microsomal incubations and the production of four new metabolites is reported.

One of the pathways of 3MI biotransformation identified in species such as goats, mice and rats is the formation of oxindole derivatives: 3MOI and HMOI (Frydman et al., 1972; Smith et al., 1993). On average, 46.4% of the metabolites produced by pig liver microsomes in the present study corresponded to these two oxindole derivatives; this finding indicates that the oxidole pathway is quantitatively very important in the pig. 3MOI had been identified in rat liver microsomal incubations (Frydman et al., 1972), goat lung and liver microsomal incubations (Huijzer et al., 1987), and in the urine of goats (Hammond et al., 1979). One of the metabolites observed in pig microsomal incubations by Babol et al. (1998a) was named "UV-3" and the results of the present study indicate this metabolite corresponds to 3MOI. The other oxindole derivative of 3MI, HMOI, had already been isolated from the urine of pigs dosed with 3MI (Baek et al., 1997) and was also reported to be produced by pig liver microsomes (Babol et al., 1998a); HMOI is also a major urinary metabolite produced by mice dosed with radiolabeled 3MI (Skiles et al., 1989), additionally it has been found in the urine of humans (Albrecht et al., 1989), and goats (Smith et al., 1993). Interestingly, in the present study, pig liver microsomes produced large amounts of both oxidole derivatives 3MOI and HMOI. In other species studied, one of these metabolites predominates. In goats, production of 3MOI predominates (Hammond et al., 1979), whereas in mice it is HMOI that predominates (Smith et al., 1993).

The 3 methyl group of 3MI may be oxidized to the alcohol, aldehyde and carboxylic acid functions (Hammond et al., 1979). In the present study, only the alcohol function of the 3 methyl group (indole-3-carbinol) was found to be produced by pig liver microsomes. This metabolite exhibits strong fluorescence and also absorbs in the UV and even though it had been previously reported to be produced by pig microsomes (named F-1 by Babol et al., 1998a), its structure was unknown. It is important to note that further metabolism of the alcohol function of indole-3-carbinol could possibly be catalyzed by alcohol dehydrogenase; if this is true, then the product of this reaction, indole-3-carboxaldehyde, would not be produced in microsomal incubations.

Hydroxylation of the aromatic ring of 3MI can occur at any of the carbons 4, 5, 6 or 7; however, the experimental evidence indicates that hydroxylation at positions 5 and 6 predominate. In 1962, Jepson and co-workers showed that rabbit liver microsomes hydroxylate tryptamine, indole acetic acid and related indoles to their corresponding 6-hydroxy derivatives. The microsomal system required NADPH and oxygen and did not form 5- or 7-hydroxyindoles (Jepson et al., 1962). Mahon and Mattok (1967) analyzed the urine of ten normal human subjects and found that all samples contained 6-hydroxyskatole and nine had the 5-isomer, although its excretion rate was approximately 50% of the 6-isomer; 7-hydroxyskatole was detected in three of the samples but its excretion rate was only 5% of the 6-isomer. None of the subjects excreted 4-hydroxyskatole (Mahon and Mattok, 1967). Baek et al. (1995) found conjugates of both 5-OH-3MI and 6-OH-3MI in pig serum. In the present study, the average rate of production of 6-OH-3MI was approximately eleven times greater than the production of the 5 isomer, indicating that hydroxylation at position C6 predominates.

Frydman et al. (1972) found two pyrrole ring opened metabolites produced after incubation of 3-MI with rat liver microsomes. The two compounds were identified as 2-formamidoacetophenone and 2-aminoacetophenone; a total of 33% of the metabolites formed corresponded to 2-formamidoacetophenone, 12% to 2-aminoacetophenone, and 5% to 3-MOI. In the present study, 2-aminoacetophenone was found to be produced by all liver samples analyzed at an average percentage of 0.5%, which is much lower than the percentage reported for rats by Frydman et al. (1972). No previous reports of 2-aminoacetophenone production from 3MI metabolism by pigs were found in the literature.

The $^1$H-NMR, LC-MS and UV-spectral characteristics of metabolite UV-1 indicate that this compound corresponds to 3-hydroxy-3-methylindolenine. UV-1 was found to be an unstable compound, intermediate between 3MI and 3MOI. The fact that UV-1 was converted into 3MOI suggested that this compound could be a precursor of 3MOI, possibly 2,3-epoxy-3-methylindolenine, the structure of which was postulated by Smith et al. (1993) or, most likely, its ring-opened product, 3-hydroxy-3-methylindolenine (Skordos et al., 1998a, 1998b). The molecular weight of the compound (147) and its fragmentation pattern were compatible with the epoxyde or the imine (FIG. 3), but the UV spectrum, with a $\lambda_{max}$ at 238 nm (FIG. 2) was more consistent with the imine structure. The molecular weight of 147 could also correspond to an aromatic phenolic metabolite of 3MI; however, when the UV spectrum of isolated UV-1 was taken under different pHs, it did not show the typical bathochromic shift observed in phenolic indoles. Furthermore, the fact that the UV spectrum of metabolite UV-1 was very similar to that of 3MOI and HMOI (FIG. 2) indicated that metabolite UV-1 could be structurally related to any of the two oxindoles; these metabolites, in which the pyrrol ring is oxidized at the 2-carbon position, show very different spectra than 3MI, or other metabolites such as I3C, 2-aminoacetophenone or the hydroxyskatoles. Finally, the $^1$H-NMR spectrum of UV-1 (FIG. 4) was consistent with the assignment of this metabolite to 3-hydroxy-3-methylindolenine.

The results of the present study indicate that seven major metabolites of 3MI are produced by pig liver microsomes in vitro. In quantitative terms, the main pathway of Phase I biotransformation of 3MI by pig liver microsomes appears to be the formation of oxindole derivatives and the formation of 3-hydroxy-3-methylindolenine. Differences in the metabolic fate of 3MI among species could explain the difference in species susceptibility to 3MI-induced lung toxicity. The extensive metabolism of 3MI to oxindole derivatives may explain the lack of pneumotoxicity showed by pigs and reported by Carlson and Yost (1989). The electrophilic metabolite 3-methylene-indolenine, which is the putative reactive metabolite of 3MI produced by cytochrome P-450 enzymes, is a precursor of I3C in lung microsomal incubations and susceptible species form I3C in appreciable amounts (Skiles and Yost, 1996). In the present in vitro study, less than 3% of the metabolites produced by pig liver microsomes corresponded to I3C, which may also explain the lack of susceptibility of pigs to suffer from 3MI-induced lung lesions. Large inter-individual differences in the rate of production of metabolites were observed. These differences in Phase I metabolism could be due to individual differences in cytochrome P450 enzymes and this issue should be further investigated. It was previously reported that CYP2E1 plays a role in the metabolism of 3MI in the pig (Squires and Lundström, 1997; Babol et al., 1998a), but the role of other isoenzymes remains to be determined. Babol et al. (1998b) reported sulfation and glucuronidation of some 3MI metabolites produced by pig liver microsomes. However, more studies are needed in order to determine the complete Phase II metabolism of the different metabolites of 3MI identified in the present study.

Example 2

Aldehyde Oxidase

Materials And Methods

Chemicals. Menadione, quinacrine and allopurinol were purchased from Sigma-Aldrich Canada (Oakville, ON, Canada). Authentic HMOI was graciously provided by Dr. G. S. Yost, Department of Pharmacology and Toxicology, University of Utah. HMI was produced using porcine liver microsomes and it was isolated and purified using preparative HPLC as described before (Diaz et al., 1999). Isolated HMI was freeze-dried and kept in a dessicator at −20° C. until used.

Preparation of porcine liver cytosol. Liver samples were taken from 30 intact male pigs obtained by back-crossing F3 European Wild Pig×Swedish Yorkshire boars with Swedish Yorkshire sows (Squires and Lundström, 1997). Liver samples were frozen in liquid nitrogen and stored at −80° C. For the preparation of the cytosolic fraction, partially thawed liver samples were finely minced and homogenized with 4 volumes of 0.05 M Tris-HCl buffer pH 7.4 (containing 0.15 M KCl, 1 mM EDTA, and 0.25 M sucrose) using a Ultra-Turax homogenizer (Janke and Kunkel, GDR). The homogenate was centrifuged at 10,000×g for 20 minutes and the resulting supernatant was centrifuged again at 100,000×g for 60 minutes in order to obtain the cytosolic fraction and the microsomal pellet. Cytosolic fractions were stored at −80° C. before analysis. Protein concentrations were determined by the method of Smith et al. (1985) using bicinchoninic acid protein assay reagents purchased from Pierce Chemical Co. (Rockford, Ill., USA) and bovine serum albumin as standard.

Enzyme assays. In order to investigate the role of AO in the conversion of HMI to HMOI, incubations containing HMI, porcine liver cytosol and different concentrations of the selected AO inhibitors menadione and quinacrine were conducted. Each incubation was run in duplicate, and were performed for three randomly selected cytosol porcine samples. HIMOI formation was detected and quantitated by HPLC as described under "Chromatographic analysis". AO activity was measured as the formation of HMOI per minute per mg of cytosolic protein. Assay mixtures contained 0.05M sodium phosphate buffer (pH 7.4) with 5 mM $MgCl_2$ and 1 mM EDTA, 1 mg cytosolic protein and 1 μg HMI in a final assay volume of 250 μl. For the inhibition experiments, different final concentrations of menadione (0, 2, 5, 10, 25, 50 and 100 μM) or quinacrine (0, 0.05, 0.1, 0.25, 0.5 and 1.0 mM) were tested in the assay mixture. Menadione was dissolved in ethanol (final assay concentration 4%, v/v), which had no effect on activity in controls without inhibitor; quinacrine was dissolved in buffer. Incubations were carried out for 10 min at 37° C. in a shaking water bath; the reaction was stopped with 250 μl ice-cold acetonitrile. After the addition of acetonitrile, the mixture was vortexed and centrifuged at 7,500 rpm for 15 min. A 400 μl aliquot of the clear supernatant was diluted with 400 μl water and 100 μl of the mixture were analyzed immediately by high-performance liquid chromatography (HPLC). Dilution with water was necessary in order to avoid leading of the chromatographic peaks. HMOI production was quantitated by using an external standard. Controls included incubations using boiled cytosol and incubations carried out without the addition of cytosol. Incubations run under the same conditions described above were conducted using 0.1, 0.5 and 1.0 mM allopurinol in order to investigate the role of XO on the enzymatic conversion of HMI into HMOI.

Chromatographic analysis. HPLC was conducted using a Spectra-Physics system (Spectra-Physics, San Jose, Calif., USA) consisting of a SP8800 gradient pump, a SP8880 autosampler with a 100 μl injection loop, and a SP Spectra 100 UV detector. The HPLC method is a modification of a previously reported binary gradient system method (Baek et al., 1997). HMOI and HMI were separated using a reverse-phase Prodigy ODS, 5 μm, 250×4.6 mm column (Phenomenex, Torrance, Calif., USA). The mobile phase consisted of two solvents, A (0.01 M potassium dihydrogen phosphate buffer pH 3.9) and B (acetonitrile), with the following gradients: 0 min—90% A, 6 min—80% A; 12 min—70% A; 18 min—30% A; 25 min 10% A; 26 min 90% A; 35 min—90% A. All gradients were linear and the flow rate was set at 1.2 ml/min. Absorbance was monitored at 250 nm. HPLC analysis was conducted immediately after the incubations.

Measurement of 3MI fat content. For the quantitation of the 3MI fat content, a sample of backfat was taken from each pig and its 3MI content measured with a colorimetric assay (Mortensen and Sorensen, 1984). All analysis were done in duplicate.

Statistical analysis. Pearson correlation coefficients, linear regression analysis and one-way ANOVA were computed using the Statistical Analysis System (SAS, 1995).

Results

Figure 6:
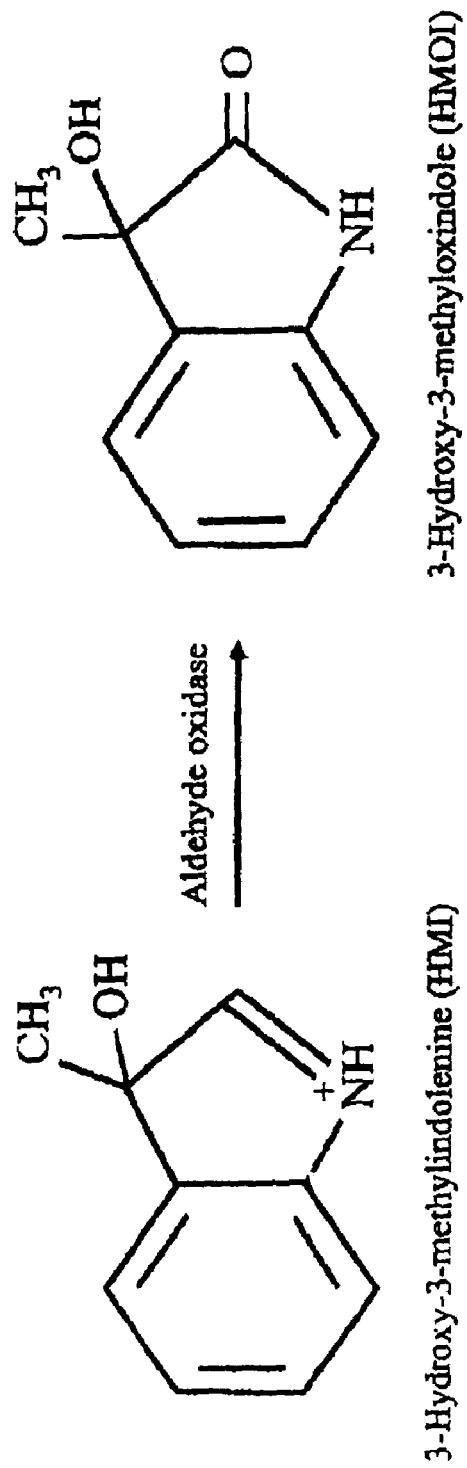
FIG. 6 shows the oxidative conversion of 3-hydroxy-3-methylindolenine into 3-hydroxy-3-methyloxindole catalyzed by aldehyde oxidase.
Figure 7:
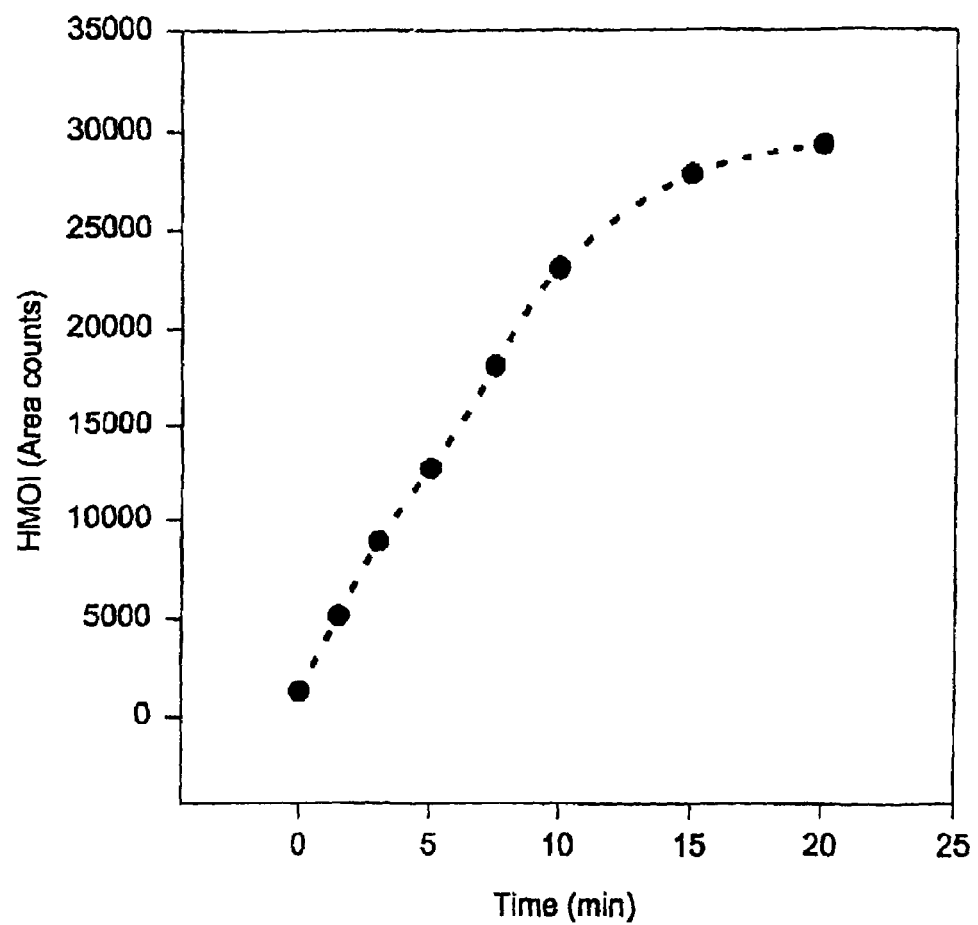
FIG. 7 shows the formation of 3-hydroxy-3-methyloxindole (HMOI) from 3-hydroxy-3-methylindolenine, catalyzed by porcine cytosol. Each data point represents the mean of duplicate assays performed for three pigs.
Figure 8:
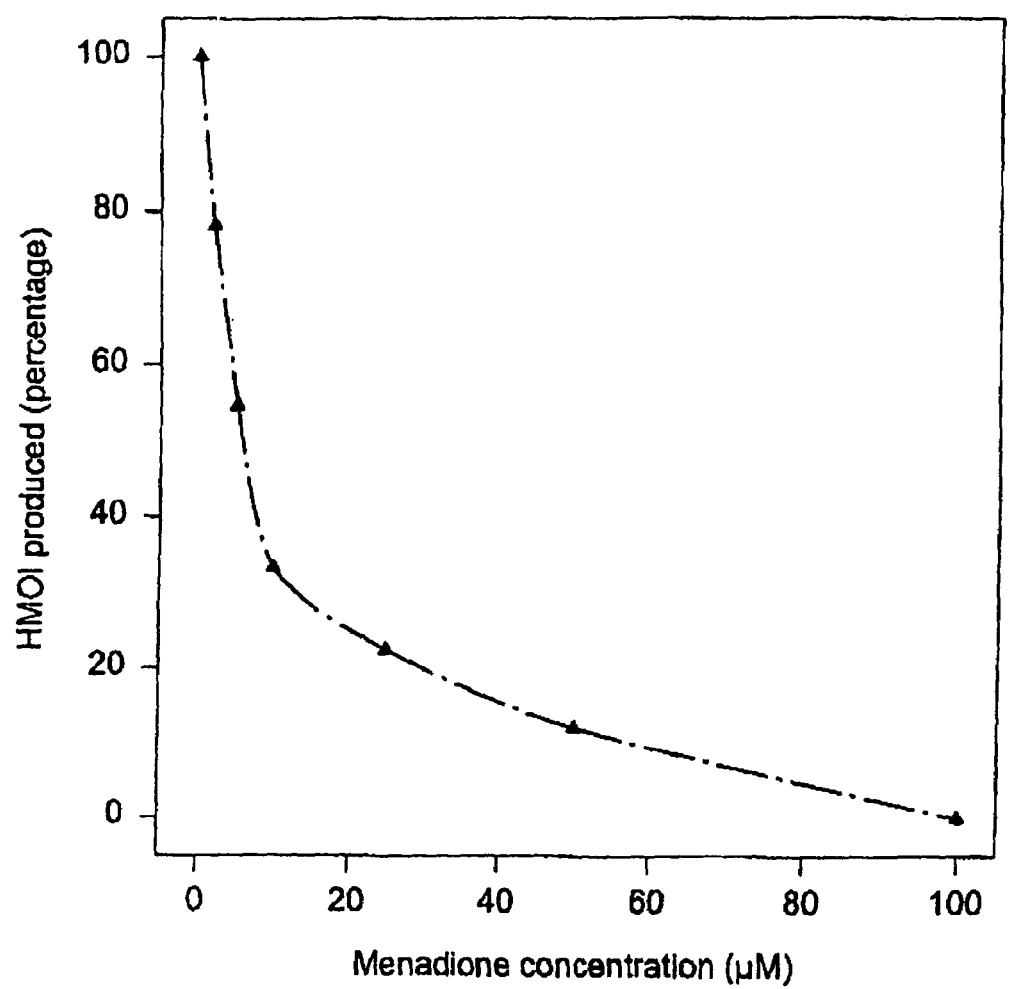
FIG. 8 shows the menadione-induced inhibition of the formation of 3-hydroxy-3-methyloxindole (HMOI) from 3-hydroxy-3-methylindolenine. Each data point represents the mean of duplicate assays performed for three pigs.
Figure 9:
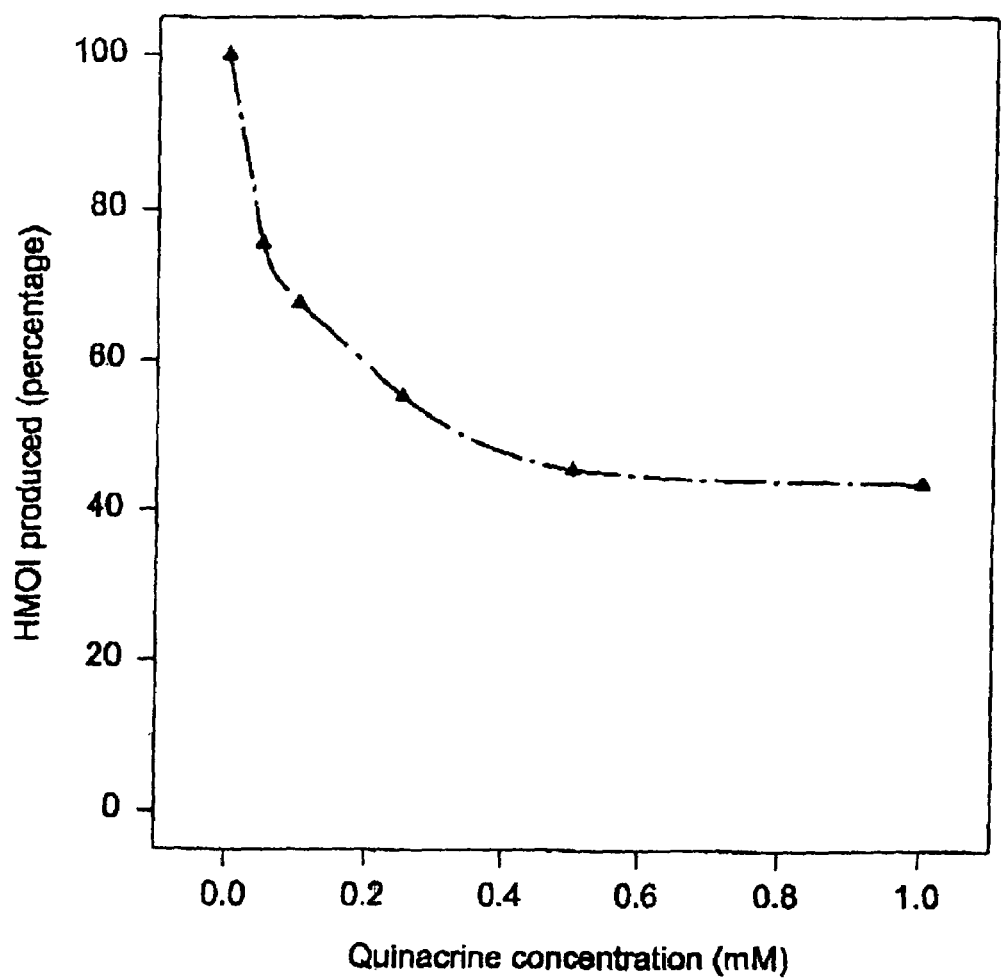
FIG. 9 shows the quinacrine-induced inhibition of the formation of 3-hydroxy-3-methyloxindole (HMOI) from 3-hydroxy-3-methylindolenine. Each data point represents the mean of duplicate assays performed for three pigs.

Porcine cytosol catalyzed the conversion of HMI to HMOI (FIG. 6) in a time-dependent manner (FIG. 7). Under these assay conditions, the formation of HMOI was found to be linear ($r^2$=0.995) up to 10 min (FIG. 7). No HMOI was formed when cytosol was boiled before the incubation or when no cytosol was added to the assay mixture. The addition of the aldehyde-oxidase inhibitors menadione or quinacrine to the incubation mixtures containing HMI and cytosolic protein decreased the formation of HMOI in a dose-dependent manner. When no inhibitor was added, the total amount of HMOI produced was considered as 100%. At a concentration of 10 μM menadione, only 33.3% of the HMOI formed in the absence of menadione was detected whereas at a concentration of 100 μM menadione, no HMOI was produced (FIG. 8). At a concentration of 50 μM quinacrine, 75.5% of the control HMOI production was observed and at 1 mM 43.4% of the control HMOI was found (FIG. 9). Menadione was a more potent inhibitor of the reaction since even a concentration of quinacrine 10 times higher than that of menadione (1 mM vs 100 μM) was not enough to completely abolish the conversion of HMI to HMOI. The addition of up to 1.0 mM allopurinol to the assay mixture did not affect the conversion of HMI to HMOI (data not shown).

Figure 10:
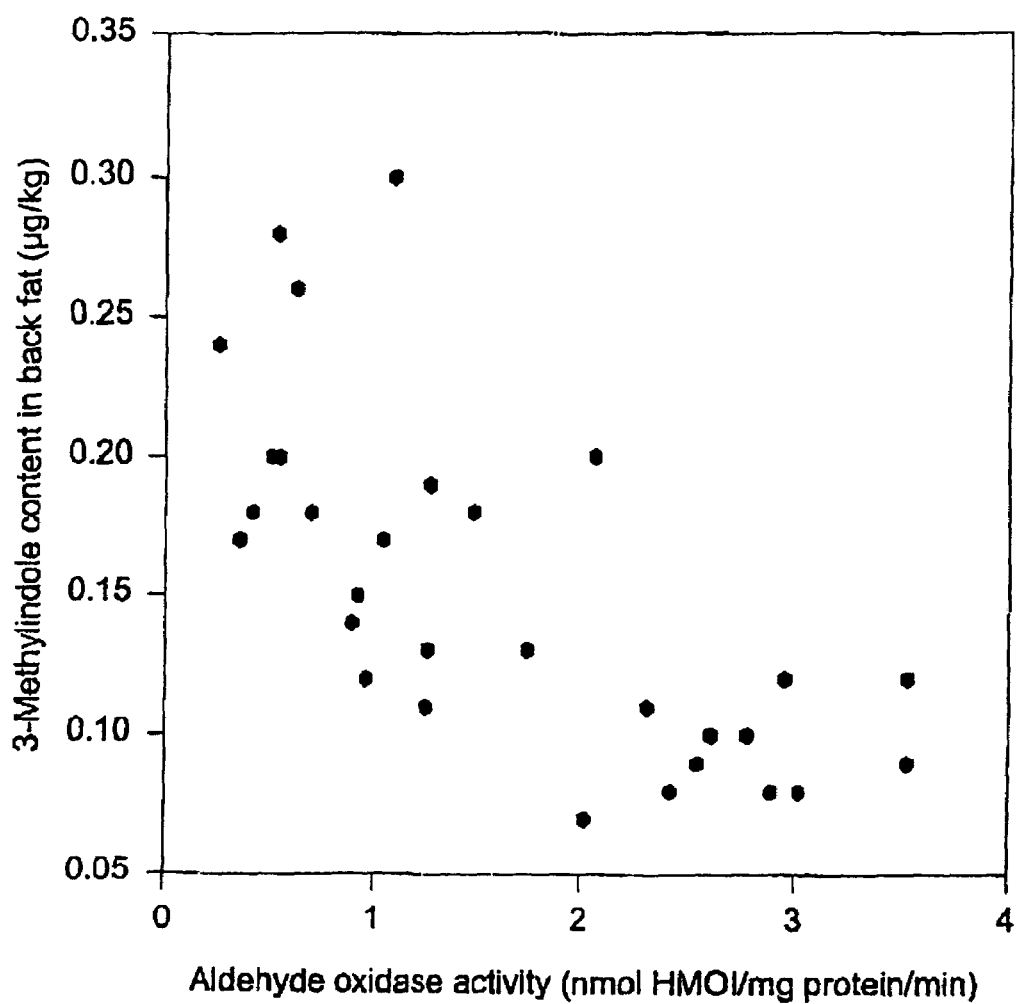
FIG. 10 shows the plot of back fat 3-methylindole content versus hepatic aldehyde oxidase activity in pigs (n=30). Aldehyde oxidase activity measured as nmol of 3-hydroxy-3-methyloxindole (HMOI) formed per mg of cytosolic protein per min.

The AO activity, estimated as nmol of HMOI produced per minute per mg cytosolic protein, versus the 3MI fat content of the 30 pigs used in this study are shown in FIG. 10. The Pearson correlation coefficient between these two variables was found to be −0.70 (P<0.001), whereas the determination coefficient was $r^2$=0.49. The linear regression model to explain the 3MI fat content as a function of AO activity was found to be: 3MI in fat=0.22—AO activity 0.042763. This model was found to be highly significant (P<0.001).

The 3MI fat content in all samples ranged from 0.07 to 0.3 mg/kg and had mean value of 0.15 mg/kg, whereas the AO activity ranged from 0.25 to 3.53 nmol HMOI/mg protein/min and had a mean value of 1.27 nmol HMOI/mg protein/min. The results were grouped in three categories according to the 3MI fat content of each pig as follows: large 3MI accumulators (0.2 mg/kg 3MI or more), moderate 3MI accumulators (0.11 to 0.19 mg/kg 3MI) and low accumulators (0.1 mg/kg 3MI or less). Lundström and Bonneau (1996) have suggested that levels of 3MI of 0.2–0.25 mg/kg or greater cause unacceptable taint by sensory analysis. The mean values for 3MI fat content and AO activity for these three categories of pigs are shown in Table 2.

Discussion

Menadione is a well documented inhibitor of AO (Johns, 1967; Krenitzky et al., 1974; Rodrigues, 1994) and biochemical reactions sensitive to inhibition by menadione are attributed to AO (Beedham et al., 1995; Rashidi et al., 1997). Rodrigues (1994) found that at a concentration of 10 µM, menadione completely abolished the oxidation of $N^1$-methylnicotinamide, the model substrate for AO. In the present experiment, a concentration of 10 µM menadione decreased the formation of HMOI by 56.7%, and at 100 µM menadione, no HMOI was formed, indicating a complete inhibition of the enzymatic activity. The inverse dose-response relationship observed between HMOI production and menadione concentration strongly suggests that AO is the enzyme responsible for the biotransformation of HMI into HMOI in porcine cytosol. Quinacrine has been reported as being a competitive inhibitor ($K_i = 1.5 \times 10^{-6}$ M) of aldehyde oxidase against all substrates (Rajagopalan and Handler, 1964). In the present trial, quinacrine was less potent than menadione in inhibiting the conversion of HMI into HMOI but it also inhibited the reaction to a large extent. The inhibition of HMOI formation caused by quinacrine also suggests that the production of HMOI from HMI is catalyzed by AO. On the other hand, the lack of inhibition observed when allopurinol was added to the reaction mixture indicates that XO is not involved in the oxidative metabolism of HMI into HMOI.

N-heterocyclic cations constitute a major group of substrates for AO (Beedham, 1985). Quaternization of a ring nitrogen atom activates the heterocycle to nucleophilic substitution and enhances the reactivity of the compound toward enzyme-catalyzed attack (Beedham, 1985). HMI is a recently identified N-heterocyclic quaternized metabolite produced by porcine microsomal enzymes (Diaz et al., 1999) and therefore it constitutes a suitable substrate for AO-catalyzed oxidation. The results of the present study strongly suggest that AO activity present in the cytosol of pigs is responsible for the oxidation of HMI to form a more polar and stable metabolite, HMOI.

When hepatic AO activity (measured as the formation of HMOI) was plotted against the 3MI fat content, a clear inverse relationship was observed (FIG. 9). This finding suggests that hepatic AO activity is related to 3MI clearance. The relatively high determination coefficient ($r^2 = 0.49$) indicates that almost 50% of the variation in 3MI fat content is explained by the hepatic enzymatic activity of AO. The results shown on Table 2 also indicate that AO activity may be very significant in the adequate clearance of 3MI in the pig. High 3MI fat levels were associated with low enzymatic activity (mean values of 0.24 mg/kg 3MI and 0.80 nmol HMOI/mg protein/min, respectively), whereas low 3MI levels were associated with high enzymatic activity (mean values of 0.09 mg/kg 3MI and 2.73 nmol HMOI/mg protein/min, respectively). Pigs classified as high 3MI accumulators had a hepatic mean AO activity 3.4 times lower than those pigs classified as low accumulators; this difference was found to be significant ($P < 0.05$).

The results of the present study suggest that AO plays an important role in the metabolism of 3MI in the pig and that its catalytic activity is related to an adequate 3MI clearance. The enzymatic activity of AO in the pig might be used as a potential marker in order to identify pigs containing low levels of 3MI in the fat, which will eventually help to control "boar taint".

Menadione is customarily used as a source of vitamin K in swine diets (National Research Council, 1987). ecommended levels of inclusion are 2.5 mg/kg for grower diets and 2.0 mg/kg for finisher diets (Patience et al., 1995). Since menadione is a potent inhibitor of AO and the enzyme appears to be important in the metabolism of 3MI, care should be exercised so that excessive levels of menadione are not present in swine diets. It is possible that some of the sporadic episodes of "boar taint" could had been caused by high levels of menadione in the diet resulting in high levels of 3MI in the fat of pigs. Studies are needed in order to determine whether the levels of menadione commonly used in practical pig diets are capable of inhibiting AO activity. Additionally, it has been observed that high levels of dietary copper lead to molybdenum deficiency and thus to low AO activity because molybdenum is a cofactor for this enzyme (Beedham, 1985). It is important to avoid excess copper levels in pig diets in order to avoid a decrease in the activity of AO and the potential occurrence of "boar taint" episodes.

Example 3

The Role of CYP2A6 in 3-Methylindole Metabolism by Porcine Liver Microsomes

The role of different cytochrome P450 enzymes on the metabolism of 3-methylindole (3MI) was investigated using selective chemical inhibitors. Eight chemical inhibitors of P450 enzymes were screened for their inhibitory specificity towards 3MI metabolism in porcine microsomes: alpha-naphthoflavone (CYP1A2), 8-methoxypsoralen (CYP2A6), menthofuran (CYP2A6), sulphaphenazole (CYP2C9), quinidine (CYP2D6), 4-methylpyrazole (CYP2E1), diethyldithiocarbamate (CYP2E1, CYP2A6), and troleandomycin (CYP3A4). The production of the different 3MI metabolites was only affected by the presence of inhibitors of CYP2E1 and CYP2A6 in the microsomal incubations. In a second experiment, a set of porcine microsomes (n=30) was screened for CYP2A6 content by Western blot analysis and also for their 7-hydroxylation activity (CYP2A6 activity). Protein content and enzymatic activity were found to be correlated with 3MI fat content. The results of the present study indicate that measurement of CYP2A6 levels and/or activity is a useful marker for 3MI-induced boar taint.

TABLE 1

Rate of production of 3MI metabolites by pig liver microsomes (pmol/mg microsomal protein/min) (n = 30)

| Metabolite | Rate of Production (pmol/mg prot./min) ±SD | Minimum (pmol/mg prot./min) | Maximum (pmol/mg prot./min) |
|---|---|---|---|
| UV-1 | 750.7 ± 414.5 | 180.5 | 1556.3 |
| 3-methyloxindole | 420.9 ± 118.1 | 234.4 | 700.8 |
| 3-hydroxy-3-methyloxindole | 272.4 ± 91.6 | 118.9 | 516.5 |
| 6-OH-3-methylindole | 58.4 ± 47.2 | n.d.* | 213.7 |
| Indole-3-carbinol | 37.1 ± 15.8 | 12.1 | 85.7 |
| 2-aminoacetophenone | 7.8 ± 2.4 | 3.4 | 12.7 |
| 5-OH-3-methylindole | 5.1 ± 5.8 | 0.7 | 27.3 |

*n.d. = not detected

TABLE 2

| Category | 3-Methylindole fat content | n | Mean (SD) 3-methylindole content (mg/kg) | | Mean (SD aldehyde oxidase activity (nmol HMOI/mg prot./min) | |
| --- | --- | --- | --- | --- | --- | --- |
| High accumulator | 0.2 mg/kg or more | 7 | 0.24 | 0.4[a] | 0.80 | 0.61[b] |
| Moderate accumulator | 0.11–0.19 mg/kg | 15 | 0.15 | 0.03[b] | 1.40 | 0.90[b] |
| Low accumulator | 0.1 mg/kg or less | 8 | 0.09 | 0.01[c] | 2.73 | 0.45[a] |

[a]–[c]Within a column, means lacking a common superscript differ significantly ($P < 0.05$).

Example 4

According to the invention, the association of alternate forms of cytochrome P450 enzymes such as the CYP2A6 may be used to identify and select pigs with differences in boar taint. For example, according to the invention, a deletion mutant of the CYP2A6 gene has been identified that results in a frame shift and loss of function mutation, which resulted in higher skatole levels in the pig.

We have cloned the pig isoforms of CYP2A6. We found a deletion mutation that results in a frame shift and premature stop. This animal has zero enzyme activity for CYP2A6 (coumarin 7-hydroxylase) in the liver and high skatole levels in fat. Another polymorphism was identified which resulted in a t to c transition at nt number 124 and a change from Phe to Leu at amino acid number 42 of SEQ ID NO:3 (wild type).

Further according to the invention, other polymorphisms in genes related to skatole metabolism (other cytochrome P450 related genes) in the pig may be identified to genetically identify and select pigs based upon their proclivity to boar taint. Once an association between a gene or gene product and a particular trait is made, genes encoding these proteins may be screened for polymorphism or markers which may be used to indicate differences in these animals with respect to the correlated trait. These polymorphisms with these genes enables genetic markers to be identified for specific breeds or genetic lines or animals, boar taint potential early in the animal's life.

An alternate form of CYP2A6 has been identified according to the invention which results in a frameshift causing a premature stop codon and loss of function resulting in higher skatole levels in the pig. Tests for the presence of this alternate form may be developed using the novel sequence for CYP2A6 as disclosed herein, SEQ ID NO: 18 or 3 supra and the mutations disclosed herein in SEQ ID NO:1 (both 124 nt and 422 deletion), SEQ ID NO:5 (124nt only) and SEQ ID NO:7 (422 deletion only). These tests include but are not limited to PCR, SSCP, and the like.

The invention thus relates to genetic markers for economically valuable traits in animals. The markers represent alleles or alternate gene forms that are associated boar taint, based upon the findings that the aldehyde oxidase pathway and CYP2A6 are associated with skatole production.

Thus, the invention relates to genetic markers and methods of identifying those markers in an animal of a particular animal, breed, strain, population, or group, whereby the animal is has increased, decreased or otherwise altered skatole metabolism, and thus boar taint.

Any method of identifying the presence or absence of these markers may be used, including, for example, single-strand conformation polymorphism (SSCP) analysis, base excision sequence scanning (BESS), RFLP analysis, heteroduplex analysis, denaturing gradient gel electrophoresis, and temperature gradient electrophoresis, allelic PCR, ligase chain reaction direct sequencing, mini sequencing, nucleic acid hybridization, micro-array-type detection of genes encoding enzymes involved in skatole metabolism. Also within the scope of the invention includes assaying for protein conformational or sequences changes which occur in the presence of this polymorphism. The polymorphism may or may not be the causative mutation but will be indicative of the presence of this change and one may assay for the genetic or protein bases for the phenotypic difference.

The following is a general overview of techniques which can be used to assay for the genetic marker of the invention.

In the present invention, a sample of genetic material is obtained from an animal. Samples can be obtained from blood, tissue, semen, etc. Generally, peripheral blood cells are used as the source, and the genetic material is DNA. A sufficient amount of cells are obtained to provide a sufficient amount of DNA for analysis. This amount will be known or readily determinable by those skilled in the art. The DNA is isolated from the blood cells by techniques known to those skilled in the art.

Isolation and Amplification of Nucleic Acid

Samples of genomic DNA are isolated from any convenient source including saliva, buccal cells, hair roots, blood, cord blood, amniotic fluid, interstitial fluid, peritoneal fluid, chorionic villus, and any other suitable cell or tissue sample with intact interphase nuclei or metaphase cells. The cells can be obtained from solid tissue as from a fresh or preserved organ or from a tissue sample or biopsy. The sample can contain compounds which are not naturally intermixed with the biological material such as preservatives, anticoagulants, buffers, fixatives, nutrients, antibiotics, or the like.

Methods for isolation of genomic DNA from these various sources are described in, for example, Kirby, *DNA Fingerprinting, An Introduction*, W. H. Freeman & Co. New York (1992). Genomic DNA can also be isolated from cultured primary or secondary cell cultures or from transformed cell lines derived from any of the aforementioned tissue samples.

Samples of animal RNA can also be used. RNA can be isolated from tissues expressing the gene as described in Sambrook et al., supra. RNA can be total cellular RNA, mRNA, poly A+ RNA, or any combination thereof. For best results, the RNA is purified, but can also be unpurified cytoplasmic RNA. RNA can be reverse transcribed to form DNA which is then used as the amplification template, such that the PCR indirectly amplifies a specific population of RNA transcripts. See, e.g., Sambrook, supra, Kawasaki et al., Chapter 8 in *PCR Technology*, (1992) supra, and Berg et al., *Hum. Genet.* 85:655–658 (1990).

PCR Amplification

The most common means for amplification is polymerase chain reaction (PCR), as described in U.S. Pat. Nos. 4,683,195; 4,683,202; and 4,965,188 each of which is hereby incorporated by reference. If PCR is used to amplify the target regions in blood cells, heparinized whole blood should be drawn in a sealed vacuum tube kept separated from other samples and handled with clean gloves. For best results, blood should be processed immediately after collection; if this is impossible, it should be kept in a sealed container at 4° C. until use. Cells in other physiological fluids may also be assayed. When using any of these fluids, the cells in the fluid should be separated from the fluid component by centrifugation.

Tissues should be roughly minced using a sterile, disposable scalpel and a sterile needle (or two scalpels) in a 5 mm Petri dish. Procedures for removing paraffin from tissue sections are described in a variety of specialized handbooks well known to those skilled in the art.

To amplify a target nucleic acid sequence in a sample by PCR, the sequence must be accessible to the components of the amplification system. One method of isolating target DNA is crude extraction which is useful for relatively large samples. Briefly, mononuclear cells from samples of blood, amniocytes from amniotic fluid, cultured chorionic villus cells, or the like are isolated by layering on a sterile Ficoll-Hypaque gradient by standard procedures. Interphase cells are collected and washed three times in sterile phosphate buffered saline before DNA extraction. If testing DNA from peripheral blood lymphocytes, an osmotic shock (treatment of the pellet for 10 sec with distilled water) is suggested, followed by two additional washings if residual red blood cells are visible following the initial washes. This will prevent the inhibitory effect of the heme group carried by hemoglobin on the PCR reaction. If PCR testing is not performed immediately after sample collection, aliquots of $10^6$ cells can be pelleted in sterile Eppendorf tubes and the dry pellet frozen at $-20°$ C. until use.

The cells are resuspended ($10^6$ nucleated cells per 100 µl) in a buffer of 50 mM Tris-HCl (pH 8.3), 50 mM KCl 1.5 mM $MgCl_2$, 0.5% Tween 20, and 0.5% NP40 supplemented with 100 µg/ml of proteinase K. After incubating at 56° C. for 2 hr. the cells are heated to 95° C. for 10 min to inactivate the proteinase K and immediately moved to wet ice (snap-cool). If gross aggregates are present, another cycle of digestion in the same buffer should be undertaken. Ten µl of this extract is used for amplification.

When extracting DNA from tissues, e.g., chorionic villus cells or confluent cultured cells, the amount of the above mentioned buffer with proteinase K may vary according to the size of the tissue sample. The extract is incubated for 4–10 hrs at 50°-60° C. and then at 95° C. for 10 minutes to inactivate the proteinase. During longer incubations, fresh proteinase K should be added after about 4 hr at the original concentration.

When the sample contains a small number of cells, extraction may be accomplished by methods as described in Higuchi, "Simple and Rapid Preparation of Samples for PCR", in *PCR Technology*, Ehrlich, H. A. (ed.), Stockton Press, New York, which is incorporated herein by reference. PCR can be employed to amplify target regions in very small numbers of cells (1000–5000) derived from individual colonies from bone marrow and peripheral blood cultures. The cells in the sample are suspended in 20 µl of PCR lysis buffer (10 mM Tris-HCl (pH 8.3), 50 mM KCl, 2.5 mM $MgCl_2$, 0.1 mg/ml gelatin, 0.45% NP40, 0.45% Tween 20) and frozen until use. When PCR is to be performed, 0.6 µl of proteinase K (2 mg/ml) is added to the cells in the PCR lysis buffer. The sample is then heated to about 60° C. and incubated for 1 hr. Digestion is stopped through inactivation of the proteinase K by heating the samples to 95° C. for 10 min and then cooling on ice.

A relatively easy procedure for extracting DNA for PCR is a salting out procedure adapted from the method described by Miller et al., *Nucleic Acids Res.* 16:1215 (1988), which is incorporated herein by reference. Mononuclear cells are separated on a Ficoll-Hypaque gradient. The cells are resuspended in 3 ml of lysis buffer (10 mM Tris-HCl, 400 mM NaCl, 2 mM $Na_2$ EDTA, pH 8.2). Fifty µl of a 20 mg/ml solution of proteinase K and 150 µl of a 20% SDS solution are added to the cells and then incubated at 37° C. overnight. Rocking the tubes during incubation will improve the digestion of the sample. If the proteinase K digestion is incomplete after overnight incubation (fragments are still visible), an additional 50 µl of the 20 mg/ml proteinase K solution is mixed in the solution and incubated for another night at 37° C. on a gently rocking or rotating platform. Following adequate digestion, one ml of a 6M NaCl solution is added to the sample and vigorously mixed. The resulting solution is centrifuged for 15 minutes at 3000 rpm. The pellet contains the precipitated cellular proteins, while the supernatant contains the DNA. The supernatant is removed to a 15 ml tube that contains 4 ml of isopropanol. The contents of the tube are mixed gently until the water and the alcohol phases have mixed and a white DNA precipitate has formed. The DNA precipitate is removed and dipped in a solution of 70% ethanol and gently mixed. The DNA precipitate is removed from the ethanol and air-dried. The precipitate is placed in distilled water and dissolved.

Kits for the extraction of high-molecular weight DNA for PCR include a Genomic Isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, N.H.), DNA Extraction Kit (Stratagene, Lajolla, Calif.), TurboGen Isolation Kit (Invitrogen, San Diego, Calif.), and the like. Use of these kits according to the manufacturer's instructions is generally acceptable for purification of DNA prior to practicing the methods of the present invention.

The concentration and purity of the extracted DNA can be determined by spectrophotometric analysis of the absorbance of a diluted aliquot at 260 nm and 280 nm. After extraction of the DNA, PCR amplification may proceed. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In a particularly useful embodiment of PCR amplification, strand separation is achieved by heating the reaction to a sufficiently high temperature for a sufficient time to cause the denaturation of the duplex but not to cause an irreversible denaturation of the polymerase (see U.S. Pat. No. 4,965,188, incorporated herein by reference). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, *CSH-Quantitative*

*Biology*, 43:63–67; and Radding, 1982, *Ann. Rev. Genetics* 16:405–436, each of which is incorporated herein by reference).

Template-dependent extension of primers in PCR is catalyzed by a polymerizing agent in the presence of adequate amounts of four deoxyribonucleotide triphosphates (typically dATP, dGTP, dCTP, and dTTP) in a reaction medium comprised of the appropriate salts, metal cations, and pH buffering systems. Suitable polymerizing agents are enzymes known to catalyze template-dependent DNA synthesis. In some cases, the target regions may encode at least a portion of a protein expressed by the cell. In this instance, MRNA may be used for amplification of the target region. Alternatively, PCR can be used to generate a cDNA library from RNA for further amplification, the initial template for primer extension is RNA. Polymerizing agents suitable for synthesizing a complementary, copy-DNA (cDNA) sequence from the RNA template are reverse transcriptase (RT), such as avian myeloblastosis virus RT, Moloney murine leukemia virus RT, or *Thermus thermophilus* (Tth) DNA polymerase, a thermostable DNA polymerase with reverse transcriptase activity marketed by Perkin Elmer Cetus, Inc. Typically, the genomic RNA template is heat degraded during the first denaturation step after the initial reverse transcription step leaving only DNA template. Suitable polymerases for use with a DNA template include, for example, *E. coli* DNA polymerase I or its Klenow fragment, T4 DNA polymerase, Tth polymerase, and Taq polymerase, a heat-stable DNA polymerase isolated from *Thermus aquaticus* and commercially available from Perkin Elmer Cetus, Inc. The latter enzyme is widely used in the amplification and sequencing of nucleic acids. The reaction conditions for using Taq polymerase are known in the art and are described in Gelfand, 1989, *PCR Technology*, supra.

Allele Specific PCR

Allele-specific PCR differentiates between target regions differing in the presence of absence of a variation or polymorphism. PCR amplification primers are chosen which bind only to certain alleles of the target sequence. This method is described by Gibbs, *Nucleic Acid Res.* 17:12427–2448 (1989).

Allele Specific Oligonucleotide Screening Methods

Further diagnostic screening methods employ the allele-specific oligonucleotide (ASO) screening methods, as described by Saiki et al., *Nature* 324:163–166 (1986). Oligonucleotides with one or more base pair mismatches are generated for any particular allele. ASO screening methods detect mismatches between variant target genomic or PCR amplified DNA and non-mutant oligonucleotides, showing decreased binding of the oligonucleotide relative to a mutant oligonucleotide. Oligonucleotide probes can be designed so that under low stringency, they will bind to both polymorphic forms of the allele, but at high stringency, bind to the allele to which they correspond. Alternatively, stringency conditions can be devised in which an essentially binary response is obtained, i.e., an ASO corresponding to a variant form of the target gene will hybridize to that allele, and not to the wild-type allele.

Ligase Mediated Allele Detection Method

Target regions of a test subject's DNA can be compared with target regions in unaffected and affected family members by ligase-mediated allele detection. See Landegren et al., *Science* 241:107–1080 (1988). Ligase may also be used to detect point mutations in the ligation amplification reaction described in Wu et al., *Genomics* 4:560–569 (1989).

The ligation amplification reaction (LAR) utilizes amplification of specific DNA sequence using sequential rounds of template dependent ligation as described in Wu, supra, and Barany, *Proc. Nat. Acad. Sci.* 88:189–193 (1990).

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature ($T_m$). Melting domains are at least 20 base pairs in length, and may be up to several hundred base pairs in length.

Differentiation between alleles based on sequence specific melting domain differences can be assessed using polyacrylamide gel electrophoresis, as described in Chapter 7 of Erlich, ed., *PCR Technology*, "Principles and Applications for DNA Amplification", W. H. Freeman and Co., New York (1992), the contents of which are hereby incorporated by reference.

Generally, a target region to be analyzed by denaturing gradient gel electrophoresis is amplified using PCR primers flanking the target region. The amplified PCR product is applied to a polyacrylamide gel with a linear denaturing gradient as described in Myers et al., *Meth. Enzymol.* 155:501–527 (1986), and Myers et al., in *Genomic Analysis, A Practical Approach*, K. Davies Ed. IRL Press Limited, Oxford, pp. 95–139 (1988), the contents of which are hereby incorporated by reference. The electrophoresis system is maintained at a temperature slightly below the Tm of the melting domains of the target sequences.

In an alternative method of denaturing gradient gel electrophoresis, the target sequences may be initially attached to a stretch of GC nucleotides, termed a GC clamp, as described in Chapter 7 of Erlich, supra. Preferably, at least 80% of the nucleotides in the GC clamp are either guanine or cytosine. Preferably, the GC clamp is at least 30 bases long. This method is particularly suited to target sequences with high $T_m$'s.

Generally, the target region is amplified by the polymerase chain reaction as described above. One of the oligonucleotide PCR primers carries at its 5' end, the GC clamp region, at least 30 bases of the GC rich sequence, which is incorporated into the 5' end of the target region during amplification. The resulting amplified target region is run on an electrophoresis gel under denaturing gradient conditions as described above. DNA fragments differing by a single base change will migrate through the gel to different positions, which may be visualized by ethidium bromide staining.

Temperature Gradient Gel Electrophoresis

Temperature gradient gel electrophoresis (TGGE) is based on the same underlying principles as denaturing gradient gel electrophoresis, except the denaturing gradient is produced by differences in temperature instead of differences in the concentration of a chemical denaturant. Standard TGGE utilizes an electrophoresis apparatus with a temperature gradient running along the electrophoresis path. As samples migrate through a gel with a uniform concentration of a chemical denaturant, they encounter increasing temperatures. An alternative method of TGGE, temporal temperature gradient gel electrophoresis (TTGE or tTGGE) uses a steadily increasing temperature of the entire electrophoresis gel to achieve the same result. As the samples migrate through the gel the temperature of the entire gel increases, leading the samples to encounter increasing temperature as they migrate through the gel. Preparation of samples, including PCR amplification with incorporation of a GC clamp, and visualization of products are the same as for denaturing gradient gel electrophoresis.

Single-Strand Conformation Polymorphism Analysis

Target sequences or alleles at the chosen boar taint loci can be differentiated using single-strand conformation polymorphism analysis, which identifies base differences by alteration in electrophoretic migration of single-stranded PCR products, as described in Orita et al., *Proc. Nat. Acad. Sci.* 85:2766–2770 (1989). Amplified PCR products can be generated as described above, and heated or otherwise denatured, to form single-stranded amplification products. Single-stranded nucleic acids may refold or form secondary structures which are partially dependent on the base sequence. Thus, electrophoretic mobility of single-stranded amplification products can detect base-sequence difference between alleles or target sequences.

Chemical or Enzymatic Cleavage of Mismatches

Differences between target sequences can also be detected by differential chemical cleavage of mismatched base pairs, as described in Grompe et al., *Am. J. Hum. Genet.* 48:212–222 (1991). In another method, differences between target sequences can be detected by enzymatic cleavage of mismatched base pairs, as described in Nelson et al., *Nature Genetics* 4:11–18 (1993). Briefly, genetic material from an animal and an affected family member may be used to generate mismatch free heterohybrid DNA duplexes. As used herein, "heterohybrid" means a DNA duplex strand comprising one strand of DNA from one animal, and a second DNA strand from another animal, usually an animal differing in the phenotype for the trait of interest. Positive selection for heterohybrids free of mismatches allows determination of small insertions, deletions or other polymorphisms that may be associated with polymorphisms.

Non-Gel Systems

Other possible techniques include non-gel systems such as TAQMAN™ (Perkin Elmer). In this system, oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete, i.e., there is a mismatch of some form, the cleavage of the dye does not take place. Thus, only if the nucleotide sequence of the oligonucleotide probe is completely complimentary to the template molecule to which it is bound will quenching be removed. A reaction mix can contain two different probe sequences each designed against different alleles that might be present thus allowing the detection of both alleles in one reaction.

Yet another technique includes an Invader Assay, which includes isothermic amplification that relies on a catalytic release of fluorescence. See Third Wave Technology at www.twt.com.

Non-PCR Based DNA Diagnostics

The identification of a DNA sequence linked to sequences encoding enzymes involved in skatole metabolism can be made without an amplification step, based on polymorphisms including restriction fragment length polymorphisms in an animal and a family member. Hybridization probes are generally oligonucleotides which bind through complementary base pairing to all or part of a target nucleic acid. Probes typically bind target sequences lacking complete complementarity with the probe sequence depending on the stringency of the hybridization conditions. The probes are preferably labeled directly or indirectly, such that by assaying for the presence or absence of the probe, one can detect the presence or absence of the target sequence. Direct labeling methods include radioisotope labeling, such as with $p^{32}$ or $S^{35}$. Indirect labeling methods include fluorescent tags, biotin complexes which may be bound to avidin or streptavidin, or peptide or protein tags. Visual detection methods include photoluminescents, Texas red, rhodamine and its derivatives, red leuco dye and 3,3',5,5'-tetramethylbenzidine (TMB), fluorescein, and its derivatives, dansyl, umbelliferone and the like or with horse radish peroxidase, alkaline phosphatase and the like.

Hybridization probes include any nucleotide sequence capable of hybridizing to the porcine chromosome where the CYP2A6 gene or other gene involved in skatole metabolism resides, and thus defining a genetic marker linked to the gene, including a restriction fragment length polymorphism, a hypervariable region, repetitive element, or a variable number tandem repeat. Hybridization probes can be any gene or a suitable analog. Further suitable hybridization probes include exon fragments or portions of cDNAs or genes known to map to the relevant region of the chromosome.

Preferred tandem repeat hybridization probes for use according to the present invention are those that recognize a small number of fragments at a specific locus at high stringency hybridization conditions, or that recognize a larger number of fragments at that locus when the stringency conditions are lowered.

One or more additional restriction enzymes and/or probes and/or primers can be used. Additional enzymes, constructed probes, and primers can be determined by routine experimentation by those of ordinary skill in the art and are intended to be within the scope of the invention.

According to the invention, polymorphisms in genes encoding enzymes involved in skatole metabolism have been identified which have an association with boar taint. The presence or absence of the markers, in one embodiment may be assayed by PCR-RFLP analysis using the restriction endonucleases and amplification primers may be designed using analogous human, pig or other sequences due to the high homology in the region surrounding the polymorphisms, or may be designed using known gene sequence data as exemplified in GenBank or even designed from sequences obtained from linkage data from closely surrounding genes based upon the teachings and references herein. The sequences surrounding the polymorphism will facilitate the development of alternate PCR tests in which a primer of about 4–30 contiguous bases taken from the sequence immediately adjacent to the polymorphism is used in connection with a polymerase chain reaction to greatly amplify the region before treatment with the desired restriction enzyme. The primers need not be the exact complement; substantially equivalent sequences are acceptable. The design of primers for amplification by PCR is known to those of skill in the art and is discussed in detail in Ausubel (ed.), *Short Protocols in Molecular Biology*, 4th Edition, John Wiley and Sons (1999).

The following is a brief description of primer design.

Primer Design Strategy

Increased use of polymerase chain reaction (PCR) methods has stimulated the development of many programs to aid in the design or selection of oligonucleotides used as primers for PCR. Four examples of such programs that are freely available via the Internet are: PRIMER by Mark Daly and Steve Lincoln of the Whitehead Institute (UNIX, VMS, DOS, and Macintosh), Oligonucleotide Selection Program (OSP) by Phil Green and LaDeana Hiller of Washington University in St. Louis (UNIX, VMS, DOS, and Macintosh), PGEN by Yoshi (DOS only), and Amplify by Bill Engels of the University of Wisconsin (Macintosh only). Generally these programs help in the design of PCR primers by searching for bits of known repeated-sequence elements and then optimizing the $T_m$ by analyzing the length and GC content of a putative primer. Commercial software is also available and primer selection procedures are rapidly being included in most general sequence analysis packages.

Sequencing and PCR Primers

Designing oligonucleotides for use as either sequencing or PCR primers requires selection of an appropriate sequence that specifically recognizes the target, and then testing the sequence to eliminate the possibility that the oligonucleotide will have a stable secondary structure. Inverted repeats in the sequence can be identified using a repeat-identification or RNA-folding program such as those described above. If a possible stem structure is observed, the sequence of the primer can be shifted a few nucleotides in either direction to minimize the predicted secondary structure. The sequence of the oligonucleotide should also be compared with the sequences of both strands of the appropriate vector and insert DNA. Obviously, a sequencing primer should only have a single match to the target DNA. It is also advisable to exclude primers that have only a single mismatch with an undesired target DNA sequence. For PCR primers used to amplify genomic DNA, the primer sequence should be compared to the sequences in the GenBank database to determine if any significant matches occur. If the oligonucleotide sequence is present in any known DNA sequence or, more importantly, in any known repetitive elements, the primer sequence should be changed.

The methods and materials of the invention may also be used more generally to evaluate pig DNA, genetically type individual pigs, and detect genetic differences in pigs. In particular, a sample of pig genomic DNA may be evaluated by reference to one or more controls to determine if a polymorphism in the particular gene is present. Preferably, RFLP analysis is performed with respect to the pig gene, and the results are compared with a control. The control is the result of a RFLP analysis of the pig gene of a different pig where the polymorphism(s) of the pig gene is/are known. Similarly, the genotype of a pig may be determined by obtaining a sample of its genomic DNA, conducting RFLP analysis of the gene in the DNA, and comparing the results with a control. Again, the control is the result of RFLP analysis of the gene of a different pig. The results genetically type the pig by specifying the polymorphism(s) in its genes. Finally, genetic differences among pigs can be detected by obtaining samples of the genomic DNA from at least two pigs, identifying the presence or absence of a polymorphism in the gene, and comparing the results.

These assays are useful for identifying the genetic markers relating to boar taint, as discussed above, for identifying other polymorphisms in the genes encoding enzymes involved in skatole metabolism and for the general scientific analysis of pig genotypes and phenotypes.

The examples and methods herein disclose certain gene(s) which has been identified to have a polymorphism(s) which is associated either positively or negatively with a beneficial trait that will have an effect on meat quality, heavy muscling, and/or skeletal muscle cramping disease for animals carrying this polymorphism. The identification of the existence of a polymorphism within a gene is often made by a single base alternative that results in a restriction site in certain allelic forms. A certain allele, however, as demonstrated and discussed herein, may have a number of base changes associated with it that could be assayed for which are indicative of the same polymorphism (allele). Further, other genetic markers or genes may be linked to the polymorphisms disclosed herein so that assays may involve identification of other genes or gene fragments, but which ultimately rely upon genetic characterization of animals for the same polymorphism. Any assay which sorts and identifies animals based upon the allelic differences disclosed herein are intended to be included within the scope of this invention. One of skill in the art, once a polymorphism has been identified and a correlation to a particular trait established will understand that there are many ways to genotype animals for this polymorphism. The design of such alternative tests merely represents optimization of parameters known to those of skill in the art and is intended to be within the scope of this invention as fully described herein.

Example 5

Cloning, Expression and Functional Characterization of Cytochrome P450 2A6 Gene from Pig Liver Entire male pigs are used for meat production in pig industry, due to a better feed conversion, improved carcass leanness and addressed animal welfare. Therefore, raising male pigs may improve the profitability of pork production by up to 30% (Babol et al. 1995). However, the frequent occurrence of off-odors in cooked pork from uncastrated male pigs, commonly known as "boar taint", is highly objectionable to consumers. Skatole is one of the major contributors to boar taint (Gonzalo et al. 2000). Skatole is absorbed from the gut and then metabolized primarily in the liver. In pigs, cytochrome P450 enzymes have been found to have significant impact on metabolism of skatole. It has been shown that CYP2A6 is one of major key enzymes in the metabolism of skatole (Gonzalo el al. 2000). In pigs, CYP2A6 has been found to be highly and negatively correlated with skatole accumulation in fat (Babol et al. 1998; Gonzalo et al. 2000). Therefore CYP2A6 plays an important role in the metabolism and clearance of skatole from the body in pigs.

Cytochrome P450 is a superfamily of hemoprotein (Ingelman-Sundberg et al 1999). In human, CYP2A6 is predominantly expressed in the liver (Koskela et al. 1999; Oscarson, 2001). It is a major hepatic member of the family, which metabolizes pharmaceutical (Miles et al. 1990) and many other drugs and environment chemicals (Yamazaki et al 1992). In human, CYP2A6 was first identified as the coumarin-7 hydroxylase (Yamano et al., 1990), and has received a lot of attention since then, due to its principle role in nicotine C-oxidation and possible involvement in smoking behavior and lung cancer susceptibility (Xu et al., 2002; Oscarson, 2001). The knowledge concerning CYP2A6 in human has substantially increased. However, the information about the CYP2A6 gene, its expression and how a genetic variant of CYP2A6 affect skatole level in pigs is remains empty.

In present study, we constructed the cDNA library from pig liver by rapid amplification of cDNA ends (RACE) method and reported the sequence of porcine CYP2A6 cDNA. We examined the expression pattern of the CYP2A6 mRNA species in different tissues in pigs by Northern analysis. Polymerase chain reaction technique combined with single strand conformational polymorphism (PCR-SSCP) was used to scan and identify any genetic polymorphism of CYP2A6 coding region from porcine liver tissues, which may alter the metabolic capacities of the enzyme. Furthermore, functional studies with this genetic polymorphism of CYP2A6 were carried out.

Tissue Samples

Liver tissues were obtained from a male pig for construction of cDNA library. To identify any genetic polymorphism in CYP2A6, sixty-nine pigs from a variety of breeds, including Yorkshire, Duroc, Landrace, and Pietrain, as well as crosses between Landrace and Duroc, Large White and Duroc, and Large White and Pertain, were slaughtered at an average live weight of 144 kg (144 kg±33) at the Department of Animal and Poultry Science abattoir. A sample of liver was taken immediately following exsanguinations, frozen in liquid nitrogen and stored at −70° C. for until use.

Isolation of Total RNA

One hundred milligram of tissue samples were homogenized in 1 ml of Tri-Reagent (Sigma) and incubated for 10 min at room temperature. After incubation, 0.2 ml of chloroform was added and vortexed. The samples were centrifuged at 12,000×g for 10 min at 4° C. and then aqueous phase was transferred in to a sterile tube. The aqueous phase was mixed with 0.5 ml of isopropanol and incubated at room temperature for 10 min to precipitate the RNA. Pellet was obtained by centrifugation (12,000×g for 10 min at 4° C.). The pellet was washed with 75% ethanol and then suspended into 50 µl of DEPC water.

Construction and Screening of a Pig cDNA RACE Library

5' and 3' rapid amplification of cDNAs (RACE) were constructed from 1 µg of total RNA from liver separately by use of Smart RACE cDNA Amplification kit (Clontech), and used as templates in the subsequent PCR screening of porcine CYP2A6. The 5'RACE was performed by synthesizing the first strand cDNA with a modified lock-docking oligo (dT) primer and then tailing the product 5'AAG CAG TGG TAT CAA CGC AGA GTA CGC GGG 3'(SEQ ID NO:9) (anchor primer) in 5' end via terminal transferase. The 3'RACE was performed with oligo (dT) primer but includes the same lock-docking nucleotide positions as in 5'RACE. The first fragment of CYP2A6 was amplified with the primers designed from the conserved region of human 2A6, mouse 2A5, and rat 2A3 cDNA sequence. The forward primer is 5'AGG ACA AAG AGT TCC TGT CAC TG 3', (SEQ ID NO:10) reverse primer is 5'CAA TCT CCT CAT GGA CCT TGG 3'(SEQ ID NO: 11). To obtain full-length porcine CYP2A6, following primers were used in the subsequent PCR-based screening: 5'ATG AGC AGC AGG AAG CCG TAG 3'(SEQ ID NO:12) and anchor primer with 5'Race as a template; 5'CTA CGG CTT CCT GCT GCT CAT 3'(SEQ ID NO:13) and anchor primer with 3'Race as a template; 5'CAC AAC GAT GCG CTA CGG CT 3'(SEQ ID NO:14) and 5'GCAGGAAGCTCATGGTGTAG 3'(SEQ ID NO:15) with either 3' or 5'Race as a template. The PCR consisted of 35 cycles of denaturing for 1 minute at 94° C., optimal annealing for 1 minute, and extending for 1 minute, with a final 10 minutes extension step at 72° C. 10 µl of the PCR products were analyzed by electrophoresis on a 1% agarose gel.

Colony Hybridization

When there were multiple bands to be amplified from both 3' and 5'Race templates, the PCR products were cloned into pGEM-T Easy Vector System (Promega), and then subjected to colonies hybridization to confirm the specificity of amplified fragment prior to DNA sequencing. Colonies were lifted up to positively charged nylon membrane (Roche), then subjected to lysis and fixation in 0.5M NaCl for 5 minutes, rinsing in 5×SSC for 1 minutes, and air dry; Colonies hybridization was performed with ECL nucleotide DNA labeling and detection kit (Amersham Life Science). The probe used in the hybridization was the fragment first amplified by the primers designed from the human 2A6, mouse 2A5, and rat 2A3 cDNA conserved region. After hybridization overnight at 42° C., the membrane was washed with 0.15×SSC for 20 minutes twice and exposed to x-ray film (Kodak). The colony that gives the strongest signal is subjected to be sequencing.

Isolation of Full-Length Porcine CYP2A6 cDNA

To obtain full-length porcine CYP2A6 sequence, forward primer 5'CTC GCA GTG CCA CCA TGC TG 3'(SEQ ID NO:16) and reverse primer 5'GCA GGA AGC TCA TGG TGT AGG TC (SEQ ID NO: 17) 3' were designed based on the sequence obtained from the 5' and 3'RACE, and used to amplify the full-length porcine CYP 2A6 either with 5' or 3'RACE cDNA as a template. PCR profile was 3 min at 94° C., followed by 35 cycles of 1 min at 94° C., 1 min 30 sec at 64° C., 2 min at 72° C. and final extension of 10 min at 72° C. and two drops of mineral oil were added. The PCR fragment was cloned into T-Easy vector (Promega) and subjected to sequence analysis.

Northern Blot Analysis

Total RNAs were isolated from porcine spleen, thymus, liver, lung, muscle, ovary, kidney, small intestine, heart, and testis tissues with Tri-Reagent (Sigma). 20 µg of total RNA from each tissue was subjected to electrophoresis in the 2.0M formaldehyde-containing 1% agarose gel and transferred to nylon membrane (Amersham Pharmacia Biotech) with downward capillary. Full-length of the porcine CYP2A6 (1498 bp) was created from forward primer 5'CTC GCA GTG CCA CCA TGC TG 3'(SEQ ID NO:16) and reverse primer 5'GCA GGA AGC TCA TGG TGT AGG TC 3'(SEQ ID NO:17) from pig liver cDNA library we created. CYP2A6 eDNA was labeled using random primers with digoxigenin-dUTP (Roche Molecular Biochemicals) and hybridized at 50° C. overnight. After prewashing with 2×SSC containing 0.1% SDS, the membrane was washed with 0.2×SSC containing 0.1% SDS for 15 minutes twice at 67°. The hybridized probes are immunodetected with anti-digoxigenin-alkaline phosphatase conjugate, detected with the colorimetric substrates (DIG, Roche), and exposed to Kodak Scientific Imaging film (Kodak) for 1 hour at room temperature.

Sequencing Analysis

The PCR fragments were ligated into pGEM-T Easy Vector System (Promega), and then transformed into competent DH5α cells. DNAs were purified and subject to sequencing using an Applied Biosystems model ABI 377 DNA sequencer.

RT-PCR

To scan any genetic polymorphism in the CYP2A6 from individuals, RT-PCR products that cover its whole coding region were amplified and then subjected to SSCP analysis. First strand cDNA was synthesized from 1 to 5 μg of total RNA from liver samples using SuperScript reverse transcriptase (Invitrogen) and oligo (dT) primer (Sigma). Following the reverse transcription, 2.5 μl of the first strand cDNA was used as the template for PCR. The PCR mixtures (50 ul) contained 1×PCR buffer (100 mM Tris-HCl, pH 8.3; 500 mM KCl, 11 mM MgCl$_2$, 0.1% gelatin), 0.2 mM dNTP, 0.4 mM primers (forward and reverse primer) and 2.5 U of Red Taq polymerase (Sigma). The primer pair (forward primer, 5'CTC GCA GTG CCA CCA TGC TG 3', (SEQ ID NO:16) reverse sequence, 5'GCA GGA AGC TCA TGG TGT AGG TC 3') (SEQ ID NO:17) was designed to amplify the entire coding region of porcine CYP2A6, based on our isolated CYP2A6 (GenBank accession number AY091516). The PCR profile was 3 min at 94° C., followed by 35 cycles of 1 min at 94° C., 1 min at 65° C., 1 min at 72° C. and final extension of 10 min at 72° C.

Single-Strand Conformational Polymorphism Analysis

PCR products were first cut into fragments with BstxI enzyme, and then resolved by SSCP analysis. 5 μl of PCR product amplified was digested with BstxI in 20 μl reaction at 37° C. for 3 hours. A total of 7 μl of digested fragments were then diluted with 13 μl of loading buffer (10% of Sucrose, 0.01% of Bromophenol blue and 0.01% of Xylene cyanol FF). Each digestion reaction was denatured at 100° C. for 5 min, chilled on ice and resolved on 10% of polyacrylamide gel. The electrophoresis was carried in a vertical unit (Bio-Rad Laboratories, 130×160×1.0 mm), in 0.6×TBE buffer for 17 hours at 15° C. at 160 V. The gels were then silver stained.

CYP2A6 Activity

CYP2A6 activity is assayed by measurement of coumarin 7-hydroxylase activity on pig liver microsomal samples. 20 μl of microsomal suspension containing 0.4 mg microsomal protein were mixed with 200 μl of coumarin hydroxylase reaction mix (0.05M Tris buffer pH 7.4, 5 mM MgCl$_2$ and 0.2 mM coumarin). The reaction was started by adding 15 μl of 25 mM NADPH. After incubation at 37° C. for 15 minutes, the reaction was stopped by the addition of 50 μl of 20% trichloroacetic acid, followed by cenrifugation at 10,000 g for 2 min. Two hundred microliters of the supernatant fraction was diluted with 2 ml of 0.1 M Tris buffer (pH 9.0), and the fluorescence was determined at wavelengths of 390 nm for excitation at and 440 nm for emission.

Measurement of Skatole Level in Fat

A backfat sample was collected at the midline point of 11th rib and frozen at −20° C. until assayed for skatole. The skatole content was measured with a colorimetric assay, according to the method described by Gonzalo et al. (2000).

Western Analysis

Liver tissue (1 g) was homogenized in 5 ml of sample buffer (1% cholic acid, 0.1% SDS in PBS buffer) and the protein concentrations of homogenates were determined using the BCA kit (Pierce). 40 μg of total protein were subjected to sodium dodecyl sulphate gel electrophoresis using a 12% polyacrylamide gel. The protein was transferred to a nitro-cellulose filter (BioRad), incubated with mouse anti-human monoclonal 2A6-antibody MAB-2A6 (Gentest), and subsequently anti-mouse IGG peroxidase conjugate developed in goat (Sigma). Immunoreactive bands were stained by a chemiluminescence procedure (ECL, Amersham Life Science) and visualized by autoradiography.

The CYP2A6 cDNA Sequence and Sequence Characterization

Pig CYP2A6 cDNA was isolated by PCR screening of the liver cDNA library constructed with RACE. The nucleotide sequence of the CYP2A6 cDNA was 1519 bp long and contained a 1485 bp-long open reading frame (ORF), which encodes 497 amino acids (FIG. 12). Pig CYP2A6 cDNA sequence was submitted to Genbank database under the accession number AY091516.

The human CYP2A6, mouse CYP2A5, rat CYP2A3 were identified as the coumarin-7 hydroxylase. We compared pig CYP2A6 ORF to above genes, it showed 87% homology to human CYP2A6, 85% to mouse CYP2A5, and 86% to rat 2A3. The deduced amino acid sequence for pig CYP2A6 showed 87% homology to human 2A6, 90% to mouse 2A5, and 89% to rat 2A3 (FIG. 13). In human CYP2A6, Gln104, Phe209 and His477 were reported to be active sites for CYP2A6 coumarin 7-hydroxylase activity, oxidative metabolism of nicotine and cotinine (Lewis et al. 1999). R128 was represents one of key binding residues for human CYP2A6 (Kiragawa et al, 2001; Lewis et al, 1999). All above active sites are conserved in the putative pig CYP2A6.

Expression of CYP2A6 mRNA Species in Various Tissues

Figure 14:
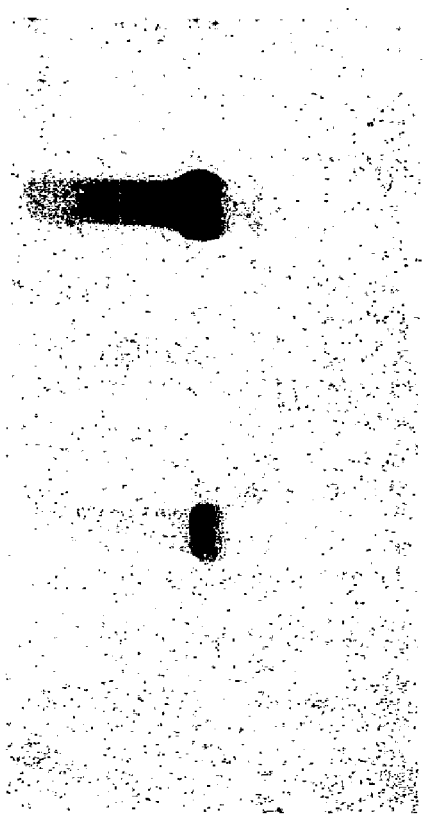
FIG. 14 shows the results of Northern blot analysis of the CYP2A6' expression in different porcine tissues. Total RNAs were extracted from spleen, thymus, liver, lung, muscle, ovary, kidney, small intestine heart and testis, respectively. 20 µg of Total RNA (per lane) were electrophoresed on a 1.0% agarose gel containing 2.0 M formaldehyde. The RNAs were transferred to a nylon membrane and then hybridized with dig-labeled porcine CYP2A6 cDNA.

The expression patterns of CYP2A6 mRNA in various tissues, including spleen, thymus, liver, lung, muscle, ovary, kidney, small intestine heart and testis from pigs, were investigated by Northern blotting by using pig CYP2A6 cDNA as a probe. The result showed that CYP2A6 are only expressed in liver and kidney tissue (FIG. 14). A much higher level of CYP2A6 mRNA was observed in the liver, and a lower level of CYP2A6 mRNA was expressed in the kidney. The result showed the CYP2A6 is predominantly expressed in pig liver tissue. It indicated the liver is the major tissue that plays important role in CYP2A6 metabolism in pigs.

CYP2A6 Genetic Polymorphism

In order to identify any genetic polymorphism of CYP2A6, which may alter the metabolic capacities of the enzyme, polymerase chain reaction technique combined with single strand conformational polymorphism (PCR-SSCP) was used to scan CYP2A6 coding region from porcine liver tissues. In pig, CYP2A6 full-length cDNA was amplified by PCR with primer pair: forward primer 5'CTC GCA GTG CCA CCA TGC TG 3'(SEQ ID NO:16) and reverse primer 5'GCA GGA AGC TCA TGG TGT AGG TC 3'(SEQ ID NO:17) from liver tissues. The resulting PCR products were about 1500 bp in size. Digested PCR products with BstxI were subjected to SSCP analysis using our optimized system. We found that there are several different polymorphisms existing in CYP2A6 coding region (data not shown). Of which, one of deletion that resulted in coding region frame shifting received our most attention. Due to one G missing, the length of ORF region of CYP2A6 changes from 1485 bp to 612 bp. This also causes the length of its encoded gene product change from 495 amino acid to 204 amino acid. It is suggested that the deletion might also result in inactivation of CYP2A6 activity for the individual that contains such deletion. It has been shown that CYP2A6 is one of major key enzymes in the metabolism of skatole (Gonzalo et al. 2000). CYP2A6 is negatively correlated with skatole accumulation in fat (Babol et al. 1998). Therefore, we infer that CYP2A6 activity for the sample that exists such deletion would be zero for its comarin 7-hydroxylase activity due to coding region frame shifting of CYP2A6 gene, and that skatole level should be higher due to losing this enzyme activity to clear skatole from the body.

Figure 15:
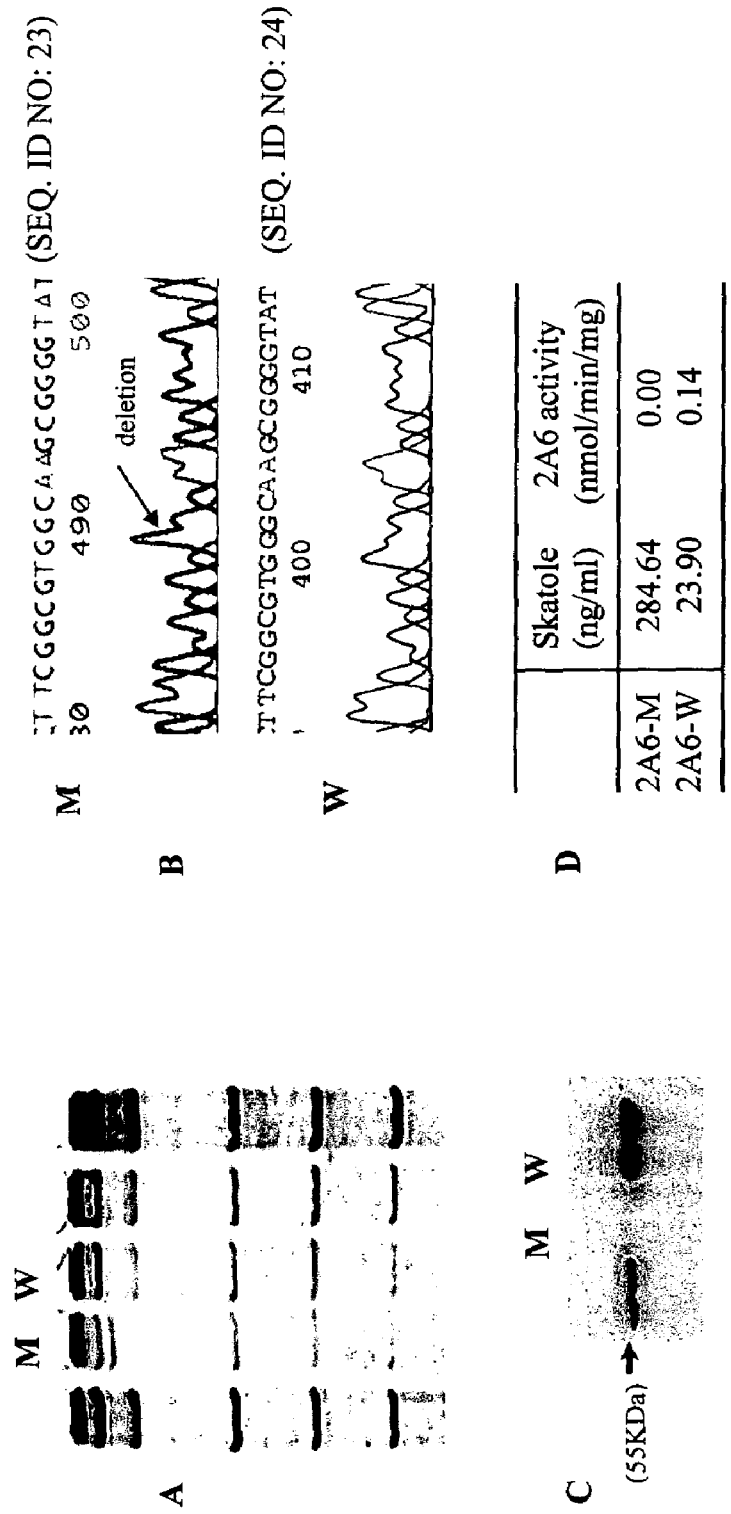
FIG. 15 shows the Genetic polymorphism, sequencing, western blotting analysis, and micosomal enzyme activity and skatole level in fat for CYP2A6 in pig liver. A, PCR-SSCP analysis of CYP2A6 cDNA. M: deletion mutant; W: wild type. B, Sequencing analysis of CYP2A6 for deletion mutant and wild type. M: sequencing data for deletion mutant; W: sequencing data for wild type. C, total proteins from microsome were separated in 12% SDS-PAGE electrophoresis, immunoblotted with mouse anti-human monoclonal 2A6-antibody. Duplicated and 40 µg of total protein from liver microsome was loaded in each lane. M: total protein from individual that has the deletion mutant for CYP2A6; W: total protein from wild type pig liver. D, micosomal CYP2A6 activity and skatole level in fat for both deletion mutant and wild type.

To evaluate above hypothesis and investigate the association of this genetic polymorphism of CYP2A6 with skatole level, the phenotyping using skatole level measurement, coumarin 7-hydroxylase activity assay and immunoblotted with monoclonal anti-human CYP2A6 anti-body (Gentest) for the samples showed different genotype, were further carried out. The results showed that the skatole level is much higher for the sample with deleted mutation than that in wild type samples. Coumarin 7-hydroxylase assay and immunoblotting analysis also told us zero for coumarin 7-hydroxylase activity and negative immunoreactive band for the sample that has deleted mutation, while remaining lower skatole level, higher activity and detectable immunoreactive bands for wild type samples (FIG. 15). The results are strongly supporting our suggestion that the CYP2A6 deletion caused a complete lack of enzymatic activity, and hence caused higher level skatole level in pig.

In human, CPY2A6 gene has been extensively studied; however, the information about the CYP2A6 gene, its expression and how a genetic variant of CYP2A6 affect skatole level in pigs is remains empty. In this study, we reported the molecular cloning, functional characterization of CYP2A6 gene in pig. We designed the primers based on conserved region of human 2A6, mouse 2A5 and rat 2A3 cDNA sequence. Coumarin 7-hydroxylation is catalysed by a high-affinity CYP2A6 and CYP2A5 enzyme in human and mouse (Miles et al., 1990; Donato et al., 2000), and that by CYP2A3 in rat. The formation of 7-hydroxycoumarin has been used as an in vivo and invitro probe for CYP2A6 in human, CYP2A5 in mouse, and 2A3 in rat (Rodrigues et al., 1994; Rautio et al., 1992; Fernandez-Salguero et al, 1995). Therefore, by using the designed primers, we screened out the first fragment, subsequently the whole sequence of pig CYP2A6 cDNA.

The CYP2A6 in human, CYP2A5 in mouse, and CYP2A3 was sequenced (Access number: U22027 for human, BC046605 for mouse, and M33190 for rat), and has been mapped to chromosome 19q13.2 (b: Fernandez-Salguero et al., 1995) chromosome 7 (Kent et al.,1987) and chromosome 1 (STS: D1Mgh28), respectively. As indicated in the results, when comparing pig CYP 2A6 sequence to its orthologous genes, sequence of human CYP2A6, mouse 2A5 and rat CYP2A3, we found that it has high homology to its orthologs both in cDNA sequence and amino acid sequence. And all the important active sites of amino acid sequence in human CYP2A6 are also conserved in our putative pig CYP2A6 sequence. Furthermore, we searched against human, mouse and rat genomic database with pig CYP2A6 cDNA sequence, we found that pig CYP2A6 only hit a human genomic clone (NT_011109) from chromosome 19q13.2, mouse genomic clone (NT_039410) from chromosome 7, and rat genomic clone (NW_043361) from chromosome 1q21, respectively. The hit scores showed that pig CYP2A6 cDNA sequence has highest identity with human CYP2A6 genomic clone (91%) at human chromosome 19q13.2, with mouse 2A5 genomic clone (89%) at mouse chromosome 7, and with rat CYP2A3 genomic clone (88%) at rat chromosome 1q21. All these findings taken together thus led us to conclude that the putative CYP2A6 is indeed pig CYP2A6.

In this study, we performed northern blot analysis for pig CYP2A6 mRNA distribution in different tissues, the results showed that CYP2A6 is expressed predominantly in liver and at a much higher level in liver, lower level in kidney. This indicated liver is the most important tissue for clearance of skatole from body in pig. In spite of high similarities of pig CYP2A6 with its orthologous genes, these enzymes differ in tissue distribution. It has been reported that mRNA expression is observed mainly in liver for human 2A6 (Koskela et al. 1999; Oscarson, 2001), in liver, kidney and small intestine for mouse 2A5 (Su et al., 1998), and in olfactory mucosa and lung for rat 2A3 (Su, et al., 1996; Kimura et al., 1989). In our study, we found that CYP2A6 is not expressed in small intestine and lung in pig. The difference of expression for CYP2A6 mRNA and its orthologous genes in various tissues suggest there might be difference in their promoter region, this difference may be useful for study regulation of tissue-specific gene expression.

In human, CYP2A6 has been one of most important enzyme in nicotine C-oxisation, due to the important of CYP2A6 in nicotine metabolism, and possible involvement in smoking behavior and lung cancer susceptibility (Xu et al., 2002; Oscarson, 2001). Polymorphism in the human CYP2A6 gene may thus impact on both smoking behavior and lung cancer susceptibility. Therefore, substantial efforts have been focused on detecting genetic polymorphism and its consequences (Paschke, et al., 2001; Kamataki, et al., 1999; Oscarson, et al., 2001; Kitagawa, et al., 2001). In human, large interindividual differences has been seen in the levels of CYP2A6 enzyme, due to the genetic variants mainly located in the open reading frame (Nakajima et al., 2002). A number of genetic polymorphisms have been detected for the CYP2A6 in human, including SNPs in the coding region that lead to inactivation, such as Gly479Val (Oscarson et al., 2001) and Arg128Gln (Kitagawa et al., 2001). The progress in such researches will facilitate molecular study to clarify how critical the CYP2A6 polymorphism in causing genetic difference and its subsequent consequence.

The role of cytochrome P450 enzyme including CYP2A6 in the metabolism of skatole has been investigated in human, mouse, and rabbit (Thornton-Manning et al., 1996). In pigs, It has been reported that CYP2A6 is one of key enzymes in the hepatic metabolism of skatole (Gonzalo et al. 2000) and CYP2A6 is negatively correlated with skatole accumulation in fat (Babol et al. 1998). Therefore, pigs with high levels of these enzyme incuding CYP2A6 have low levels of skatole in the fat, since skatole is rapidly metabolised and celared from the body, pigs with low levels of these enzyme can have high levels of skatole in the fat. Therefore, CYP2A6 could be use as an genetic marker to select against skatole, once CYP2A6 genetic variant and its consequence on skatole has been investigated. Because there is no information on CYP2A6 gene, we first isolated pig CYP2A6 from liver tissue using RACE method, then performed PCR-SSCP analysis to scan pig CYP2A6 coding region based on our optimized genotyping system. In this study, we focus our efforts on evaluation of CYP2A6 functional region and its genetic polymorphism. We have identified one genetic polymorphism, resulting in a frame shifting in the coding region and inactivation of the enzyme activity. Due to deletion of CYP2A6, coumarin 7-hydroxylation and CYP2A6 gene product are not detectable. It is not known at which age the unregulation of CYP2A6 occurs. In our CYP2A6 phenotyping studies using coumarin, western analysis with mouse anti-human monoclonal 2A6-antibody, and skatole measurement in pig, we also found that there are the existence of additional alleles outside of coding region that modulate or inactive CYP2A6 activity (data not shown). Therefore, it would be helpful to investigate the promoter region of CYP2A6, in combination with phenotype individuals with either coumarin, immunodectected band as indicators of in vivo and invitro CYP2A6 activity in future study, since there may be other CYP2A6 alleles that have not yet known.

In this study, we isolated pig CYP2A6 cDNA from liver and found the CYP2A6 deletion in ORF region, which resulted in a complete lack of the enzymatic activity. There has been no published study that investigates the impact of genetic polymorphism in CYP2A6 on its clearance of skatole from body in pig. The data presented in this study suggest that the CYP2A6 gene deletion might play an important role in the development of genetic marker for skatole.

REFRENCES

Diaz, G. J. and Squires, E. J. (2000). Metabolism of 3-Methylindole by Porcine Liver Microsomes: Responsible Cytochrome P450 Enzyme. *Toxicological Science* 55, 284–292.

Babol, J., Squires, E. J. and Lundström, K. (1998) Relationship between Oxidation and Conjugation Metabolism of Skatole in Pig Liver and Concentrations of Skatole in Fat. *Journal of Animal Science* 76, 829–838.

Donato, M. T., Viitala, P., Rodriguez-Antona, C., Lindfors, A., Castell, J. V., Raunio, H., Gómez-Lechón, M. J. and Pelkonen, O. (2000) CYP2A5/CYP2A6 expression in mouse and human hepatocytes treated with various in vivo induces. *Drug Metabolism and Disposion* 28, 1321–1326

Fernandez-Salguero, P. and Gonzalez, F. J. (1995) The CYP2A gene subfamily: species differences, regulation, catalytic activities and role in chemical carcinogenesis. *Pharmacogenetics* 5, 123–128

Fernandez-Salguero, P., Hoffman, S. M., Cholerton, S., Mohrenweiser, H., Raunio, H., Rautio, A., Pelkonen, J. D., Humang, W. E., Eeans, J. R. and Idle. (1995) A genetic polymorphism in coumarin 7-hydroxylation: sequence of the human CYP2A genes and identification of variant CYP2A6 alleles. *The American Journal of Human Genetics* 57, 651–660

Ingelman-Sundberg, M., Oscarson, M. and Mclellan, R. A (1999) Polymorphic human cytochrome P450 enzymes: an opportunity for individualized drug treatment. *Trends in Pharmacological Science* 20, 342–349

Kamataki, T., Nunoya, K. I., Sakai, Y., Kushida, H. and Fujita, K. I. (1999) Genetic polymorphism of CYP2A6 in relation to cancer. *Mutation Research* 428, 125–130 Kent, R. B., Fallows, D. A., Geissler, E., Glaser, T., Emanuel, J. R., Lalley, P. A., Levenson, R. and Housman, D. E. (1987) Genes encoding alpha and beta subunits of Na, K-ATPase are located on three different chromosomes in the mouse. *Proceedings of the National Academy of Science, USA* 84, 5369–5373

Kimura, S., Kozak, C. A. and Gonzalez, F. J. (1989) Identification of a novel P450 expression in rat lung: cDNA cloning and sequence, chromosome mapping, and induction by 3-methylcholanthrene. *Biochemistry* 28, 3798–3803

Kitagawa, K., Kunugita, N., Kitagawa, M. and Kawamoto, T. (2001) CYP2A6*6, a novel polymorphism in cytochrome P450 2A6, has a single amino acid substitution (R128Q) that inactivates enzymes. *The Journal of Biological Chemistry* 276, 17830–17835

Koskela, S., Hakkola, J., Hukkanen, J., Pelkonen, O., Sorri, M. and Saranen, A. (1999) Expression of CYP2A gene in human liver and extrahepatic tissue. *Biochemical Pharmacology* 57, 1407–1413

Lewis, D. F. V., Dickins, M., Lake, B. G., Eddershaw, P. J., Tarbit, M. H. and Goldfarb, P. S. (1999) Molecular modeling of the human cytochrome P450 isoform CYP2A6 and investigations of CYP2A substrate selectivity. *Toxicology* 133, 1–33

Miles, J. S., Mclaren, S. W, Forrester, L. M., Glancey, M. J., Lang, M. A. and Wolf, C. R. (1990) Identification of the human liver cytochrome P-450 responsible for coumarin 7-hydroxylase activity. *Biochemistry Journal* 267, 365–371

Nakajima, M., Kuroiwa, Y. and Yokoi, T. (2002) Interindividual differences in nicotine metabolism and genetic polymorphism of human 2A6. *Drug Metabolism Reviews* 34, 865–877

Oscarson, M. (2001) Genetic polymorphisms in cytochrome P450 2A6 (CYP2A6) gene: implications for interindividual differences in nicotine metabolism. *Drug Metabolism and Disposition* 29, 91–95

Paschke, T., Riefler, M., Schuler-Metz, Annette., Wolz, Lucie., Scherer, Gerhard., Mcbride. M. and Bepler, G. (2001) Comparison of cytochrome P450 2A6 polymorphism frequencies in Caucasians and African-Americans using a new one-step PCR-RFLP genotyping method. *Toxicology* 168, 259–268

Rautio, A., Kraul, H., Kojo, A., Salmela, E., Pelkonen, O. (1992) Interindividual variability of coumarin 7-hydroxylation in health individuals. *Pharmacogenetics* 2, 227–233

Rodrigues, A. D. (1994) Use of in vitro human metabolism studies in drug development: an industrial perspective. *Biochemical Pharmacology* 48, 2147–2156

Su, T., He, W. L., Lipinskas, T. W. and Ding, X. (1998) Differential xenobiotic induction of CYP2A5 in mouse liver, kidney, lung, and olfactory mucosa. *Drug Metabolism and Disposition* 26, 822–824

Su, T., Sheng, J. J, Lipinskas, T. W. and Ding, X. (1996) Expression of CYP2A6 genes in rodent and human nasal mucosa. *Drug Metabolism and Disposition* 24, 884–890

Thornton-Manning, J., Appleton, M. L., Gonzalez, F. J., and Yost, G. S. (1996) Metabolism of 3-methylindole by vaccinia-expressed P450 enzymes: correlation of 3-methyleneindolenine formation and protein-binding. *The Journal of Pharmacology and Experimental Therapeutics* 276, 21–29

Xu, C., Goodz, S., Sellers, E. M. and Tyndale, R. F. (2002) CYP2A6 genetic variation and potential consequences. *Advanced Drug Delivery Review* 54, 1245–1256

Yamazaki, H., Inui, Y., Yun, C. H., Guengerich, F. P. and Shimada, T. (1992) Cytochrome P450 2E1 and 2A6 enzymes as major catalysts for metabolic activation of N-nitrosodialkylamines and tobacco-related nitrosamines in human liver microsomes. *Carcinogenesis* 13, 1789–1794.

Yamano, S., Tatsuno, J. and Gonzalez, F. J (1990) The CYP2A3 gene product catalyzes coumarin 7-hydroxylation in human. *Biochemistry* 29, 1322–1329

Aitio, A. (1978) A simple and sensitive assay of 7-ethoxycoumarin deethylation. Anal. Biochem. 85, 488–491.

Albrecht C F, Chorn D J and Wessels P (1989) Detection of 3-hydroxy-3-methyloxindole in human urine. *Life Sci* 45:1119–1126.

Babol J, Squires E J and Lundström K (1998a) Hepatic metabolism of skatole in pigs by cytochrome P4502E1. *J Anim Sci* 76:822–828.

Babol J, Squires E J and Lundström K (1998b) Relationship between oxidation and conjugation metabolism of skatole in pig liver and concentrations of skatole in fat. *J Anim Sci* 76:829–838.

Baek C E, Hansen-Mller J, Friis C and Hansen S H (1995) Identification and quantification of selected metabolites of skatole—possibilities for metabolic profiling of pigs. *Proc. EAAP Working Group Production and Utilisation of Meat from Entire Male Pigs*, Milton Keynes, INRA and MLC.

Baek CE, Hansen-Mller J, Friis C, Cornett C and Hansen S H (1997) Identification of selected metabolites of skatole in plasma and urine from pigs. *J Agric Food Chem* 45:2332–2340.

Beedham, C. (1985) Molybdenum hydroxylases as drug-metabolizing enzymes. *Drug Metab. Rev.*, 16, 119–156.

Beedham, C.; Peet, C. F.; Panoutsopoulos, G. I.; Carter, H.; Smith, J. A. (1995) Role of aldehyde oxidase in biogenic amine metabolism. *Prog. Brain Res.*, 106, 345–353.

Bonneau, M. 1997. Proc. EAAP Working Group on the Production and Utilization of Meat from Entire Male Pigs, Stockholm.

Carlson J R and Yost G S (1989) 3-Methylindole-induced acute lung injury resulting from ruminal fermentation of tryptophan, in *Toxicants of Plant Origin. Volume III. Protein and Amino Acids* (Cheeke P R ed) pp 107–123, CRC Press, Boca Raton.

Claus, R., U. Weiler, and A. Herzog. 1994. Physiological aspects of androstenone and skatole formation in the boar—a review with experimental data. *Meat Sci.* 38:289–305.

Diaz, G. J.; Skordos, K.; Yost, G. S; Squires, E. J. (1999, in press) Identification of Phase I metabolites of 3-methylindole produced by pig liver microsomes. *Drug Metab. Dispos.*

Friis, C. 1993. Distribution, metabolic fate and elimination of skatole in the pig. In: M. Bonneau (Ed.) Measurement and prevention of boar taint in intact male pigs. p 113–115. INRA Edition, Paris.

Frydman R B, Tomaro M L and Frydman B (1972) Pyrrolooxygenases: isolation, properties, and products formed. *Biochim Biophys Acta* 284:63–79.

Hammond A C, Carlson J R and Willett J D (1979) The metabolism and disposition of 3-methylindole in goats. *Life Sci* 25:1301–1306.

Hansen L L, Larsen A E and Hansen-Møller J (1995) Influence of keeping pigs heavily fouled with faeces plus urine on skatole and indole concentration (boar taint) in subcutaneous fat. *Acta Agric Scand* 45:178–185.

Huijzer J C, Adams J D and Yost G S (1987) Decreased pneumotoxicity of deuterated 3-methylindole: bioactivation requires methyl C—H bond breakage. *Toxicol Appl Pharmacol* 90:60–68.

Jensen M T, Cox R P and Jensen B B (1995) Microbial production of skatole in the hind gut of pigs given different diets and its relation to skatole deposition in backfat. *Anim Sci* 61:293–304.

Jepson J B, Zaltzman P and Udenfriend S (1962) Microsomal hydroxylation of tryptamine, indole acetic acid and related compounds, to 6-hydroxy derivatives. *Biochim Biophys Acta* 62:91–102.

Johns, D. G. (1967) Human liver aldehyde oxidase: differential inhibition of oxidation of charged and uncharged substrates. *J. Clin. Invest.*, 46, 1492–1505.

Kende A S and Hodges J C (1982) Regioselective C-3 alkylations of oxindole dianion. *Synth Commun* 12:1–10.

Kjeldsen, N. 1993. Practical experience with production and slaughter of intact male pigs. In: M. Bonneau (Ed.) Measurement and prevention of boar taint in intact male pigs. p 137-144. INRA Edition, Paris.

Krenitsky, T. A.; Tuttle, J. V.; Cattau, E. L. Jr.; Wang, P. (1974) A comparison of the distribution and electron acceptor specificities of xanthine oxidase and aldehyde oxidase. *Comp. Biochem. Physiol.*, 49B, 687–703.

Lundström, K.; Bonneau, M. (1996) Off-flavour in meat with particular emphasis on boar taint. In *Meat Quality and Meat Packaging*; Taylor, S., Raimundo A., Severini, M.; Smulders, F. J. M., Eds., ECCEAMST, Utrecht.

Lundström, K., B. Malmfors, S. Stern, L. Rydhmer, L. Eliasson-Selling, A. B. Mortensen, and H. P. Mortensen. 1994. Skatole levels in pigs selected for high lean tissue growth rate on different protein levels. *Livest. Prod. Sci.* 38:125–132.

Mahon M E and Mattok G L (1967) The differential determination of conjugated hydroxyskatoles in human urine. *Can J Biochem* 45:1317–1322.

Mortensen, A. B.; S.o slashed.rensen, S. E. (1984) Relationship between boar taint and skatole determination with a new analysis method. Proc. 30.sup.th Eur. Mtg. Res. Workers, Bristol. Paper 8–11, p. 395.

National Research Council. (1987) *Vitamin Tolerance of Animals*. National Academy Press, Washington.

Patience, J. F.; Thacker, P. A.; de Lange C. F. M. (1995) *Swine Nutrition Guide*. 2nd Ed. Prairie Swine Centre Inc., Saskatoon.

Rajagopalan, K. V.; Handler, P. (1964) Hepatic aldehyde oxidase. III. The substrate binding site. *J. Biol. Chem.*, 239, 2027–2035.

Rajagopalan, K. V.; Handler, P. (1966) P. Aldehyde oxidase. Methods Enzymol. 9, 364–368.

Rashidi, M. R.; Smith, J. A.; Clarke, S. E.; Beedham, C. (1997) In vitro oxidation of famciclovir and 6-deoxypenciclovir by aldehyde oxidase from human, guinea pig, rabbit, and rat liver. *Drug Metab. Dispos.*, 25, 805–813.

Rodrigues, A. D. (1994) Comparison of levels of aldehyde oxidase with cytochrome P450 activities in human liver in vitro. *Biochem. Pharmacol.*, 48,197–200.

Ruangyuttikarn W, Appleton M L and Yost G S (1991) Metabolism of 3-methylindole in human tissues. *Drug Metab Dispos* 19:977–984.

SAS. (1995) SAS System for Windows (Release 6.11). SAS Institute Inc., Cary, N.C.

Sambrook et al. (1989) Molecular Cloning A Laboratory Manual, 2nd edition, Cold Spring Harbor Laboratory Press Skiles G L and Yost G S (1996) Mechanistic studies on the cytochrome P450-catalyzed dehydrogenation of 3-methylindole. *Chem Res Toxicol* 9:291–297.

Skiles G L, Adams J D and Yost G S (1989) Isolation and identification of 3-hydroxy-3-methyloxindole, the major murine metabolite of 3-methylindole. *Chem Res Toxicol* 2:254–259.

Skordos K W, Skiles G L, Laycock J D, Lanza D L and Yost G S (1998a) Evidence supporting the formation of 2,3-epoxy-3-methylindoline: a reactive intermediate of the pneumotoxin 3-methylindole. *Chem Res Toxicol* 11:741–749.

Skordos K W, Laycock J D and Yost G S (1998b) Thioether adducts of a new imine reactive intermediate of the pneumotoxin 3-methylindole. *Chem Res Toxicol* 11: 1326–1231.

Smith P K, Krohn R I, Hermanson G T, Mallia A K, Gartner F H, Provenzano M D, Fujimoto E K, Goeke N M, Olson B J and Klenk D C (1985) Measurement of protein using bicinchoninic acid. *Anal Biochem* 150:76–85.

Smith D J, Skiles G L, Appleton M L, Carlson J R and Yost G S (1993) Identification of goat and mouse urinary metabolites of the pneumotoxin, 3 methylindole. *Xenobiotica* 23:1025–1044.

Squires E J and Lundström K (1997) Relationship between cytochrome P450IIE1 in liver and levels of skatole and its metabolites in intact male pigs. *J Anim Sci* 75:2506–2511.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

What is claimed is:

1. A method of genetically typing pigs to determine those with boar taint characteristics, comprising:
   obtaining a sample of genetic material from said pig; and
   assaying for the presence of a genotype in said pig which is associated with boar taint, said genotype characterized by the following:
   a) a polymorphism in the CYP2A6 gene as set forth in SEQ ID NO:3, wherein said polymorphism is a t/c polymorphism at nucleotide position 124 of SEQ ID NO:3 or a deletion of guanine at nucleotide position 422 of SEQ ID NO:3, said polymorphisms being associated with boar taint characteristics.

2. The method of claim 1 wherein said polymorphism of a deletion of guanine at nucleotide position 422 of SEQ ID NO:3 results in a loss of function mutation of CYP2A6.

3. The method of claim 1 wherein said t/c polymorphism at nucleotide position 124 of SEQ ID NO:3 results in a Phe to Leu change at position 42 of SEQ ID NQ:4.

4. The method of claim 1 wherein said polymorphism of a deletion of guanine at nucleotide position 422 of SEQ ID NO:3 results in a truncated CYP2A6 protein of SEQ ID NO:8.

5. The method of claim 1 wherein said step of assaying is selected from the group consisting of: restriction fragment length polymorphism (RFLP) analysis, minisequencing, MALD-TOF, SINE, beteroduplex analysis, one base extension methods, single strand conformational polymorphism (SSCP), denaturing gradient gel electrophoresis (DGGE) and temperature gradient gel electrophoresis (TGGE).

6. A method of genetically typing pigs according to skatole metabolism comprising:
   obtaining a sample of genetic material from said pig;
   assaying for the presence of an allele characterized by a polymorphism in a CYP2AG gene as set forth in SEQ ID NO:3 present in said sample, wherein said polymorphism results in a deletion of guanine at position 422 of SEQ ID NO:3, or a c/t transition at position 124 of SEQ ID NO:3; and
   correlating said allele with skatole metabolism, and concomitant boar taint.

7. The method of claim 6 wherein said step of assaying is selected from the group consisting of: restriction fragment length polymorphism (RFLP) analysis, minisequencing, MALD-TOF, SINE, heteroduplex analysis, one base extension methods, single strand eanformational polymorphism (SSCP), denaturing gradient gel electrophoresis (DGGE) and temperature gradient gel electrophoresis (TGGE).

* * * * *

UNITED STATES PATENT AND TRADEMARK OFFICE
CERTIFICATE OF CORRECTION

PATENT NO. : 7,202,035 B2
APPLICATION NO. : 10/434966
DATED : April 10, 2007
INVENTOR(S) : E. James Squires et al.

It is certified that error appears in the above-identified patent and that said Letters Patent is hereby corrected as shown below:

Claim 5
Column 70, Line 2:
DELETE: after "SINE", "beteroduplex"
ADD: after "SINE", --heteroduplex--

Claim 6
Column 70, Line 10:
DELETE: after "in a", "CYP2AG"
ADD: after "in a", --CYP2A6--

Claim 7
Column 70, Line 21:
DELETE: after "strand", "eanformational"
ADD: after "strand", --conformational--

Signed and Sealed this

Eighth Day of May, 2007

JON W. DUDAS
*Director of the United States Patent and Trademark Office*

SEQUENCE LISTING

<160> NUMBER OF SEQ ID NOS: 19

<210> SEQ ID NO 1
<211> LENGTH: 1484
<212> TYPE: DNA
<213> ORGANISM: Sus scrofa
<220> FEATURE:
<221> NAME/KEY: CDS
<222> LOCATION: (1)..(612)
<223> OTHER INFORMATION:

<400> SEQUENCE: 1

```
atg ctg gcc tca ggc ttg ctt ctc gtg gct ctg ctg acc tgc ctg acc      48
Met Leu Ala Ser Gly Leu Leu Leu Val Ala Leu Leu Thr Cys Leu Thr
1               5                   10                  15 ata atg gtc ttg atg tcc gtc tgg cgc cag agg aag ctc cag ggg aaa      96
Ile Met Val Leu Met Ser Val Trp Arg Gln Arg Lys Leu Gln Gly Lys
            20                  25                  30 ctg ccc ccc gga ccc acc ccg ctg ccc ctc atc ggg aac tac ctg cag     144
Leu Pro Pro Gly Pro Thr Pro Leu Pro Leu Ile Gly Asn Tyr Leu Gln
        35                  40                  45 ctg aac acg gag cag atg tac aac tcc ctc atg aag atc agc cag cgc     192
Leu Asn Thr Glu Gln Met Tyr Asn Ser Leu Met Lys Ile Ser Gln Arg
    50                  55                  60 tat ggc cct gtg ttc acc gtc cac ctg ggg ccc cgg cgg ata gtg gtg     240
Tyr Gly Pro Val Phe Thr Val His Leu Gly Pro Arg Arg Ile Val Val
65                  70                  75                  80 ctg tgt gga tac gac gcg gtg aag gag gcc ctg gtg gac cag gct gag     288
Leu Cys Gly Tyr Asp Ala Val Lys Glu Ala Leu Val Asp Gln Ala Glu
                85                  90                  95 gaa ttc agc ggg cga ggc gag cag gcc act ttc gac tgg ctc ttc aaa     336
Glu Phe Ser Gly Arg Gly Glu Gln Ala Thr Phe Asp Trp Leu Phe Lys
            100                 105                 110 ggc tat ggc gtg gcc ttc agc aac ggc gag cgt gcc aag cag ctc cgg     384
Gly Tyr Gly Val Ala Phe Ser Asn Gly Glu Arg Ala Lys Gln Leu Arg
        115                 120                 125 cgc ttc tcc atc acc acg ctg cgg gac ttc ggc gtg gca agc ggg gta     432
Arg Phe Ser Ile Thr Thr Leu Arg Asp Phe Gly Val Ala Ser Gly Val
    130                 135                 140 tcg agg agc gca tcc agg agg agg cgg gcc acc tca tcg agg cct tcc     480
Ser Arg Ser Ala Ser Arg Arg Arg Arg Ala Thr Ser Ser Arg Pro Ser
145                 150                 155                 160 ggg gca cgc gcg gcg cgt tca tcg acc cca cct act tcc tca gcc gaa     528
Gly Ala Arg Ala Ala Arg Ser Ser Thr Pro Pro Thr Ser Ser Ala Glu
                165                 170                 175 cgg ttt cca atg tca tca gct cca ttg tct tcg gag acc gct ttg act     576
Arg Phe Pro Met Ser Ser Ala Pro Leu Ser Ser Glu Thr Ala Leu Thr
            180                 185                 190 atg agg aca aag agt tcc tcg cac tgc tgc gga tga tgctgggaag          622
```

```
Met Arg Thr Lys Ser Ser His Cys Cys Gly
        195                 200 ctttcagttc acagctacct ctaccggaca gctctatgag atgttctact cggtgatgaa     682
acacctgcca gggccgcagc aacaggcatt taaggacctg caggggctgg aggacttcat     742
agccaggaag gtggaacaca accagcgcac gctggatccc aactcccgc gagacttcat      802 cgactccttc ctcatccgca tgcaggagga agaagaaat cctgacaccg agttctattg      862
gaagaacctg gttctgacca cactgaacct cttcttcgcg ggcaccgaga cggtcagcac      922
aacgatgcgc tacggcttcc tgctgctcat gaagcacccg gatgtggagg ccaaagtcca     982
cgaggagatt gaccgcgtga tcggcaggaa ccgccaggcc aagttcgagg accgggccaa    1042
gatgccctac acggaggccg tgatccacga gatccagaga ttcggagaca tgatccccat     1102
gggcctggcc cgaagagtca ccaaggatac caagtttcgg gacttcctcc tccccaaggg    1162
cactgaggtg ttccctatgc tgggctctgt gctgagagac cccaagttct ctccaaccc     1222 ccgaggcttc aaccccagc acttcctgga tgagaacggg cagtttaaga agaatgatgc      1282
ttttgtgccc ttctccatcg gaaagcggta ctgtttcgga gaaggtctgg ctagaatgga    1342
gctcttcctc ttcctcacca acatcctgca gaacttccac ctcaagtctc cgcagctgcc    1402
ccaggacatc gacgtgtccc ccaaacacgt gggcttcgcc accatccccc cgacctacac    1462
catgagcttc ctgccccgct ga                                              1484
```

<210> SEQ ID NO 2
<211> LENGTH: 203
<212> TYPE: PRT
<213> ORGANISM: Sus scrofa

<400> SEQUENCE: 2

```
Met Leu Ala Ser Gly Leu Leu Val Ala Leu Leu Thr Cys Leu Thr
1               5                   10                  15

Ile Met Val Leu Met Ser Val Trp Arg Gln Arg Lys Leu Gln Gly Lys
            20                  25                  30

Leu Pro Pro Gly Pro Thr Pro Leu Pro Leu Ile Gly Asn Tyr Leu Gln
        35                  40                  45

Leu Asn Thr Glu Gln Met Tyr Asn Ser Leu Met Lys Ile Ser Gln Arg
    50                  55                  60

Tyr Gly Pro Val Phe Thr Val His Leu Gly Pro Arg Arg Ile Val Val
65                  70                  75                  80

Leu Cys Gly Tyr Asp Ala Val Lys Glu Ala Leu Val Asp Gln Ala Glu
                85                  90                  95

Glu Phe Ser Gly Arg Gly Glu Gln Ala Thr Phe Asp Trp Leu Phe Lys
            100                 105                 110

Gly Tyr Gly Val Ala Phe Ser Asn Gly Glu Arg Ala Lys Gln Leu Arg
        115                 120                 125

Arg Phe Ser Ile Thr Thr Leu Arg Asp Phe Gly Val Ala Ser Gly Val
    130                 135                 140

Ser Arg Ser Ala Ser Arg Arg Arg Ala Thr Ser Ser Arg Pro Ser
145                 150                 155                 160

Gly Ala Arg Ala Ala Arg Ser Ser Thr Pro Pro Thr Ser Ser Ala Glu
                165                 170                 175

Arg Phe Pro Met Ser Ser Ala Pro Leu Ser Ser Glu Thr Ala Leu Thr
            180                 185                 190

Met Arg Thr Lys Ser Ser His Cys Cys Gly
        195                 200
```

<210> SEQ ID NO 3
<211> LENGTH: 1485
<212> TYPE: DNA
<213> ORGANISM: Sus scrofa
<220> FEATURE:
<221> NAME/KEY: CDS
<222> LOCATION: (1)..(1485)
<223> OTHER INFORMATION:

<400> SEQUENCE: 3

| | | | | | | | | | | | | | | | | |
|---|---|---|---|---|---|---|---|---|---|---|---|---|---|---|---|---|
| atg | ctg | gcc | tca | ggc | ttg | ctt | ctc | gtg | gct | ctg | ctg | acc | tgc | ctg | acc | 48 |
| Met | Leu | Ala | Ser | Gly | Leu | Leu | Leu | Val | Ala | Leu | Leu | Thr | Cys | Leu | Thr | |
| 1 | | | | 5 | | | | | 10 | | | | | 15 | | |
| ata | atg | gtc | ttg | atg | tcc | gtc | tgg | cgc | cag | agg | aag | ctc | cag | ggg | aaa | 96 |
| Ile | Met | Val | Leu | Met | Ser | Val | Trp | Arg | Gln | Arg | Lys | Leu | Gln | Gly | Lys | |
| | | | 20 | | | | | 25 | | | | | 30 | | | |
| ctg | ccc | ccc | gga | ccc | acc | ccg | ctg | ccc | ttc | atc | ggg | aac | tac | ctg | cag | 144 |
| Leu | Pro | Pro | Gly | Pro | Thr | Pro | Leu | Pro | Phe | Ile | Gly | Asn | Tyr | Leu | Gln | |
| | | | | 35 | | | | | 40 | | | | | 45 | | |
| ctg | aac | acg | gag | cag | atg | tac | aac | tcc | ctc | atg | aag | atc | agc | cag | cgc | 192 |
| Leu | Asn | Thr | Glu | Gln | Met | Tyr | Asn | Ser | Leu | Met | Lys | Ile | Ser | Gln | Arg | |
| | 50 | | | | | 55 | | | | | 60 | | | | | |
| tat | ggc | cct | gtg | ttc | acc | gtc | cac | ctg | ggg | ccc | cgg | cgg | ata | gtg | gtg | 240 |
| Tyr | Gly | Pro | Val | Phe | Thr | Val | His | Leu | Gly | Pro | Arg | Arg | Ile | Val | Val | |
| 65 | | | | | 70 | | | | | 75 | | | | | 80 | |
| ctg | tgt | gga | tac | gac | gcg | gtg | aag | gag | gcc | ctg | gtg | gac | cag | gct | gag | 288 |
| Leu | Cys | Gly | Tyr | Asp | Ala | Val | Lys | Glu | Ala | Leu | Val | Asp | Gln | Ala | Glu | |
| | | | | 85 | | | | | 90 | | | | | 95 | | |
| gaa | ttc | agc | ggg | cga | ggc | gag | cag | gcc | act | ttc | gac | tgg | ctc | ttc | aaa | 336 |
| Glu | Phe | Ser | Gly | Arg | Gly | Glu | Gln | Ala | Thr | Phe | Asp | Trp | Leu | Phe | Lys | |
| | | | | 100 | | | | | 105 | | | | | 110 | | |
| ggc | tat | ggc | gtg | gcc | ttc | agc | aac | ggc | gag | cgt | gcc | aag | cag | ctc | cgg | 384 |
| Gly | Tyr | Gly | Val | Ala | Phe | Ser | Asn | Gly | Glu | Arg | Ala | Lys | Gln | Leu | Arg | |
| | | | 115 | | | | | 120 | | | | | 125 | | | |
| cgc | ttc | tcc | atc | acc | acg | ctg | cgg | gac | ttc | ggc | gtg | ggc | aag | cgg | ggt | 432 |
| Arg | Phe | Ser | Ile | Thr | Thr | Leu | Arg | Asp | Phe | Gly | Val | Gly | Lys | Arg | Gly | |
| | 130 | | | | | 135 | | | | | 140 | | | | | |
| atc | gag | gag | cgc | atc | cag | gag | gag | gcg | ggc | cac | ctc | atc | gag | gcc | ttc | 480 |
| Ile | Glu | Glu | Arg | Ile | Gln | Glu | Glu | Ala | Gly | His | Leu | Ile | Glu | Ala | Phe | |
| 145 | | | | | 150 | | | | | 155 | | | | | 160 | |
| cgg | ggc | acg | cgc | ggc | gcg | ttc | atc | gac | ccc | acc | tac | ttc | ctc | agc | cga | 528 |
| Arg | Gly | Thr | Arg | Gly | Ala | Phe | Ile | Asp | Pro | Thr | Tyr | Phe | Leu | Ser | Arg | |
| | | | | 165 | | | | | 170 | | | | | 175 | | |
| acg | gtt | tcc | aat | gtc | atc | agc | tcc | att | gtc | ttc | gga | gac | cgc | ttt | gac | 576 |
| Thr | Val | Ser | Asn | Val | Ile | Ser | Ser | Ile | Val | Phe | Gly | Asp | Arg | Phe | Asp | |
| | | | | 180 | | | | | 185 | | | | | 190 | | |
| tat | gag | gac | aaa | gag | ttc | ctc | gca | ctg | ctg | cgg | atg | atg | ctg | gga | agc | 624 |
| Tyr | Glu | Asp | Lys | Glu | Phe | Leu | Ala | Leu | Leu | Arg | Met | Met | Leu | Gly | Ser | |
| | | | 195 | | | | | 200 | | | | | 205 | | | |
| ttt | cag | ttc | aca | gct | acc | tct | acc | gga | cag | ctc | tat | gag | atg | ttc | tac | 672 |
| Phe | Gln | Phe | Thr | Ala | Thr | Ser | Thr | Gly | Gln | Leu | Tyr | Glu | Met | Phe | Tyr | |
| | 210 | | | | | 215 | | | | | 220 | | | | | |
| tcg | gtg | atg | aaa | cac | ctg | cca | ggg | ccg | cag | caa | cag | gca | ttt | aag | gac | 720 |
| Ser | Val | Met | Lys | His | Leu | Pro | Gly | Pro | Gln | Gln | Gln | Ala | Phe | Lys | Asp | |
| 225 | | | | | 230 | | | | | 235 | | | | | 240 | |
| ctg | cag | ggg | ctg | gag | gac | ttc | ata | gcc | agg | aag | gtg | gaa | cac | aac | cag | 768 |
| Leu | Gln | Gly | Leu | Glu | Asp | Phe | Ile | Ala | Arg | Lys | Val | Glu | His | Asn | Gln | |
| | | | | 245 | | | | | 250 | | | | | 255 | | |
| cgc | acg | ctg | gat | ccc | aac | tcc | ccg | cga | gac | ttc | atc | gac | tcc | ttc | ctc | 816 |
| Arg | Thr | Leu | Asp | Pro | Asn | Ser | Pro | Arg | Asp | Phe | Ile | Asp | Ser | Phe | Leu | |

```
                   260                 265                 270
atc cgc atg cag gag gag aag aag aat cct gac acc gag ttc tat tgg     864
Ile Arg Met Gln Glu Glu Lys Lys Asn Pro Asp Thr Glu Phe Tyr Trp
        275                 280                 285 aag aac ctg gtt ctg acc aca ctg aac ctc ttc ttc gcg ggc acc gag     912
Lys Asn Leu Val Leu Thr Thr Leu Asn Leu Phe Phe Ala Gly Thr Glu
    290                 295                 300 acg gtc agc aca acg atg cgc tac ggc ttc ctg ctc ctc atg aag cac     960
Thr Val Ser Thr Thr Met Arg Tyr Gly Phe Leu Leu Leu Met Lys His
305                 310                 315                 320 ccg gat gtg gag gcc aaa gtc cac gag gag att gac cgc gtg atc ggc    1008
Pro Asp Val Glu Ala Lys Val His Glu Glu Ile Asp Arg Val Ile Gly
                325                 330                 335 agg aac cgc cag gcc aag ttc gag gac cgg gcc aag atg ccc tac acg    1056
Arg Asn Arg Gln Ala Lys Phe Glu Asp Arg Ala Lys Met Pro Tyr Thr
            340                 345                 350 gag gcc gtg atc cac gag atc cag aga ttc gga gac atg atc ccc atg    1104
Glu Ala Val Ile His Glu Ile Gln Arg Phe Gly Asp Met Ile Pro Met
        355                 360                 365 ggc ctg gcc cga aga gtc acc aag gat acc aag ttt cgg gac ttc ctc    1152
Gly Leu Ala Arg Arg Val Thr Lys Asp Thr Lys Phe Arg Asp Phe Leu
    370                 375                 380 ctc ccc aag ggc act gag gtg ttc cct atg ctg ggc tct gtg ctg aga    1200
Leu Pro Lys Gly Thr Glu Val Phe Pro Met Leu Gly Ser Val Leu Arg
385                 390                 395                 400 gac ccc aag ttc ttc tcc aac ccc cga ggc ttc aac ccc cag cac ttc    1248
Asp Pro Lys Phe Phe Ser Asn Pro Arg Gly Phe Asn Pro Gln His Phe
                405                 410                 415 ctg gat gag aac ggg cag ttt aag aag aat gat gct ttt gtg ccc ttc    1296
Leu Asp Glu Asn Gly Gln Phe Lys Lys Asn Asp Ala Phe Val Pro Phe
            420                 425                 430 tcc atc gga aag cgg tac tgt ttc gga gaa ggt ctg gct aga atg gag    1344
Ser Ile Gly Lys Arg Tyr Cys Phe Gly Glu Gly Leu Ala Arg Met Glu
        435                 440                 445 ctc ttc ctc ttc ctc acc aac atc ctg cag aac ttc cac ctc aag tct    1392
Leu Phe Leu Phe Leu Thr Asn Ile Leu Gln Asn Phe His Leu Lys Ser
    450                 455                 460 ccg cag ctg ccc cag gac atc gac gtg tcc ccc aaa cac gtg ggc ttc    1440
Pro Gln Leu Pro Gln Asp Ile Asp Val Ser Pro Lys His Val Gly Phe
465                 470                 475                 480 gcc acc atc ccc ccg acc tac acc atg agc ttc ctg ccc cgc tga        1485
Ala Thr Ile Pro Pro Thr Tyr Thr Met Ser Phe Leu Pro Arg
                485                 490

<210> SEQ ID NO 4
<211> LENGTH: 494
<212> TYPE: PRT
<213> ORGANISM: Sus scrofa

<400> SEQUENCE: 4

Met Leu Ala Ser Gly Leu Leu Leu Val Ala Leu Leu Thr Cys Leu Thr
1               5                   10                  15

Ile Met Val Leu Met Ser Val Trp Arg Gln Arg Lys Leu Gln Gly Lys
            20                  25                  30

Leu Pro Pro Gly Pro Thr Pro Leu Pro Phe Ile Gly Asn Tyr Leu Gln
        35                  40                  45

Leu Asn Thr Glu Gln Met Tyr Asn Ser Leu Met Lys Ile Ser Gln Arg
    50                  55                  60

Tyr Gly Pro Val Phe Thr Val His Leu Gly Pro Arg Arg Ile Val Val
```

```
              65                  70                  75                  80
Leu Cys Gly Tyr Asp Ala Val Lys Glu Ala Leu Val Asp Gln Ala Glu
                    85                  90                  95
Glu Phe Ser Gly Arg Gly Glu Gln Ala Thr Phe Asp Trp Leu Phe Lys
                   100                 105                 110
Gly Tyr Gly Val Ala Phe Ser Asn Gly Glu Arg Ala Lys Gln Leu Arg
                   115                 120                 125
Arg Phe Ser Ile Thr Thr Leu Arg Asp Phe Gly Val Gly Lys Arg Gly
                   130                 135                 140
Ile Glu Glu Arg Ile Gln Glu Ala Gly His Leu Ile Glu Ala Phe
145                 150                 155                 160
Arg Gly Thr Arg Gly Ala Phe Ile Asp Pro Thr Tyr Phe Leu Ser Arg
                   165                 170                 175
Thr Val Ser Asn Val Ile Ser Ser Ile Val Phe Gly Asp Arg Phe Asp
                   180                 185                 190
Tyr Glu Asp Lys Glu Phe Leu Ala Leu Leu Arg Met Met Leu Gly Ser
                   195                 200                 205
Phe Gln Phe Thr Ala Thr Ser Thr Gly Gln Leu Tyr Glu Met Phe Tyr
                   210                 215                 220
Ser Val Met Lys His Leu Pro Gly Pro Gln Gln Ala Phe Lys Asp
225                 230                 235                 240
Leu Gln Gly Leu Glu Asp Phe Ile Ala Arg Lys Val Glu His Asn Gln
                   245                 250                 255
Arg Thr Leu Asp Pro Asn Ser Pro Arg Asp Phe Ile Asp Ser Phe Leu
                   260                 265                 270
Ile Arg Met Gln Glu Glu Lys Lys Asn Pro Asp Thr Glu Phe Tyr Trp
                   275                 280                 285
Lys Asn Leu Val Leu Thr Thr Leu Asn Leu Phe Phe Ala Gly Thr Glu
                   290                 295                 300
Thr Val Ser Thr Thr Met Arg Tyr Gly Phe Leu Leu Leu Met Lys His
305                 310                 315                 320
Pro Asp Val Glu Ala Lys Val His Glu Glu Ile Asp Arg Val Ile Gly
                   325                 330                 335
Arg Asn Arg Gln Ala Lys Phe Glu Asp Arg Ala Lys Met Pro Tyr Thr
                   340                 345                 350
Glu Ala Val Ile His Glu Ile Gln Arg Phe Gly Asp Met Ile Pro Met
                   355                 360                 365
Gly Leu Ala Arg Arg Val Thr Lys Asp Thr Lys Phe Arg Asp Phe Leu
                   370                 375                 380
Leu Pro Lys Gly Thr Glu Val Phe Pro Met Leu Gly Ser Val Leu Arg
385                 390                 395                 400
Asp Pro Lys Phe Phe Ser Asn Pro Arg Gly Phe Asn Pro Gln His Phe
                   405                 410                 415
Leu Asp Glu Asn Gly Gln Phe Lys Lys Asn Asp Ala Phe Val Pro Phe
                   420                 425                 430
Ser Ile Gly Lys Arg Tyr Cys Phe Gly Glu Gly Leu Ala Arg Met Glu
                   435                 440                 445
Leu Phe Leu Phe Leu Thr Asn Ile Leu Gln Asn Phe His Leu Lys Ser
                   450                 455                 460
Pro Gln Leu Pro Gln Asp Ile Asp Val Ser Pro Lys His Val Gly Phe
465                 470                 475                 480
Ala Thr Ile Pro Pro Thr Tyr Thr Met Ser Phe Leu Pro Arg
                   485                 490
```

<210> SEQ ID NO 5
<211> LENGTH: 1485
<212> TYPE: DNA
<213> ORGANISM: Sus scrofa
<220> FEATURE:
<221> NAME/KEY: CDS
<222> LOCATION: (1)..(1485)
<223> OTHER INFORMATION:

<400> SEQUENCE: 5

| atg ctg gcc tca ggc ttg ctt ctc gtg gct ctg ctg acc tgc ctg acc | 48 |
| Met Leu Ala Ser Gly Leu Leu Leu Val Ala Leu Leu Thr Cys Leu Thr | |
| 1               5                   10                  15 | |

| ata atg gtc ttg atg tcc gtc tgg cgc cag agg aag ctc cag ggg aaa | 96 |
| Ile Met Val Leu Met Ser Val Trp Arg Gln Arg Lys Leu Gln Gly Lys | |
|         20                  25                  30 | |

| ctg ccc ccc gga ccc acc ccg ctg ccc ctc atc ggg aac tac ctg cag | 144 |
| Leu Pro Pro Gly Pro Thr Pro Leu Pro Leu Ile Gly Asn Tyr Leu Gln | |
|     35                  40                  45 | |

| ctg aac acg gag cag atg tac aac tcc ctc atg aag atc agc cag cgc | 192 |
| Leu Asn Thr Glu Gln Met Tyr Asn Ser Leu Met Lys Ile Ser Gln Arg | |
| 50                  55                  60 | |

| tat ggc cct gtg ttc acc gtc cac ctg ggg ccc cgg cgg ata gtg gtg | 240 |
| Tyr Gly Pro Val Phe Thr Val His Leu Gly Pro Arg Arg Ile Val Val | |
| 65                  70                  75                  80 | |

| ctg tgt gga tac gac gcg gtg aag gag gcc ctg gtg gac cag gct gag | 288 |
| Leu Cys Gly Tyr Asp Ala Val Lys Glu Ala Leu Val Asp Gln Ala Glu | |
|             85                  90                  95 | |

| gaa ttc agc ggg cga ggc gag cag gcc act ttc gac tgg ctc ttc aaa | 336 |
| Glu Phe Ser Gly Arg Gly Glu Gln Ala Thr Phe Asp Trp Leu Phe Lys | |
|             100                 105                 110 | |

| ggc tat ggc gtg gcc ttc agc aac ggc gag cgt gcc aag cag ctc cgg | 384 |
| Gly Tyr Gly Val Ala Phe Ser Asn Gly Glu Arg Ala Lys Gln Leu Arg | |
|         115                 120                 125 | |

| cgc ttc tcc atc acc acg ctg cgg gac ttc ggc gtg ggc aag cgg ggt | 432 |
| Arg Phe Ser Ile Thr Thr Leu Arg Asp Phe Gly Val Gly Lys Arg Gly | |
| 130                 135                 140 | |

| atc gag gag cgc atc cag gag gag gcg ggc cac ctc atc gag gcc ttc | 480 |
| Ile Glu Glu Arg Ile Gln Glu Glu Ala Gly His Leu Ile Glu Ala Phe | |
| 145                 150                 155                 160 | |

| cgg ggc acg cgc ggc gcg ttc atc gac ccc acc tac ttc ctc agc cga | 528 |
| Arg Gly Thr Arg Gly Ala Phe Ile Asp Pro Thr Tyr Phe Leu Ser Arg | |
|             165                 170                 175 | |

| acg gtt tcc aat gtc atc agc tcc att gtc ttc gga gac cgc ttt gac | 576 |
| Thr Val Ser Asn Val Ile Ser Ser Ile Val Phe Gly Asp Arg Phe Asp | |
|             180                 185                 190 | |

| tat gag gac aaa gag ttc ctc gca ctg ctg cgg atg atg ctg gga agc | 624 |
| Tyr Glu Asp Lys Glu Phe Leu Ala Leu Leu Arg Met Met Leu Gly Ser | |
|         195                 200                 205 | |

| ttt cag ttc aca gct acc tct acc gga cag ctc tat gag atg ttc tac | 672 |
| Phe Gln Phe Thr Ala Thr Ser Thr Gly Gln Leu Tyr Glu Met Phe Tyr | |
| 210                 215                 220 | |

| tcg gtg atg aaa cac ctg cca ggg ccg cag caa cag gca ttt aag gac | 720 |
| Ser Val Met Lys His Leu Pro Gly Pro Gln Gln Gln Ala Phe Lys Asp | |
| 225                 230                 235                 240 | |

| ctg cag ggg ctg gag gac ttc ata gcc agg aag gtg gaa cac aac cag | 768 |
| Leu Gln Gly Leu Glu Asp Phe Ile Ala Arg Lys Val Glu His Asn Gln | |
|             245                 250                 255 | |

| cgc acg ctg gat ccc aac tcc ccg cga gac ttc atc gac tcc ttc ctc | 816 |
| Arg Thr Leu Asp Pro Asn Ser Pro Arg Asp Phe Ile Asp Ser Phe Leu | |

-continued

```
                          260                 265                 270
atc cgc atg cag gag gag aag aag aat cct gac acc gag ttc tat tgg    864
Ile Arg Met Gln Glu Glu Lys Lys Asn Pro Asp Thr Glu Phe Tyr Trp
            275                 280                 285 aag aac ctg gtt ctg acc aca ctg aac ctc ttc ttc gcg ggc acc gag    912
Lys Asn Leu Val Leu Thr Thr Leu Asn Leu Phe Phe Ala Gly Thr Glu
        290                 295                 300 acg gtc agc aca acg atg cgc tac ggc ttc ctg ctc atg aag cac        960
Thr Val Ser Thr Thr Met Arg Tyr Gly Phe Leu Leu Leu Met Lys His
    305                 310                 315                 320 ccg gat gtg gag gcc aaa gtc cac gag gag att gac cgc gtg atc ggc   1008
Pro Asp Val Glu Ala Lys Val His Glu Glu Ile Asp Arg Val Ile Gly
                325                 330                 335 agg aac cgc cag gcc aag ttc gag gac cgg gcc aag atg ccc tac acg   1056
Arg Asn Arg Gln Ala Lys Phe Glu Asp Arg Ala Lys Met Pro Tyr Thr
            340                 345                 350 gag gcc gtg atc cac gag atc cag aga ttc gga gac atg atc ccc atg   1104
Glu Ala Val Ile His Glu Ile Gln Arg Phe Gly Asp Met Ile Pro Met
        355                 360                 365 ggc ctg gcc cga aga gtc acc aag gat acc aag ttt cgg gac ttc ctc   1152
Gly Leu Ala Arg Arg Val Thr Lys Asp Thr Lys Phe Arg Asp Phe Leu
    370                 375                 380 ctc ccc aag ggc act gag gtg ttc cct atg ctg ggc tct gtg ctg aga   1200
Leu Pro Lys Gly Thr Glu Val Phe Pro Met Leu Gly Ser Val Leu Arg
385                 390                 395                 400 gac ccc aag ttc ttc tcc aac ccc cga ggc ttc aac ccc cag cac ttc   1248
Asp Pro Lys Phe Phe Ser Asn Pro Arg Gly Phe Asn Pro Gln His Phe
                405                 410                 415 ctg gat gag aac ggg cag ttt aag aag aat gat gct ttt gtg ccc ttc   1296
Leu Asp Glu Asn Gly Gln Phe Lys Lys Asn Asp Ala Phe Val Pro Phe
            420                 425                 430 tcc atc gga aag cgg tac tgt ttc gga gaa ggt ctg gct aga atg gag   1344
Ser Ile Gly Lys Arg Tyr Cys Phe Gly Glu Gly Leu Ala Arg Met Glu
        435                 440                 445 ctc ttc ctc ttc ctc acc aac atc ctg cag aac ttc cac ctc aag tct   1392
Leu Phe Leu Phe Leu Thr Asn Ile Leu Gln Asn Phe His Leu Lys Ser
    450                 455                 460 ccg cag ctg ccc cag gac atc gac gtg tcc ccc aaa cac gtg ggc ttc   1440
Pro Gln Leu Pro Gln Asp Ile Asp Val Ser Pro Lys His Val Gly Phe
465                 470                 475                 480 gcc acc atc ccc ccg acc tac acc atg agc ttc ctg ccc cgc tga       1485
Ala Thr Ile Pro Pro Thr Tyr Thr Met Ser Phe Leu Pro Arg
                485                 490

<210> SEQ ID NO 6
<211> LENGTH: 494
<212> TYPE: PRT
<213> ORGANISM: Sus scrofa

<400> SEQUENCE: 6

Met Leu Ala Ser Gly Leu Leu Leu Val Ala Leu Leu Thr Cys Leu Thr
 1               5                  10                  15

Ile Met Val Leu Met Ser Val Trp Arg Gln Arg Lys Leu Gln Gly Lys
            20                  25                  30

Leu Pro Pro Gly Pro Thr Pro Leu Pro Leu Ile Gly Asn Tyr Leu Gln
        35                  40                  45

Leu Asn Thr Glu Gln Met Tyr Asn Ser Leu Met Lys Ile Ser Gln Arg
    50                  55                  60

Tyr Gly Pro Val Phe Thr Val His Leu Gly Pro Arg Arg Ile Val Val
```

```
            65                  70                  75                  80
Leu Cys Gly Tyr Asp Ala Val Lys Glu Ala Leu Val Asp Gln Ala Glu
                    85                  90                  95

Glu Phe Ser Gly Arg Gly Glu Gln Ala Thr Phe Asp Trp Leu Phe Lys
                100                 105                 110

Gly Tyr Gly Val Ala Phe Ser Asn Gly Glu Arg Ala Lys Gln Leu Arg
                115                 120                 125

Arg Phe Ser Ile Thr Thr Leu Arg Asp Phe Gly Val Gly Lys Arg Gly
            130                 135                 140

Ile Glu Glu Arg Ile Gln Glu Ala Gly His Leu Ile Glu Ala Phe
145                 150                 155                 160

Arg Gly Thr Arg Gly Ala Phe Ile Asp Pro Thr Tyr Phe Leu Ser Arg
                165                 170                 175

Thr Val Ser Asn Val Ile Ser Ser Ile Val Phe Gly Asp Arg Phe Asp
                180                 185                 190

Tyr Glu Asp Lys Glu Phe Leu Ala Leu Leu Arg Met Met Leu Gly Ser
            195                 200                 205

Phe Gln Phe Thr Ala Thr Ser Thr Gly Gln Leu Tyr Glu Met Phe Tyr
            210                 215                 220

Ser Val Met Lys His Leu Pro Gly Pro Gln Gln Ala Phe Lys Asp
225                 230                 235                 240

Leu Gln Gly Leu Glu Asp Phe Ile Ala Arg Lys Val Glu His Asn Gln
                245                 250                 255

Arg Thr Leu Asp Pro Asn Ser Pro Arg Asp Phe Ile Asp Ser Phe Leu
            260                 265                 270

Ile Arg Met Gln Glu Glu Lys Lys Asn Pro Asp Thr Glu Phe Tyr Trp
            275                 280                 285

Lys Asn Leu Val Leu Thr Thr Leu Asn Leu Phe Phe Ala Gly Thr Glu
290                 295                 300

Thr Val Ser Thr Thr Met Arg Tyr Gly Phe Leu Leu Leu Met Lys His
305                 310                 315                 320

Pro Asp Val Glu Ala Lys Val His Glu Glu Ile Asp Arg Val Ile Gly
                325                 330                 335

Arg Asn Arg Gln Ala Lys Phe Glu Asp Arg Ala Lys Met Pro Tyr Thr
            340                 345                 350

Glu Ala Val Ile His Glu Ile Gln Arg Phe Gly Asp Met Ile Pro Met
            355                 360                 365

Gly Leu Ala Arg Arg Val Thr Lys Asp Thr Lys Phe Arg Asp Phe Leu
            370                 375                 380

Leu Pro Lys Gly Thr Glu Val Phe Pro Met Leu Gly Ser Val Leu Arg
385                 390                 395                 400

Asp Pro Lys Phe Phe Ser Asn Pro Arg Gly Phe Asn Pro Gln His Phe
                405                 410                 415

Leu Asp Glu Asn Gly Gln Phe Lys Lys Asn Asp Ala Phe Val Pro Phe
            420                 425                 430

Ser Ile Gly Lys Arg Tyr Cys Phe Gly Glu Gly Leu Ala Arg Met Glu
            435                 440                 445

Leu Phe Leu Phe Leu Thr Asn Ile Leu Gln Asn Phe His Leu Lys Ser
            450                 455                 460

Pro Gln Leu Pro Gln Asp Ile Asp Val Ser Pro Lys His Val Gly Phe
465                 470                 475                 480

Ala Thr Ile Pro Pro Thr Tyr Thr Met Ser Phe Leu Pro Arg
            485                 490
```

<210> SEQ ID NO 7
<211> LENGTH: 1484
<212> TYPE: DNA
<213> ORGANISM: Sus scrofa
<220> FEATURE:
<221> NAME/KEY: CDS
<222> LOCATION: (1)..(612)
<223> OTHER INFORMATION:

<400> SEQUENCE: 7

| | | | | | | | | | | | | | | | | |
|---|---|---|---|---|---|---|---|---|---|---|---|---|---|---|---|---|
| atg | ctg | gcc | tca | ggc | ttg | ctt | ctc | gtg | gct | ctg | ctg | acc | tgc | ctg | acc | 48 |
| Met | Leu | Ala | Ser | Gly | Leu | Leu | Leu | Val | Ala | Leu | Leu | Thr | Cys | Leu | Thr | |
| 1 | | | | 5 | | | | | 10 | | | | | 15 | | |

| ata | atg | gtc | ttg | atg | tcc | gtc | tgg | cgc | cag | agg | aag | ctc | cag | ggg | aaa | 96 |
|---|---|---|---|---|---|---|---|---|---|---|---|---|---|---|---|---|
| Ile | Met | Val | Leu | Met | Ser | Val | Trp | Arg | Gln | Arg | Lys | Leu | Gln | Gly | Lys | |
| | | | 20 | | | | | 25 | | | | | 30 | | | |

| ctg | ccc | ccc | gga | ccc | acc | ccg | ctg | ccc | ttc | atc | ggg | aac | tac | ctg | cag | 144 |
|---|---|---|---|---|---|---|---|---|---|---|---|---|---|---|---|---|
| Leu | Pro | Pro | Gly | Pro | Thr | Pro | Leu | Pro | Phe | Ile | Gly | Asn | Tyr | Leu | Gln | |
| | | 35 | | | | | 40 | | | | | 45 | | | | |

| ctg | aac | acg | gag | cag | atg | tac | aac | tcc | ctc | atg | aag | atc | agc | cag | cgc | 192 |
|---|---|---|---|---|---|---|---|---|---|---|---|---|---|---|---|---|
| Leu | Asn | Thr | Glu | Gln | Met | Tyr | Asn | Ser | Leu | Met | Lys | Ile | Ser | Gln | Arg | |
| 50 | | | | | 55 | | | | | 60 | | | | | | |

| tat | ggc | cct | gtg | ttc | acc | gtc | cac | ctg | ggg | ccc | cgg | cgg | ata | gtg | gtg | 240 |
|---|---|---|---|---|---|---|---|---|---|---|---|---|---|---|---|---|
| Tyr | Gly | Pro | Val | Phe | Thr | Val | His | Leu | Gly | Pro | Arg | Arg | Ile | Val | Val | |
| 65 | | | | 70 | | | | | 75 | | | | | 80 | | |

| ctg | tgt | gga | tac | gac | gcg | gtg | aag | gag | gcc | ctg | gtg | gac | cag | gct | gag | 288 |
|---|---|---|---|---|---|---|---|---|---|---|---|---|---|---|---|---|
| Leu | Cys | Gly | Tyr | Asp | Ala | Val | Lys | Glu | Ala | Leu | Val | Asp | Gln | Ala | Glu | |
| | | | | 85 | | | | | 90 | | | | | 95 | | |

| gaa | ttc | agc | ggg | cga | ggc | gag | cag | gcc | act | ttc | gac | tgg | ctc | ttc | aaa | 336 |
|---|---|---|---|---|---|---|---|---|---|---|---|---|---|---|---|---|
| Glu | Phe | Ser | Gly | Arg | Gly | Glu | Gln | Ala | Thr | Phe | Asp | Trp | Leu | Phe | Lys | |
| | | | 100 | | | | | 105 | | | | | 110 | | | |

| ggc | tat | ggc | gtg | gcc | ttc | agc | aac | ggc | gag | cgt | gcc | aag | cag | ctc | cgg | 384 |
|---|---|---|---|---|---|---|---|---|---|---|---|---|---|---|---|---|
| Gly | Tyr | Gly | Val | Ala | Phe | Ser | Asn | Gly | Glu | Arg | Ala | Lys | Gln | Leu | Arg | |
| | | 115 | | | | | 120 | | | | | 125 | | | | |

| cgc | ttc | tcc | atc | acc | acg | ctg | cgg | gac | ttc | ggc | gtg | gca | agc | ggg | gta | 432 |
|---|---|---|---|---|---|---|---|---|---|---|---|---|---|---|---|---|
| Arg | Phe | Ser | Ile | Thr | Thr | Leu | Arg | Asp | Phe | Gly | Val | Ala | Ser | Gly | Val | |
| | 130 | | | | | 135 | | | | | 140 | | | | | |

| tcg | agg | agc | gca | tcc | agg | agg | agg | cgg | gcc | acc | tca | tcg | agg | cct | tcc | 480 |
|---|---|---|---|---|---|---|---|---|---|---|---|---|---|---|---|---|
| Ser | Arg | Ser | Ala | Ser | Arg | Arg | Arg | Arg | Ala | Thr | Ser | Ser | Arg | Pro | Ser | |
| 145 | | | | | 150 | | | | | 155 | | | | | 160 | |

| ggg | gca | cgc | gcg | gcg | cgt | tca | tcg | acc | cca | cct | act | tcc | tca | gcc | gaa | 528 |
|---|---|---|---|---|---|---|---|---|---|---|---|---|---|---|---|---|
| Gly | Ala | Arg | Ala | Ala | Arg | Ser | Ser | Thr | Pro | Pro | Thr | Ser | Ser | Ala | Glu | |
| | | | | 165 | | | | | 170 | | | | | 175 | | |

| cgg | ttt | cca | atg | tca | tca | gct | cca | ttg | tct | tcg | gag | acc | gct | ttg | act | 576 |
|---|---|---|---|---|---|---|---|---|---|---|---|---|---|---|---|---|
| Arg | Phe | Pro | Met | Ser | Ser | Ala | Pro | Leu | Ser | Ser | Glu | Thr | Ala | Leu | Thr | |
| | | | 180 | | | | | 185 | | | | | 190 | | | |

| atg | agg | aca | aag | agt | tcc | tcg | cac | tgc | tgc | gga | tga | tgctgggaag | | | | 622 |
|---|---|---|---|---|---|---|---|---|---|---|---|---|---|---|---|---|
| Met | Arg | Thr | Lys | Ser | Ser | Ser | His | Cys | Cys | Gly | | | | | | |
| | | 195 | | | | | 200 | | | | | | | | | | ctttcagttc acagctacct ctaccggaca gctctatgag atgttctact cggtgatgaa  682 acacctgcca gggccgcagc aacaggcatt taaggacctg caggggctgg aggacttcat  742 agccaggaag gtggaacaca accagcgcac gctggatccc aactcccgc gagacttcat  802 cgactccttc ctcatccgca tgcaggagga agaagaaat cctgacaccg agttctattg  862 gaagaacctg gttctgacca cactgaacct cttcttcgcg ggcaccgaga cggtcagcac  922 aacgatgcgc tacggcttcc tgctgctcat gaagcacccg gatgtggagg ccaaagtcca  982 cgaggagatt gaccgcgtga tcggcaggaa ccgccaggcc aagttcgagg accgggccaa  1042

-continued

```
gatgccctac acggaggccg tgatccacga gatccagaga ttcggagaca tgatccccat    1102
gggcctggcc cgaagagtca ccaaggatac caagtttcgg gacttcctcc tccccaaggg    1162
cactgaggtg ttccctatgc tgggctctgt gctgagagac cccaagttct tctccaaccc    1222
ccgaggcttc aacccccagc acttcctgga tgagaacggg cagtttaaga agaatgatgc    1282
ttttgtgccc ttctccatcg gaaagcggta ctgtttcgga gaaggtctgg ctagaatgga    1342
gctcttcctc ttcctcacca acatcctgca gaacttccac ctcaagtctc cgcagctgcc    1402
ccaggacatc gacgtgtccc ccaaacacgt gggcttcgcc accatccccc cgacctacac    1462
catgagcttc ctgccccgct ga                                             1484
```

<210> SEQ ID NO 8
<211> LENGTH: 203
<212> TYPE: PRT
<213> ORGANISM: Sus scrofa

<400> SEQUENCE: 8

```
Met Leu Ala Ser Gly Leu Leu Val Ala Leu Leu Thr Cys Leu Thr
1               5                   10                  15

Ile Met Val Leu Met Ser Val Trp Arg Gln Arg Lys Leu Gln Gly Lys
            20                  25                  30

Leu Pro Pro Gly Pro Thr Pro Leu Pro Phe Ile Gly Asn Tyr Leu Gln
        35                  40                  45

Leu Asn Thr Glu Gln Met Tyr Asn Ser Leu Met Lys Ile Ser Gln Arg
    50                  55                  60

Tyr Gly Pro Val Phe Thr Val His Leu Gly Pro Arg Arg Ile Val Val
65                  70                  75                  80

Leu Cys Gly Tyr Asp Ala Val Lys Glu Ala Leu Val Asp Gln Ala Glu
                85                  90                  95

Glu Phe Ser Gly Arg Gly Glu Gln Ala Thr Phe Asp Trp Leu Phe Lys
            100                 105                 110

Gly Tyr Gly Val Ala Phe Ser Asn Gly Glu Arg Ala Lys Gln Leu Arg
        115                 120                 125

Arg Phe Ser Ile Thr Thr Leu Arg Asp Phe Gly Val Ala Ser Gly Val
    130                 135                 140

Ser Arg Ser Ala Ser Arg Arg Arg Ala Thr Ser Ser Arg Pro Ser
145                 150                 155                 160

Gly Ala Arg Ala Ala Arg Ser Ser Thr Pro Pro Thr Ser Ser Ala Glu
                165                 170                 175

Arg Phe Pro Met Ser Ser Ala Pro Leu Ser Ser Glu Thr Ala Leu Thr
            180                 185                 190

Met Arg Thr Lys Ser Ser Ser His Cys Cys Gly
        195                 200
```

<210> SEQ ID NO 9
<211> LENGTH: 30
<212> TYPE: DNA
<213> ORGANISM: Sus scrofa

<400> SEQUENCE: 9

```
aagcagtggt atcaacgcag agtacgcggg                                       30
```

<210> SEQ ID NO 10
<211> LENGTH: 21
<212> TYPE: DNA
<213> ORGANISM: Sus scrofa

```
<400> SEQUENCE: 10
aggacaaaga gttcctgtca c                                              21

<210> SEQ ID NO 11
<211> LENGTH: 21
<212> TYPE: DNA
<213> ORGANISM: Sus scrofa

<400> SEQUENCE: 11
caatctcctc atggaccttg g                                              21

<210> SEQ ID NO 12
<211> LENGTH: 21
<212> TYPE: DNA
<213> ORGANISM: Sus scrofa

<400> SEQUENCE: 12
atgagcagca ggaagccgta g                                              21

<210> SEQ ID NO 13
<211> LENGTH: 21
<212> TYPE: DNA
<213> ORGANISM: Sus scrofa

<400> SEQUENCE: 13
ctacggcttc ctgctgctca t                                              21

<210> SEQ ID NO 14
<211> LENGTH: 20
<212> TYPE: DNA
<213> ORGANISM: Sus scrofa

<400> SEQUENCE: 14
cacaacgatg cgctacggct                                                20

<210> SEQ ID NO 15
<211> LENGTH: 20
<212> TYPE: DNA
<213> ORGANISM: Sus scrofa

<400> SEQUENCE: 15
gcaggaagct catggtgtag                                                20

<210> SEQ ID NO 16
<211> LENGTH: 20
<212> TYPE: DNA
<213> ORGANISM: Sus scrofa

<400> SEQUENCE: 16
ctcgcagtgc caccatgctg                                                20

<210> SEQ ID NO 17
<211> LENGTH: 23
<212> TYPE: DNA
<213> ORGANISM: Sus scrofa

<400> SEQUENCE: 17
gcaggaagct catggtgtag gtc                                            23

<210> SEQ ID NO 18
<211> LENGTH: 1519
<212> TYPE: DNA
<213> ORGANISM: Sus scrofa
```

<220> FEATURE:
<221> NAME/KEY: CDS
<222> LOCATION: (35)..(1519)
<223> OTHER INFORMATION:

<400> SEQUENCE: 18

```
acgcggggaa ctgaccgtcc ctcgcagtgc cacc atg ctg gcc tca ggc ttg ctt      55
                                    Met Leu Ala Ser Gly Leu Leu
                                    1               5 ctc gtg gct ctg ctg acc tgc ctg acc ata atg gtc ttg atg tcc gtc      103
Leu Val Ala Leu Leu Thr Cys Leu Thr Ile Met Val Leu Met Ser Val
            10                  15                  20 tgg cgc cag agg aag ctc cag ggg aaa ctg ccc ccc gga ccc acc ccg      151
Trp Arg Gln Arg Lys Leu Gln Gly Lys Leu Pro Pro Gly Pro Thr Pro
25                  30                  35 ctg ccc ttc atc ggg aac tac ctg cag ctg aac acg gag cag atg tac      199
Leu Pro Phe Ile Gly Asn Tyr Leu Gln Leu Asn Thr Glu Gln Met Tyr
40                  45                  50                  55 aac tcc ctc atg aag atc agc cag cgc tat ggc cct gtg ttc acc gtc      247
Asn Ser Leu Met Lys Ile Ser Gln Arg Tyr Gly Pro Val Phe Thr Val
                60                  65                  70 cac ctg ggg ccc cgg cgg ata gtg gtg ctg tgt gga tac gac gcg gtg      295
His Leu Gly Pro Arg Arg Ile Val Val Leu Cys Gly Tyr Asp Ala Val
            75                  80                  85 aag gag gcc ctg gtg gac cag gct gag gaa ttc agc ggg cga ggc gag      343
Lys Glu Ala Leu Val Asp Gln Ala Glu Glu Phe Ser Gly Arg Gly Glu
        90                  95                  100 cag gcc act ttc gac tgg ctc ttc aaa ggc tat ggc gtg gcc ttc agc      391
Gln Ala Thr Phe Asp Trp Leu Phe Lys Gly Tyr Gly Val Ala Phe Ser
105                 110                 115 aac ggc gag cgt gcc aag cag ctc cgg cgc ttc tcc atc acc acg ctg      439
Asn Gly Glu Arg Ala Lys Gln Leu Arg Arg Phe Ser Ile Thr Thr Leu
120                 125                 130                 135 cgg gac ttc ggc gtg ggc aag cgg ggt atc gag gag cgc atc cag gag      487
Arg Asp Phe Gly Val Gly Lys Arg Gly Ile Glu Glu Arg Ile Gln Glu
                140                 145                 150 gag gcg ggc cac ctc atc gag gcc ttc cgg ggc acg cgc ggc gcg ttc      535
Glu Ala Gly His Leu Ile Glu Ala Phe Arg Gly Thr Arg Gly Ala Phe
            155                 160                 165 atc gac ccc acc tac ttc ctc agc cga acg gtt tcc aat gtc atc agc      583
Ile Asp Pro Thr Tyr Phe Leu Ser Arg Thr Val Ser Asn Val Ile Ser
        170                 175                 180 tcc att gtc ttc gga gac cgc ttt gac tat gag gac aaa gag ttc ctc      631
Ser Ile Val Phe Gly Asp Arg Phe Asp Tyr Glu Asp Lys Glu Phe Leu
185                 190                 195 gca ctg ctg cgg atg atg ctg gga agc ttt cag ttc aca gct acc tct      679
Ala Leu Leu Arg Met Met Leu Gly Ser Phe Gln Phe Thr Ala Thr Ser
200                 205                 210                 215 acc gga cag ctc tat gag atg ttc tac tcg gtg atg aaa cac ctg cca      727
Thr Gly Gln Leu Tyr Glu Met Phe Tyr Ser Val Met Lys His Leu Pro
                220                 225                 230 ggg ccg cag caa cag gca ttt aag gac ctg cag ggg ctg gag gac ttc      775
Gly Pro Gln Gln Gln Ala Phe Lys Asp Leu Gln Gly Leu Glu Asp Phe
            235                 240                 245 ata gcc agg aag gtg gaa cac aac cag cgc acg ctg gat ccc aac tcc      823
Ile Ala Arg Lys Val Glu His Asn Gln Arg Thr Leu Asp Pro Asn Ser
        250                 255                 260 ccg cga gac ttc atc gac tcc ttc ctc atc cgc atg cag gag gag aag      871
Pro Arg Asp Phe Ile Asp Ser Phe Leu Ile Arg Met Gln Glu Glu Lys
265                 270                 275
```

```
aag aat cct gac acc gag ttc tat tgg aag aac ctg gtt ctg acc aca      919
Lys Asn Pro Asp Thr Glu Phe Tyr Trp Lys Asn Leu Val Leu Thr Thr
280                 285                 290                 295 ctg aac ctc ttc ttc gcg ggc acc gag acg gtc agc aca acg atg cgc      967
Leu Asn Leu Phe Phe Ala Gly Thr Glu Thr Val Ser Thr Thr Met Arg
                300                 305                 310 tac ggc ttc ctg ctg ctc atg aag cac ccg gat gtg gag gcc aaa gtc     1015
Tyr Gly Phe Leu Leu Leu Met Lys His Pro Asp Val Glu Ala Lys Val
            315                 320                 325 cac gag gag att gac cgc gtg atc ggc agg aac cgc cag gcc aag ttc     1063
His Glu Glu Ile Asp Arg Val Ile Gly Arg Asn Arg Gln Ala Lys Phe
        330                 335                 340 gag gac cgg gcc aag atg ccc tac acg gag gcc gtg atc cac gag atc     1111
Glu Asp Arg Ala Lys Met Pro Tyr Thr Glu Ala Val Ile His Glu Ile
345                 350                 355 cag aga ttc gga gac atg atc ccc atg ggc ctg gcc cga aga gtc acc     1159
Gln Arg Phe Gly Asp Met Ile Pro Met Gly Leu Ala Arg Arg Val Thr
360                 365                 370                 375 aag gat acc aag ttt cgg gac ttc ctc ctc ccc aag ggc act gag gtg     1207
Lys Asp Thr Lys Phe Arg Asp Phe Leu Leu Pro Lys Gly Thr Glu Val
                380                 385                 390 ttc cct atg ctg ggc tct gtg ctg aga gac ccc aag ttc ttc tcc aac     1255
Phe Pro Met Leu Gly Ser Val Leu Arg Asp Pro Lys Phe Phe Ser Asn
            395                 400                 405 ccc cga ggc ttc aac ccc cag cac ttc ctg gat gag aac ggg cag ttt     1303
Pro Arg Gly Phe Asn Pro Gln His Phe Leu Asp Glu Asn Gly Gln Phe
        410                 415                 420 aag aag aat gat gct ttt gtg ccc ttc tcc atc gga aag cgg tac tgt     1351
Lys Lys Asn Asp Ala Phe Val Pro Phe Ser Ile Gly Lys Arg Tyr Cys
425                 430                 435 ttc gga gaa ggt ctg gct aga atg gag ctc ttc ctc ttc ctc acc aac     1399
Phe Gly Glu Gly Leu Ala Arg Met Glu Leu Phe Leu Phe Leu Thr Asn
440                 445                 450                 455 atc ctg cag aac ttc cac ctc aag tct ccg cag ctg ccc cag gac atc     1447
Ile Leu Gln Asn Phe His Leu Lys Ser Pro Gln Leu Pro Gln Asp Ile
                460                 465                 470 gac gtg tcc ccc aaa cac gtg ggc ttc gcc acc atc ccc ccg acc tac     1495
Asp Val Ser Pro Lys His Val Gly Phe Ala Thr Ile Pro Pro Thr Tyr
            475                 480                 485 acc atg agc ttc ctg ccc cgc tga                                     1519
Thr Met Ser Phe Leu Pro Arg
        490

<210> SEQ ID NO 19
<211> LENGTH: 494
<212> TYPE: PRT
<213> ORGANISM: Sus scrofa

<400> SEQUENCE: 19

Met Leu Ala Ser Gly Leu Leu Val Ala Leu Leu Thr Cys Leu Thr
1               5                   10                  15

Ile Met Val Leu Met Ser Val Trp Arg Gln Arg Lys Leu Gln Gly Lys
                20                  25                  30

Leu Pro Pro Gly Pro Thr Pro Leu Pro Phe Ile Gly Asn Tyr Leu Gln
            35                  40                  45

Leu Asn Thr Glu Gln Met Tyr Asn Ser Leu Met Lys Ile Ser Gln Arg
        50                  55                  60

Tyr Gly Pro Val Phe Thr Val His Leu Gly Pro Arg Arg Ile Val Val
65                  70                  75                  80
```

-continued

Leu Cys Gly Tyr Asp Ala Val Lys Glu Ala Leu Val Asp Gln Ala Glu
            85                  90                  95
Glu Phe Ser Gly Arg Gly Gln Ala Thr Phe Asp Trp Leu Phe Lys
            100                 105                 110
Gly Tyr Gly Val Ala Phe Ser Asn Gly Glu Arg Ala Lys Gln Leu Arg
            115                 120                 125
Arg Phe Ser Ile Thr Thr Leu Arg Asp Phe Gly Val Gly Lys Arg Gly
    130                 135                 140
Ile Glu Glu Arg Ile Gln Glu Ala Gly His Leu Ile Glu Ala Phe
145                 150                 155                 160
Arg Gly Thr Arg Gly Ala Phe Ile Asp Pro Thr Tyr Phe Leu Ser Arg
                165                 170                 175
Thr Val Ser Asn Val Ile Ser Ser Ile Val Phe Gly Asp Arg Phe Asp
                180                 185                 190
Tyr Glu Asp Lys Glu Phe Leu Ala Leu Leu Arg Met Met Leu Gly Ser
            195                 200                 205
Phe Gln Phe Thr Ala Thr Ser Thr Gly Gln Leu Tyr Glu Met Phe Tyr
    210                 215                 220
Ser Val Met Lys His Leu Pro Gly Pro Gln Gln Ala Phe Lys Asp
225                 230                 235                 240
Leu Gln Gly Leu Glu Asp Phe Ile Ala Arg Lys Val Glu His Asn Gln
                245                 250                 255
Arg Thr Leu Asp Pro Asn Ser Pro Arg Asp Phe Ile Asp Ser Phe Leu
            260                 265                 270
Ile Arg Met Gln Glu Glu Lys Lys Asn Pro Asp Thr Glu Phe Tyr Trp
    275                 280                 285
Lys Asn Leu Val Leu Thr Thr Leu Asn Leu Phe Phe Ala Gly Thr Glu
290                 295                 300
Thr Val Ser Thr Thr Met Arg Tyr Gly Phe Leu Leu Leu Met Lys His
305                 310                 315                 320
Pro Asp Val Glu Ala Lys Val His Glu Glu Ile Asp Arg Val Ile Gly
                325                 330                 335
Arg Asn Arg Gln Ala Lys Phe Glu Asp Arg Ala Lys Met Pro Tyr Thr
            340                 345                 350
Glu Ala Val Ile His Glu Ile Gln Arg Phe Gly Asp Met Ile Pro Met
            355                 360                 365
Gly Leu Ala Arg Arg Val Thr Lys Asp Thr Lys Phe Arg Asp Phe Leu
370                 375                 380
Leu Pro Lys Gly Thr Glu Val Phe Pro Met Leu Gly Ser Val Leu Arg
385                 390                 395                 400
Asp Pro Lys Phe Phe Ser Asn Pro Arg Gly Phe Asn Pro Gln His Phe
                405                 410                 415
Leu Asp Glu Asn Gly Gln Phe Lys Lys Asn Asp Ala Phe Val Pro Phe
            420                 425                 430
Ser Ile Gly Lys Arg Tyr Cys Phe Gly Glu Gly Leu Ala Arg Met Glu
            435                 440                 445
Leu Phe Leu Phe Leu Thr Asn Ile Leu Gln Asn Phe His Leu Lys Ser
450                 455                 460
Pro Gln Leu Pro Gln Asp Ile Asp Val Ser Pro Lys His Val Gly Phe
465                 470                 475                 480
Ala Thr Ile Pro Pro Thr Tyr Thr Met Ser Phe Leu Pro Arg
                485                 490